(12) United States Patent
Evans

(10) Patent No.: US 11,400,059 B2
(45) Date of Patent: Aug. 2, 2022

(54) TREATMENT OF PAIN AND/OR PAIN RELATED SYMPTOMS ASSOCIATED WITH DYSMENORRHEA

(71) Applicant: ALYRA BIOTECH PTY LTD, Eastwood (AU)

(72) Inventor: Susan Florence Evans, Kent Town (AU)

(73) Assignee: ALYRA BIOTECH PTY LTD, Eastwood (AU)

( * ) Notice: Subject to any disclaimer, the term of this patent is extended or adjusted under 35 U.S.C. 154(b) by 0 days.

(21) Appl. No.: 16/906,803

(22) Filed: Jun. 19, 2020

(65) Prior Publication Data

US 2020/0383937 A1 Dec. 10, 2020

Related U.S. Application Data

(63) Continuation-in-part of application No. PCT/AU2018/051383, filed on Dec. 21, 2018.

(30) Foreign Application Priority Data

Dec. 22, 2017 (AU) ................................. 2017905151

(51) Int. Cl.
| | |
|---|---|
| *A61K 31/135* | (2006.01) |
| *A61P 15/00* | (2006.01) |
| *A61K 9/00* | (2006.01) |
| *A61K 31/216* | (2006.01) |
| *A61K 31/567* | (2006.01) |

(52) U.S. Cl.
CPC .......... *A61K 31/135* (2013.01); *A61K 9/0039* (2013.01); *A61K 31/216* (2013.01); *A61K 31/567* (2013.01); *A61P 15/00* (2018.01)

(58) Field of Classification Search
CPC .............. A61K 2300/00; A61K 31/135; A61K 31/567; A61K 31/12; A61K 31/18; A61K 31/194; A61K 31/216; A61K 31/522; A61K 31/65; A61K 31/739; A61K 47/36; A61K 9/0034; A61K 9/0039; A61K 9/02; A61K 9/06; A61M 31/002; A61P 15/00; A61P 29/00

See application file for complete search history.

(56) References Cited

U.S. PATENT DOCUMENTS

| | | | |
|---|---|---|---|
| 2013/0074846 A1* | 3/2013 | Mock ..................... | A61F 6/144 128/833 |
| 2015/0313892 A1 | 11/2015 | Singh et al. | |

FOREIGN PATENT DOCUMENTS

| | | |
|---|---|---|
| CN | 101480389 A | 7/2009 |
| RU | 2607661 C1 | 1/2017 |
| WO | WO-2008/137012 A1 | 11/2008 |
| WO | WO-2012/122472 A1 | 9/2012 |
| WO | WO-2014/121332 A1 | 8/2014 |
| WO | WO-2015/189853 A1 | 12/2015 |
| WO | WO-2018/075730 A1 | 4/2018 |
| WO | WO-2019/119059 A1 | 6/2019 |

OTHER PUBLICATIONS

Shoupe (Handbook of Gynecology, pp. 1-10, 2016) (Year: 2016).*
Mirena (Bayer Health Pharmaceuticals, Jul. 2008) (Year: 2008).*
Sator-Katzenschlager et al. (Wien Klin Wochenschr 2005, 117/21-22, 761-768) (Year: 2005).*
Ishii, et al., "Alpha-Lipoic Acid inhibits NF-kB signal transduced inflammatory cytokines secretion in LPS-induced Human Gingival Fibroblasts", J Jpn Soc Periodontol, 59(1):28-38 (Mar. 2017).
International Search Report of corresponding PCT application No. PCT/AU2018/051383. Search reported dated Jan. 22, 2019.
International-type search for Australian Provisional Patent Application 2017905151 dated Aug. 30, 2018.
Allhorn S., et al., "TLR3 and TLR4 Expression in Healthy and Diseased Human Endometrium." Reproductive Biology and Endocrinology 6, No. 1 (Sep. 7, 2008).
Baldaszti, et al., "Acceptability of the long-term contraceptive levonorgestrel-releasing intrauterine system (Mirena®): a 3-year follow-up study," Contraception 67(2); pp. 87-91 (2003).
Extended European Search Report dated Dec. 15, 2021, issued in EP Application No. 18890747.1 (15 pages).
Khan, KN, et al., "17β-Estradiol and Lipopolysaccharide Additively Promote Pelvic Inflammation and Growth of Endometriosis." Reproductive Sciences 22, No. 5: 585-94 (2015).
Liang, et al., "Levonorgestrel Ameliorates Adenomyosis via lncRNA HI9/miR-17/TLR4 Pathway," Drug Design, Development and Therapy, 14: 3449-3460 (Jan. 1, 2020).

* cited by examiner

*Primary Examiner* — Umamaheswari Ramachandran
(74) *Attorney, Agent, or Firm* — Marshall, Gerstein & Borun LLP

(57) ABSTRACT

The present disclosure relates to methods, compositions and products for treating pain, and/or pain related symptoms, associated with dysmenorrhea in a subject. In certain embodiments, the present disclosure provides a method of treating pain, and/or pain related symptoms, associated with dysmenorrhea in a subject, the method comprising intrauterine and/or vaginal administration to the subject of an effective amount of an agent that reduces activation of the innate immune system and thereby treating the pain and/or the pain related symptoms in the subject. Other embodiments are also disclosed.

14 Claims, 32 Drawing Sheets

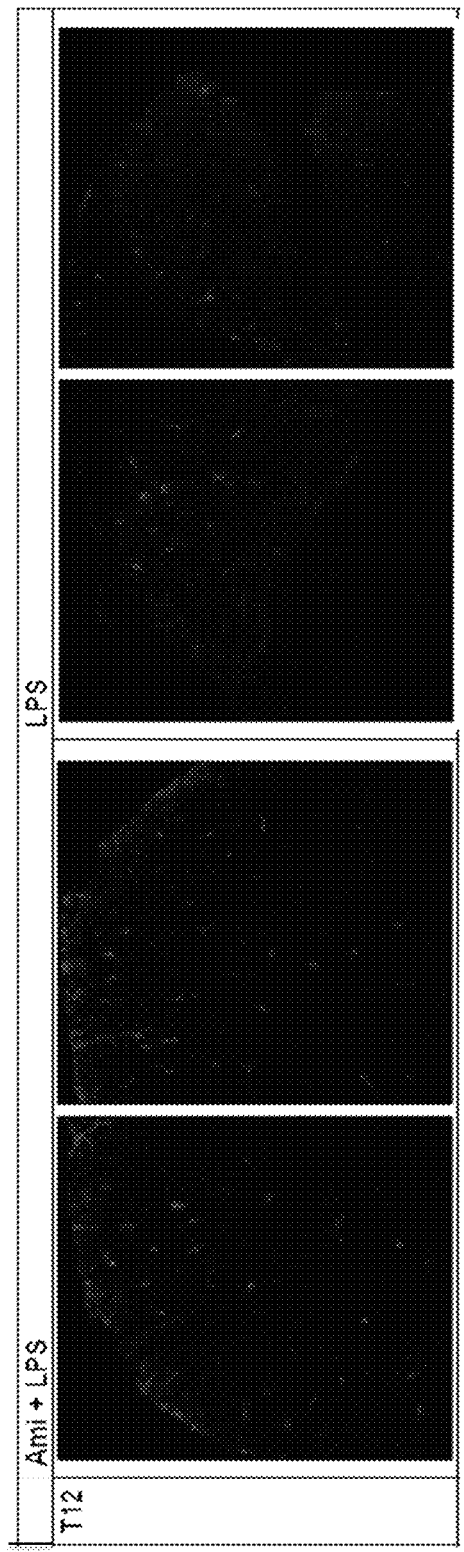

TREATMENT OF PAIN AND/OR PAIN RELATED SYMPTOMS ASSOCIATED WITH DYSMENORRHEA

PRIORITY CLAIM

This application is a continuation-in-part of International Patent Application No. PCT/AU2018/051383, filed on 21 Dec. 2018, which claims priority to Australian Provisional Patent Application No. 2017905151, filed on 22 Dec. 2017, the contents of which are hereby incorporated by reference in their entirety.

FIELD

The present disclosure relates, at least in part, to methods, compositions and products for treating pain, and/or pain related symptoms, associated with dysmenorrhea in a subject.

BACKGROUND

Dysmenorrhea is the medical term used to describe pain experienced during menstruation. The pain is considered to be uterine in origin and is usually perceived as being in the pelvis or lower abdomen but may be felt in the lower back or thighs. Whilst dysmenorrhea may be the sole symptom present, it may also be associated with additional pain symptoms such as bladder pain (commonly associated with frequency, urgency or nocturia), bowel pain (commonly associated with a bloated feeling, diarrhoea, or constipation), musculoskeletal pain (commonly felt as an ache, sharp, stabbing or sudden pain), chronic non-specific pelvic pain, or pain associated with intercourse.

Dysmenorrhea is a major problem affecting a significant proportion of the female population. For example, a study of Australian girls aged 16-18 showed that while 93% experienced some pain with menstruation, 21% experienced severe pain, frequently associated with disruption of life activities and school absence. It is a frequent cause of emergency department presentation and hospital admission.

Pelvic pain is estimated to affect up to 25% of the female population. While there are many causes of pelvic pain, dysmenorrhea is a common symptom, which may be present alone or be associated with other pelvic symptoms. In some cases, clinical assessment of this pain leads to a diagnosis of pain associated with dysmenorrhea. Indeed, many women suffering with chronic pelvic pain will describe dysmenorrhoea from soon after menarche as the first pain symptom experienced in their progression to chronic pelvic pain and additional pelvic symptoms.

There are a number of management options available for pain associated with dysmenorrhea. For example, management with non-steroidal anti-inflammatory drugs (NSAIDs) may assist with relief of pain. However, these types of treatment may have adverse effects such as nausea, dyspepsia, peptic ulcer, and diarrhoea, which make them unsuitable for regular use, or they are insufficiently effective for the management of pain. Hormonal managements including (but not limited to) the oral contraceptive pill, oral progestogens, or gonadotrophin-releasing hormone agonists may improve symptoms in some women, particularly in the short term. However, these managements may be insufficiently effective for the management of pain and pain related symptoms, may be associated with adverse effects, or may be unacceptable to some women.

Another management option involves the insertion of a device loaded with levonorgestrel into the uterus. However, in some women this is associated with an increase in pelvic pain, which is recognised as a major reason for premature removal of the device.

The actual biological mechanisms underlying pain associated with dysmenorrhea are incompletely understood, leading to an absence of targeted therapies.

Accordingly, there is a need for new treatment and management options for pain, and/or pain related symptoms, associated with dysmenorrhea. The present disclosure is directed to overcoming and/or at least ameliorating one of more disadvantages of the prior art, and/or provide one or more advantages as discussed herein.

SUMMARY

The present disclosure is based on the initial recognition that women may present with similar pelvic profiles either with and without endometriotic lesions, and as such pain symptoms in women with dysmenorrhea are likely to be influenced by other factors. In addition, it has also been recognised in the present disclosure that dysmenorrhoea-associated pelvic pain is likely to be due to activation of the innate immune system, mediated by a number of pattern recognition receptors in the uterus. Using an animal model system, in the present disclosure it has been demonstrated that activation of glial cells in the dorsal horn of the spinal cord occurs in response to intrauterine administration of a potent innate immune activator, and that this activation is ameliorated by intrauterine administration of pattern recognition receptor inhibitors.

Certain embodiments of the present disclosure provide a method of treating pain, and/or pain related symptoms, associated with dysmenorrhea in a subject, the method comprising intrauterine administration to the subject of an effective amount of an agent that reduces activation of the innate immune system and thereby treating the pain and/or the pain related symptoms in the subject.

Certain embodiments of the present disclosure provide use of an agent that reduces activation of the innate immune system by intrauterine administration for treating pain, and/or pain related symptoms, associated with dysmenorrhea in the subject.

Certain embodiments of the present disclosure provide an intrauterine composition for treating pain, and/or pain related symptoms, associated with dysmenorrhea in a subject, the composition comprising an effective amount of an agent that reduces activation of the innate immune system.

Certain embodiments of the present disclosure provide a method of treating pain, and/or pain related symptoms, associated with dysmenorrhea in a subject, the method comprising administration to the subject of a composition as described herein.

Certain embodiments of the present disclosure provide an intrauterine or vaginal pelvic device comprising a releasable agent that reduces activation of the innate immune system.

Certain embodiments of the present disclosure provide a contraceptive intrauterine device comprising a releasable agent that reduces activation of the innate system.

Certain embodiments of the present disclosure provide a method of treating pain, and/or pain related symptoms, associated with dysmenorrhea in a subject, the method comprising use of one or more devices as described herein.

Certain embodiments of the present disclosure provide a solid substrate comprising a releasable agent that reduces activation of the innate system and a releasable sex hormone.

Certain embodiments of the present disclosure provide an intrauterine device comprising one or more substrates as described herein.

Certain embodiments of the present disclosure provide a method of reducing pain, and/or pain related symptoms, associated with the insertion and/or residency of an intrauterine device, the method comprising intrauterine administration to the subject of an agent that reduces activation of the innate immune system.

Certain embodiments of the present disclosure provide a method of identifying an agent for treating pain, and/or pain related symptoms, associated with dysmenorrhea, the method comprising determining the ability of a candidate agent that reduces activation of the innate immune system to treat pain, and/or pain related symptoms, and thereby identifying the candidate agent as an agent for treating pain, and/or pain related symptoms, associated with dysmenorrhea.

Certain embodiments of the present disclosure provide a method of identifying an agent for treating pain, and/or pain related symptoms, associated with dysmenorrhea, the method comprising:
(i) providing a candidate agent;
(ii) determining the ability of the candidate agent to reduce activation of the innate immune system; and
(iii) determining the ability of a candidate agent that reduces activation of the innate system to treat pain, and/or pain related symptoms, associated with dysmenorrhea, thereby identifying the candidate agent as an agent for treating pain, and/or pain related symptoms, associated with dysmenorrhea.

This summary is not intended to be limiting with respect to the embodiments disclosed herein and other embodiments are disclosed in this specification. In addition, limitations of one embodiment may be combined with limitations of other embodiments to form additional embodiments.

BRIEF DESCRIPTION OF THE FIGURES

For a better understanding of the present disclosure, and to show more clearly how the present disclosure may be carried into effect according to one or more embodiments thereof, reference will be made, by way of example, to the accompanying figures.

FIGS. 8A-8D show amitriptyline treatment blocks the impact of intrauterine LPS at multiple levels of the spinal cord and reduced microglial reactivity to basal levels.

DETAILED DESCRIPTION

Figure 1:
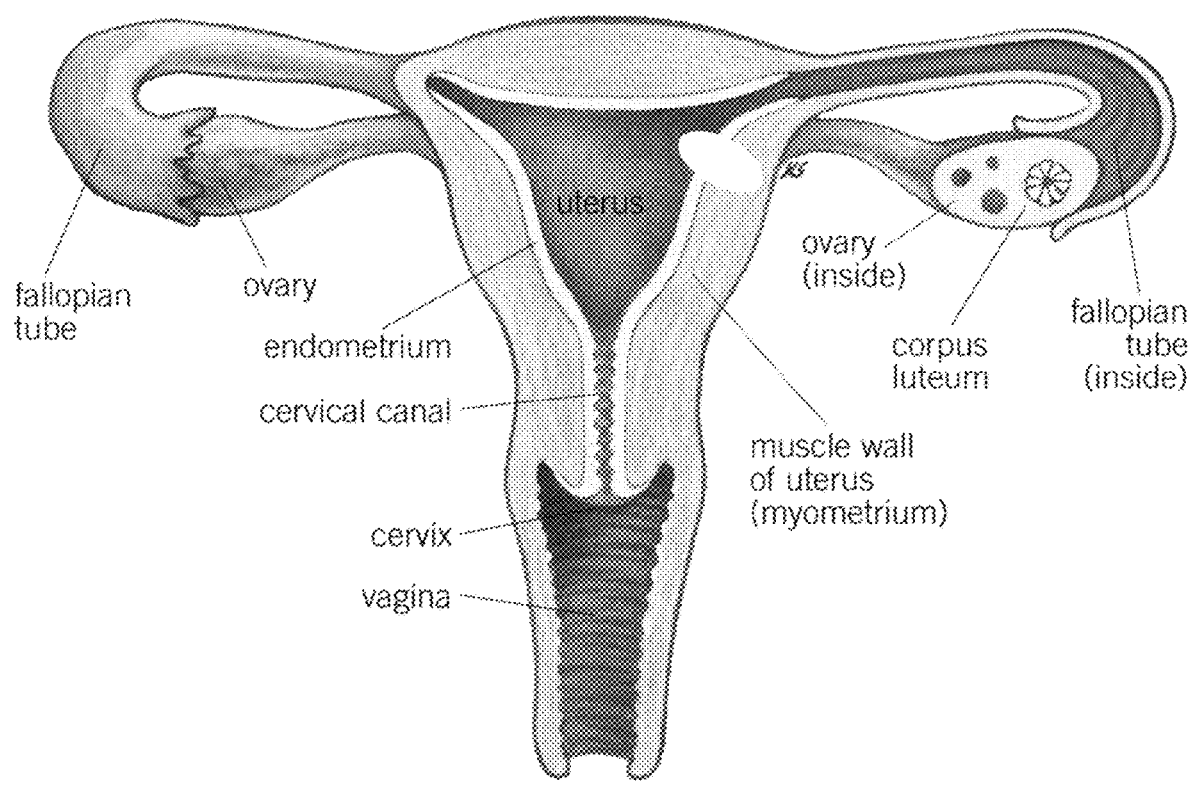
FIG. 1 shows a representation of the female internal reproductive organs including vagina, uterus, fallopian tubes and ovaries.

The present disclosure relates generally to methods, compositions and products for treating or managing pain, and/or pain related symptoms, associated with dysmenorrhea in a subject.

One or more embodiments of the present disclosure are directed to methods and products that have one or more combinations of the following advantages new methods and/or products for treating and/or managing pain, and/or pain related symptoms, associated with dysmenorrhea; methods of treating pain, and/or pain related symptoms, using a delivery route that permits low doses of a therapeutic agent to be used; methods of treating pain, and/or pain related symptoms, using a delivery route that permits long term release of a therapeutic agent to be used; the use of therapeutic agents to treat/manage pain and/or pain related symptoms associated with dysmenorrhea that have a safety profile established over many years; the incorporation of a new class of therapeutic agents previously unrecognised as being suitable for use in intrauterine devices; new methods for reducing pain and/or pain related symptoms associated with insertion and/or residency of intrauterine devices; new methods for treating pain and/or pain related symptoms associated with dysmenorrhea that reduce the need for, or tolerance to, opioid pain medications; to address one or more problems, and/or to provide one or more advantages, or to provide a commercial alternative. Other advantages of certain embodiments of the present disclosure are also disclosed herein.

Certain embodiments of the present disclosure provide a method of treating pain, and/or pain related symptoms, associated with dysmenorrhea in a subject.

The phrase "pain, and/or pain related symptoms associated with dysmenorrhea" as used herein refers to pain, and/or pain related symptoms present in a female subject at any time of the menstrual cycle, and who is suffering or has previously suffered from dysmenorrhea even if dysmenorrhea is not clinically present at any particular time or at the time of treatment.

In certain embodiments, the present disclosure provides a method of treating pain, and/or pain related symptoms, associated with dysmenorrhea in a subject, the method comprising intrauterine and/or vaginal administration to the subject of an effective amount of an agent that reduces activation of the innate immune system and thereby treating the pain and/or the pain related symptoms in the subject.

In certain embodiments, the present disclosure provides an agent that reduces activation of the innate immune system for use in treating pain, and/or pain related symptoms, associated with dysmenorrhea in a subject by intrauterine or vaginal administration to the subject.

In certain embodiments, the pain associated with dysmenorrhea comprises pelvic pain. In this regard, pelvic pain associated with dysmenorrhea refers to a clinical condition whereby a patient suffers from sporadic, recurrent, episodic, persistent or chronic pelvic pain, and dysmenorrhea is either a current symptom, or dysmenorrhea has been present in the past.

The term "pain" as used herein refers to an unpleasant sensory and emotional experience associated with actual or potential tissue damage, or described in terms of such damage, for example as described in Part III: Pain Terms, A Current List with Definitions and Notes on Usage" (pp 209-214) Classification of Chronic Pain, Second Edition, IASP Task Force on Taxonomy, edited by H. Merskey and N. Bogduk, IASP Press, Seattle, 1994. Methods for assessing pain are known in the art.

In certain embodiments, the pain related symptoms comprise one or more of the following: nausea, fatigue, bowel symptoms (eg irritable bowel syndrome), vulval pain, back pain, symptoms due to pelvic muscle pain or spasm, chronic pelvic pain, or pain associated with intercourse. Other types of pain related symptoms are contemplated.

The term "treatment", and related terms such as "treating" and "treat" as used herein, refer to obtaining a desired pharmacologic and/or physiologic effect in terms of improving the condition of the subject, ameliorating, arresting, preventing, managing, suppressing, relieving and/or slowing the progression of one or more symptoms in the subject, a partial or complete stabilization of the subject, a regression of one or more symptoms, or a cure in the subject.

The term "an agent that reduces activation of the innate immune system" as used herein refers to an agent that directly or indirectly results in a reduction in the level of the innate immune system, for example so as to cause a decrease in the level of activation, an inhibition of activation, a prevention of activation, a downregulation in the level of activation, a reduction in the ability to be stimulated, an alteration in the timing and/or location of activation, otherwise provide some form of negative control over activation or combinations thereof.

For example, the agent may (i) act to directly reduce activation, alter the level of expression of a target, alter localisation of a target, alter signalling, and/or alter timing of function, (ii) act to change the activity of a signalling pathway associated with activation, (iii) act to alter the level and/or the activity of another molecule that regulates a target, such as by competitive/non-competitive binding, or by altering the synthesis, breakdown, and/or localisation of the other molecule. Other forms of action are contemplated, and combinations of forms of action are contemplated.

Examples of agents include a drug, a small molecule, a protein, a polypeptide, a lipid, a carbohydrate, a nucleic acid, an oligonucleotide, a ribozyme, a biologic, an aptamer, a cofactor, a ligand, a ligand mimetic, a receptor, a peptidomimetic, an enzyme, a kinase, a phosphatase, a cytokine, a growth factor, a metal ion, a chelate, an antisense nucleic acid, an inhibitor RNA, a microRNA, a siRNA, an antibody or an antigen binding part thereof, an antibody mimetic, or combinations thereof. Other types of agents are contemplated. It will be appreciated than an agent as described herein also includes a prodrug of the agent, and/or a metabolite of the agent.

In certain embodiments, the agent comprises a drug or small molecule, and/or a prodrug or a metabolite thereof.

In certain embodiments, the agent comprises a nucleic acid. In certain embodiments, the agent comprises an antibody and/or an antigen binding part thereof.

In certain embodiments, the agent that reduces activation of the innate immune system comprises an agent that reduces activation of a target that is activated or induced by LPS treatment.

In certain embodiments, the agent that reduces activation of the innate immune system comprises an agent that reduces activation of a target that is inhibited or antagonised by amitriptyline.

In certain embodiments, the agent that reduces activation of the innate immune system comprises an agent that reduces activation of spinal glia. In certain embodiments, the agent that reduces activation of the innate immune system comprises an agent that reduces activation of spinal astrocytes. In certain embodiments, the agent that reduces activation of the innate immune system comprises an agent that reduces activation of spinal microglia. In certain embodiments, the agent that reduces activation of the innate immune system comprises an agent that reduces activation of spinal astrocytes and spinal microglia. In certain embodiments, the agent that reduces activation of the innate immune system comprises an agent that reduces activation of a pattern-recognition receptor. In this regard, spinal glial cells, such as astrocytes and microglia, express a wide range of pattern-recognition receptors, which have a role in activation of glial cells.

The term "pattern recognition receptor inhibitor" or variants thereof as used herein refers to a direct or indirect inhibitor of a receptor and/or its downstream signalling systems. In certain embodiments, the inhibitor is a selective inhibitor. In certain embodiments, the inhibitor is a non-selective inhibitor.

In certain embodiments, the agent is a direct inhibitor of a receptor. In certain embodiments, the agent is an indirect inhibitor of a receptor.

In certain embodiments, the agent is a direct receptor antagonist. In certain embodiments, the agent is an indirect receptor antagonist. In certain embodiments, the antagonist is a selective antagonist. In certain embodiments, the antagonist is a non-selective antagonist.

Pattern recognition receptors are described, for example, Deswaerte et al. (2017) *Mol. Immunology* 86: 3-9. Agents for reducing activation of pattern recognition receptors are known in the art, commercially available or can be identified by screening. Inhibitors and antagonists of pattern recognition receptors are described, for example, in Mullen et al. (2015) *Arthritis Res Ther.* 17(1): 122.

Pattern recognition receptors include Toll-like receptors (TLRs), C-type lectin receptors, NOD-like receptors, Retinoic acid-inducible gene-1-like receptors (RIG-1-like receptors), and Melanoma-differentiation-associated gene 5 receptors (MDA-5).

Examples of pattern recognition receptor antagonists include NI-0101 (TLR4 target; antibody), Chaperonin 10 (TLR4 antagonist; protein), VTX-763 (TLR8 target; small molecule), CRID3 (NLRP3 target; small molecule), OPN-305 (TLR2 target; antibody). IMO-3100 (TLR7/TLR9 target; DNA based small molecule), DV1179 (TLR7/TLR9 target; small molecule), and CPG52364 (TLR7/TLR9 target; small molecule).

In certain embodiments, the agent that reduces activation of the innate immune system comprises an inhibitor or an antagonist of a Toll-like Receptor (TLR). Functions of Toll-like receptors and their downstream signalling events are known in the art, for example as described in Barton G M, Kagan J C (2009)*Nat. Rev. Immunol.* 9(8), 535-42; Blasius A L, Beutler B (2010) *Immunity* 32(3), 305-15; Kawai T, Akira S (2010) *Nat. Immunol.* 11(5), 373-84; Lester S N, Li K (2014) *J. Mol. Biol.* 426(6), 1246-64; Li X, Jiang S, Tapping R I (2010) *Cytokine* 49(1), 1-9; McGettrick A F, O'Neill L A (2010) *Curr. Opin. Immunol.* 22(1), 20-7; Miggin S M, O'Neill L A (2006) *J. Leukoc. Biol.* 80(2), 220-6; Pasare C, Medzhitov R (2005) *Adv. Exp. Med. Biol.* 560, 11-8; and Reuven E M, Fink A, Shai Y (2014) *Biochim. Biophys. Acta* 1838(6), 1586-93. Methods for identifying agents that inhibit or antagonise Toll-like receptors are known in the art, and described herein. Agents that inhibit or antagonise a Toll-like receptor are known in the art, commercially available, or can be identified by screening.

In certain embodiments, the agent that reduces activation of the innate immune system comprises an inhibitor or an antagonist of a C-type lectin receptor (CLR). C-Type lectin receptors are described, for example, in Del Fresno et al. (2018) *Front Immunol.* 9: 804. Methods for identifying agents that inhibit or antagonise C-type lectin receptors are known in the art, and described herein. Agents that inhibit or antagonise C-type lectin receptors are known in the art, commercially available or can be identified by screening.

In certain embodiments, the agent that reduces activation of the innate immune system comprises an inhibitor or an antagonist of a NOD-like receptor (NDR). NOD-like receptors are described, for example, in Platnich and Muruve (2019) *Arch Biochem Biophys.* 670:4-14 and in Feerick and McKeman (2017) Immunology 150(3): 237-247. Methods for identifying agents that inhibit or antagonise NOD-like receptors are known in the art, and described herein. NOD-like receptors are described, for example, in Feerick and McKernan (2017) Immunology 150(3): 237-247. Agents that inhibit or antagonise NOD-like receptors are known in the art, commercially available or can be identified by screening.

Examples of antagonist/inhibitors of NOD-like receptors include MCC950 (selective NLRP3 inhibitor), CY-09 (selective and direct NLRP3 inhibitor), NOD-IN-1 (inhibitor of NOD1 and NOD2), Nodinitib-1 (NOD1 inhibitor), and YQ128 selective NLRP3 inhibitor).

In certain embodiments, the agent that reduces activation of the innate immune system comprises an inhibitor of one of more TLR4 (GeneCard GCID: GC09P117704), TLR3 (GeneCard GCID: GC04P186059), TLR2 (GeneCard GCID: GC04P153684), TLR5 (GeneCard GCID: GC01M223109), TLR8 (GeneCard GCID: GC0XP01292), TLR9 (GeneCard GCID: GC03M052222), Dectin-1a (GeneCard GCID: GC12M013368), Dectin 1-b (GeneCard GCID: GC12M013368), Mincle (GeneCard GCID: GC12M008535), NOD1 (GeneCard GCID: GC12M008535), and NOD2 (GeneCard GCID: GC16P050693), RIG-1 (GeneCard GCID:GC09M032455) or MDA-5 (GeneCard GCID:GC02M162267.

In certain embodiments, the agent that reduces activation of the innate immune system comprises an agent that inhibits a Toll-like receptor 4 (TLR4). Methods for determining whether an agent is a TLR4 inhibitor or antagonist are known in the art, for example as described in Coats S R. et al. (2005). *J Immunol.* 175(7):4490-8.

In certain embodiments, the agent that reduces activation of the innate immune system comprises an agent that inhibits a Toll-like receptor 2 (TLR2).

In certain embodiments, the agent that reduces spinal glial activation comprises a TLR4 inhibitor. In certain embodiments, the TLR4 inhibitor is a selective inhibitor. In certain embodiments, the TLR4 inhibitor is a non-selective inhibitor.

In certain embodiments, the agent that reduces spinal glial activation comprises a TLR4 antagonist. In certain embodiments, the TLR4 antagonist is a selective antagonist. In certain embodiments, the TLR4 antagonist is a non-selective antagonist.

Examples of TLR4 inhibitors or antagonists include one or more of Eritoran, Amitriptyline (for example available from Mylan Pharmaceuticals Inc, USA), Nortriptyline (for example available from Centaur Pharmaceuticals), Cyclobenzaprine (for example available from Jubilant Life Sciences), Ketotifen (for example available from Sifavitor), Imipramine (for example available from H. Lundbeck AS), Mianserin (for example available from Albany Molecular Research Inc.), Ibudilast (for example available from Sanyo Chemical Laboratory Ltd), Pinocembrin, (+) Naltrexone, (−) Naltrexone, (+) Naloxone, (−) Naloxone, minocycline (for example available from Albany Molecular Research Inc.), LPS-RS, Propentofylline (for example Labratorio Chimico Internazionale Spa) and (+)-naloxone, 1J, TAK-242, Desipramine (for example available from H. Lundbeck AS), Carbamazepine (for example available from SAFC, Sigma-Aldrich Corporation) Oxcarbazepine (for example available from Albany Molecular Research Inc.), Rimcazole, Mesoridazine (for example available from Sumika Fine Chemicals Co Ltd), Tacrine (for example available from Nordic Syhtnesis AB), Orphenadrine (for example available from Kores India Limited), Diphenhydramine (for example available from Cadila Pharmaceuticals Limited, Duloxetine (for example available from BOC Sciences), Venlafaxine (for example available from Macleods Pharmaceuticals Limited), Chlorpromazine (for example available from Egis Pharmaceuticals PLC), Fluoxetine (for example available from PRONOVA BIOPHARMA NORGE AS), curcumin, an effective cannabinoid, and compounds Lipid A mimetic, SPA4, STM28, xanthohumal, JTT-705, auranofin, sulforaphane, cinnamaldehyde, taxanes, 6-shogaol, soliquiritigenin, OSL07, glycyrrhizin, isoliquiritigenin, caffeic acid phenethyl ester, IAXO-101, T5342126, KRGISPGGGS-DAQGEV, morphine, NCI126224, paclitaxel, heme, chitohexaose, compounds 12 to 18, 22, and 29 to 33 as described in Wang et al (2013) *Chem Soc Rev.* 42(12): 4859-4866.

In certain embodiments, the TLR4 inhibitor or antagonist comprises a small molecule. In certain embodiments the TLR4 inhibitor or antagonist comprises an antibody and/or an antigen binding part thereof. In certain embodiments the TLR4 inhibitor or antagonist comprises a nucleic acid.

In certain embodiments, the TLR4 inhibitor comprises amitriptyline and/or nortriptyline. In certain embodiments, the TLR4 inhibitor comprises TAK242.

In certain embodiments, the agent that reduces activation of the innate immune system comprises a TLR2 inhibitor. In certain embodiments, the TLR2 inhibitor is a selective inhibitor. In certain embodiments, the TLR2 inhibitor is a non-selective inhibitor.

In certain embodiments, the agent that reduces activation of the innate immune system comprises a TLR2 antagonist. In certain embodiments, the TLR2 antagonist is a selective antagonist. In certain embodiments, the TLR2 antagonist is a non-selective antagonist.

TLR2 inhibitors and antagonists are known, and are commercially available or may be produced by a method known in the art. Examples of TLR2 inhibitors or antagonists include one or more of tricyclics including amitriptyline (for example available from Mylan Pharmaceuticals Inc, USA), and agents such as CU-CPT22 (for example available from Calbiochem), Sparstolonin B (available from Sigma Aldrich), and sulphoglycolipids, and compounds 1 to 5 as described in Wang et al (2013) Chem Soc Rev. 42(12): 4859-4866. Methods for determining whether an agent is a TLR2 inhibitor or antagonist are known in the art, for example as described in Cheng, K., et al. 2012. *Angew. Chem. Int. Ed.* 51, 12246.

In certain embodiments, the TLR2 inhibitor or antagonist comprises a small molecule. In certain embodiments the TLR2 inhibitor or antagonist comprises an antibody and/or an antigen binding part thereof. In certain embodiments the TLR2 inhibitor or antagonist comprises a nucleic acid.

In certain embodiments, the inhibitor or antagonist is both a TLR2 inhibitor or antagonist and a TLR4 inhibitor or antagonist.

In certain embodiments, the agent that reduces activation of the innate immune system comprises one or more of a TLR4 inhibitor, a TLR2 inhibitor, minocycline, fluorocitrate, and propentofylline.

In certain embodiments, the agent that reduces activation of the innate immune system comprises amitriptyline. In this regard, amitriptyline has both TLR4 and TLR2 inhibitor activity.

In certain embodiments, the agent that reduces activation of the innate immune system comprises nortriptyline.

In certain embodiments, the agent that reduces activation of the innate immune system comprises TAK242.

In certain embodiments, the present disclosure provides a method of treating pain, and/or pain related symptoms, associated with dysmenorrhea in a subject, the method comprising intrauterine administration to the subject of an effective amount of amitriptyline and thereby treating the pain, and/or the pain related symptoms in the subject.

In certain embodiments, the present disclosure provides a method of treating pain, and/or pain related symptoms, associated with dysmenorrhea in a subject, the method comprising intrauterine and/or vaginal administration to the subject of an effective amount of nortriptyline and thereby treating the pain, and/or the pain related symptoms in the subject.

In certain embodiments, the present disclosure provides a method of treating pain, and/or pain related symptoms, associated with dysmenorrhea in a subject, the method comprising intrauterine and/or vaginal administration to the subject of an effective amount of TAK242 and thereby treating the pain and/or the pain related symptoms in the subject.

It will be understood that while various embodiments of the present disclosure are directed to pain, and/or pain related symptoms, associated with dysmenorrhea in humans, veterinary applications of the present disclosure are also contemplated.

In certain embodiments, the subject is suffering from pain, and/or pain related symptoms, associated with dysmenorrhea. In certain embodiments, the subject is susceptible to developing pain, and/or pain related symptoms, associated with dysmenorrhea.

In certain embodiments, the subject is suffering from pelvic pain associated with dysmenorrhea. In certain embodiments, the subject is susceptible to developing pelvic pain associated with dysmenorrhea.

In certain embodiments, the subject is susceptible to progression of pain, and/or pain related symptoms, from a less severe state to a more severe state. In certain embodiments, the subject is susceptible to progression of pelvic pain from a less severe state to a more severe state.

In certain embodiments, the subject is susceptible to developing pain, and/or pain related symptoms, associated with the insertion and/or residency of an intrauterine device. In certain embodiments, the subject is susceptible to developing pelvic pain associated with the insertion and/or residency of an intrauterine device.

In certain embodiments, the method is used to reduce pain, and/or pain related symptoms, associated with dysmenorrhea.

In certain embodiments, the method is used to reduce the intensity of pain and/or the frequency of episodes of pain. In certain embodiments, the treating of the pain associated with dysmenorrhea comprises reducing the intensity of the pain and/or the frequency of episodes of the pain.

In certain embodiments, the method is used to prevent or manage the pain, and/or the pain related symptoms. In certain embodiments, the treating of the pain comprises managing the pain. In certain embodiments, the method is used to prevent or manage pelvic pain. In certain embodiments, the treating of the pelvic pain comprises managing pelvic pain.

In certain embodiments, the method is used to reduce the progression of the pain, and/or pain related symptoms, from a less severe state to a more severe state. In certain embodiments, the treating of the pain, and/or the pain related symptoms, associated with dysmenorrhea comprises reducing progression of pain, and/or pain related symptoms, from a less severe state to a more severe state.

In certain embodiments, the method is used to reduce the progression of pelvic pain from a less severe state to a more severe state. In certain embodiments, the treating of the pain associated with dysmenorrhea comprises reducing progression of pelvic pain from a less severe state to a more severe state.

In certain embodiments, the method is used to prevent or slow the transition to a pain condition in the subject. In certain embodiments, the treating of the pain comprises preventing or slowing the transition to a pain condition in the subject. In certain embodiments, the treating of the pain comprises preventing or slowing the transition to a chronic pain condition in the subject.

In certain embodiments, the method is used to provide an early intervention in a subject presenting with pain, and/or pain related symptoms, associated with dysmenorrhea. In certain embodiments, the method is used to provide an early intervention in a subject presenting with distressing or severe dysmenorrhea.

In certain embodiments, the method is used to prevent the development of central sensitisation of pain in a subject.

In certain embodiments, the method is used to prevent the development of peripheral sensitisation of nociceptors within the uterus of a subject.

The term "intravaginal and/or vaginal administration" as used herein refers to administration of an agent by way of the way of the uterus, the cervix, the cervical canal and/or the vagina, (see for example FIG. 1).

In certain embodiments, the administration of the agent that reduces activation of the innate immune system comprises intrauterine administration. In certain embodiments, the administration of the agent that reduces activation of the innate immune system comprises vaginal administration.

The term "effective amount" as used herein refers to that amount of an agent that is sufficient to effect treatment, when administered to a subject. The effective amount will vary depending upon a number of factors, including for example the specific activity of the agent being used, the severity of the condition, the subject, the age, physical condition, existence of other disease states, nutritional status of the subject and genetic background of the subject.

In this regard, it has been found that the effective dose for treatment of pain with agents that reduce activation of the innate system by intrauterine/vaginal administration is markedly lower than would have been anticipated from studies using other administration routes, such as oral administration. For example, it was found that amitriptyline is effective in a mouse model at reducing spinal glial activation at a dose of 27 µg/kg, and that TAK242 is effective at a concentration of 36 µg/kg.

The lower effective dose required to achieve treatment of pain (and/or pain related symptoms) is desirable, as some agents carry significant side effects at higher doses. For example, amitriptyline is a known drug with extensive use over decades and a known safety profile, but which still has a number of side effects: When taken orally, amitriptyline has side effects such as drowsiness, dry mouth, blurred vision, pupil dilation, constipation, weight and urinary retention. Use of a lower dose obviates, or at least reduces, these side effects.

In certain embodiments, the agent is administered to the subject in an amount ranging from one of the following selected ranges: 1 µg/kg to 10 mg/kg; 1 µg/kg to 1 mg/kg; 1 µg/kg to 100 µg/kg; 1 µg/kg to 10 µg/kg; 10 µg/kg to 10 mg/kg; 10 µg/kg to 1 mg/kg; 10 µg/kg to 100 µg/kg; 100 µg/kg to 10 mg/kg; 100 µg/kg to 1 mg/kg; or 1 mg/kg to 10 mg/kg. Other ranges are contemplated.

In certain embodiments, the agent is administered to the subject in an amount ranging from one of the following selected ranges: 0.01 µg/kg/day to 10 mg/kg/day, 0.01 µg/kg/day to 1 mg/kg/day, 0.01 µg/kg/day to 100 µg/kg/day, 0.01 µg/kg/day to 10 µg/kg/day 0.01 µg/kg/day to 1 µg/kg/day, 0.01 µg/kg/day to 0.1 µg/kg/day, 0.1 µg/kg/day to 10 mg/kg/day, 0.1 µg/kg/day to 1 mg/kg/day, 0.1 µg/kg/day to 100 µg/kg/day, 0.1 µg/kg/day to 10 µg/kg/day 0.1 µg/kg/day to 1 µg/kg/day, 1 µg/kg/day to 10 mg/kg/day; 1 µg/kg/day to 1 mg/kg/day; 1 µg/kg/day to 100 µg/kg/day; 1 µg/kg/day to 10 µg/kg/day; 10 µg/kg/day to 10 mg/kg/day; 10 µg/kg/day to 1 mg/kg/day; 10 µg/kg/day to 100 µg/kg/day; 100 µg/kg/day to 10 mg/kg/day; 100 µg/kg/day to 1 mg/kg/day; or 1 mg/kg/day to 10 mg/kg/day. Other ranges are contemplated.

In certain embodiments, the method comprises administration to the subject of a dose of the agent that reduces activation of the innate immune system of less than 100 µg/kg. In certain embodiments, the method comprises administration to the subject of a dose of the agent that reduces activation of the innate immune system of less than 70 µg/kg. In certain embodiments, the method comprises administration to the subject of a dose of the agent that reduces activation of the innate immune system of less than 50 µg/kg. In certain embodiments, the method comprises administration to the subject of a dose of the agent that reduces activation of the innate immune system of less than 25 µg/kg. In certain embodiments, the method comprises administration to the subject of a dose of the agent that reduces activation of the innate immune system of less than 10 µg/kg.

In certain embodiments, the method comprises administration to the subject of a dose of the agent that reduces activation of the innate immune system of less than 100 µg/kg/day. In certain embodiments, the method comprises administration to the subject of a dose of the agent that reduces activation of the innate immune system of less than 70 µg/kg/day. In certain embodiments, the method comprises administration to the subject of a dose of the agent that reduces activation of the innate immune system of less than 50 µg/kg/day. In certain embodiments, the method comprises administration to the subject of a dose of the agent that reduces activation of the innate immune system of less than 25 µg/kg/day. In certain embodiments, the method comprises administration to the subject of a dose of the agent that reduces activation of the innate immune system of less than 10 µg/kg/day.

In certain embodiments, the agent is a TLR4 inhibitor or antagonist, and the agent is administered in an amount from 10 µg/kg to 100 µg/kg, or 10 µg/kg to 50 µg/kg. In certain embodiments, the agent is a TLR4 inhibitor or antagonist, and the agent is administered in an amount from 10 µg/kg/day to 100 µg/kg/day or 10 µg/kg/day to 50 µg/kg/day. Other ranges are contemplated.

In certain embodiments, the method comprises administration to the subject of a TLR4 inhibitor or antagonist at a dose of less than 100 µg/kg, less than 70 µg/kg, less than 50 µg/kg, less than 25 µg/kg, or less than 10 µg/kg.

In certain embodiments, the method comprises administration to the subject of a TLR4 inhibitor or antagonist at a dose of less than 100 µg/kg/day, less than 70 µg/kg/day, less than 50 µg/kg/day, less than 25 µg/kg/day, or less than 10 µg/kg/day.

In certain embodiments, the present disclosure provides a method of reducing pain, and/or pain related symptoms, associated with dysmenorrhea in a subject, the method comprising intrauterine and/or vaginal administration to the subject of an effective amount of an agent that reduces activation of the innate immune system and thereby reducing the pain and/or the pain related symptoms in the subject.

In certain embodiments, the present disclosure provides a method of reducing pain, and/or pain related symptoms, associated with dysmenorrhea in a subject, the method comprising intrauterine and/or vaginal administration to the subject of an effective amount of amitriptyline and thereby reducing the pain and/or the pain related symptoms in the subject.

In certain embodiments, the present disclosure provides a method of reducing pain, and/or pain related symptoms, associated with dysmenorrhea in a subject, the method comprising intrauterine and/or vaginal administration to the subject of an effective amount of nortriptyline and thereby reducing the pain and/or the pain related symptoms in the subject.

In certain embodiments, the present disclosure provides a method of reducing pain, and/or pain related symptoms, associated with dysmenorrhea in a subject, the method comprising intrauterine and/or vaginal administration to the subject of an effective amount of TAK242 and thereby reducing the pain and/or the pain related symptoms in the subject.

In certain embodiments, the present disclosure provides a low dose method of treating pain, and/or pain related symptoms, associated with dysmenorrhea in a subject, the method comprising intrauterine and/or vaginal administration to the subject of an effective amount of an agent that reduces activation of the innate immune system and thereby treating the pain and/or the pain related symptoms in the subject.

In certain embodiments, the present disclosure provides a low dose method of treating pain, and/or pain related symptoms, associated with dysmenorrhea in a subject, the method comprising intrauterine and/or vaginal administration to the subject of an effective amount of amitriptyline and thereby treating the pain and/or the pain related symptoms in the subject.

In certain embodiments, the present disclosure provides a low dose method of treating pain, and/or pain related symptoms, associated with dysmenorrhea in a subject, the method comprising intrauterine and/or vaginal administration to the subject of an effective amount of nortriptyline and thereby treating the pain and/or the pain related symptoms in the subject.

In certain embodiments, the method of treatment provides a form of treatment that avoids or reduces the need for treatment with opioid medication and/or reduces the development of tolerance to opioid medications. In this regard, another option for management of pain, and/or pain related symptoms, associated with dysmenorrhea involves the use of regular opioid medications. However, in some women this is associated with the development of opioid-induced hyperalgesia resulting in an increase in pain, or the development of opioid medication tolerance, which are recognised as major public health issues.

The agent may be administered to the subject in a suitable form. In this regard, the term "administering" as used herein includes administering the agent, or administering a prodrug, or a derivative that will form an effective amount of the agent at the site of action. The terms include various types of administration forms such as liquid compositions, semi-solid compositions, suppositories, gels, solids, tablets, capsules, creams, solutions, pastes, ointments, implants or by way of a release from a device. Other administration forms are contemplated.

Methods for intrauterine or vaginal administration of agents generally are as described, for example, in Sahoo et al (2013) *American Journal of Advanced Drug Delivery*: ISSN-2321-547X, Bhowmik et al (2010) *Annals of Biological Research* 1(1): 70-75, and Widermeesch D. (2010) *Hand. Exp Pharmacol.* 197: 268-298.

The agent may be administered alone or may be delivered in a mixture with other therapeutic agents and/or agents that, for example, enhance, stabilise or maintain the activity of the agent, such as a non-steroidal anti-inflammatory agent. Examples of non-steroidal inflammatory agents include naprosyn or diclofenac.

In this regard, the subject may be treated or given another drug or treatment modality in conjunction with the agent as described herein. It will be appreciated that the administration of another drug need not be intrauterinally and/or vaginally, but may also be by other administration routes such as orally, intravenously, by injection, peritoneally, by implant, or by way of suppository. Examples include levonorgestrel, or an anti-inflammatory agent such as naprosyn or diclofenac.

Combination therapy with other agents can be sequential therapy where the subject is treated first with one and then the other, or the two or more treatment modalities are given simultaneously. For example, two or more therapeutic agents can be co-formulated into a single dosage form or "combined dosage unit", or formulated separately and subsequently combined into a combined dosage unit.

When administered to a subject the effective dosage of a therapeutic agent may vary depending upon the particular agent utilized, the mode of administration, the condition, and severity thereof, as well as the various physical factors related to the subject being treated. Dosages are expected to vary with the delivery route, and the nature of the therapeutic agent being administered and other agents administered.

In certain embodiments, the administering to the subject comprises a dose of the agent administered on a regular basis, such as twice daily, daily, weekly, monthly, annually, or multi-annually.

In certain embodiments, the administering to the subject comprises continuous administering to the subject of the agent. In certain embodiments, the administering to the subject comprises escalating doses of the agent and/or repeated doses.

In certain embodiments, the administering to the subject comprises long-term administration of the agent to the subject. In certain embodiments, the administering to the subject comprises long-term continuous administration of the agent to the subject.

In certain embodiments, the agent that reduces activation of an innate immune system is administered as an immediate release formulation. The term "immediate release formulation" as used herein is a formulation designed to quickly release an agent in the body over a shortened period of time. Immediate release formulations are known in the art.

In certain embodiments, the agent that reduces activation of the innate immune system is administered as a slow release/sustained release formulation. The term "sustained release formulation" as used herein is a formulation designed to slowly release an agent in the body over an extended period of time. Sustained release formulations are known in the art.

In certain embodiments, the agent that reduces activation of the innate immune system is administered by way of release from a composition. In certain embodiments, the agent that reduces activation of the innate immune system is administered by way of release from a substrate. In certain embodiments, the agent that reduces activation of the innate immune system is administered by way of release through a membrane.

In certain embodiments, the agent that reduces activation of the innate immune system is administered by way of release from a device.

In certain embodiments, the administering of the agent that reduces activation of the innate immune system to the subject is dependent upon timing of the menstrual cycle. In certain embodiments, the administering of the agent that reduces activation of the innate immune system to the subject coincides with the timing of the menstrual cycle.

In certain embodiments, the agent that reduces activation of the innate immune system is administered to the subject in a composition suitable for intrauterine and/or vaginal administration, as described herein.

In certain embodiments, the agent that reduces activation of the innate immune system is administered to the subject via a liquid composition, a semi-solid composition, a gel, a solid, a suppository, a tablet, a capsule, a cream, a solution, a paste, or an ointment. Other compositional forms are contemplated.

In certain embodiments, the agent that reduces 1 activation of the innate immune system is administered to the subject from a device suitable for local pelvic administration.

In certain embodiments, the administration comprises release from a device. In certain embodiments, the administration comprises release from an intrauterine device. In certain embodiments, the administration comprises release from a vaginal device.

Devices for local pelvic administration of agents are known in the art. Examples of devices include, for example, devices sold under the brand name "Mirena", vaginal rings, coils, medicated tampons, vaginal suppositories and vaginal or uterine films. Devices are described, for example, in Bandyopadhyay A. K. (2008), Novel drug delivery systems, 1st edition, Everest publishing house, p. 215-220; Keshwani Bhawana & Arora Pankaj (2014) *Journal of Pharma Research*, 3 (10) 184-187; and Chatterjee Arkendu & Kumar Lalit (2009) *Journal of Pharmacy Research*, 2 (4) 698-700. 3 Mar. 15.

Substrates for use in devices for delivery of active agents are known in the art, and include for example, copolymers of di-methylsiloxanes and methylvinylsiloxanes, ethylene/vinyl acetate copolymers (EVA), polyethylene, polypropylene, ethylene/propylene copolymers, acrylic acid polymers, ethylene/ethyl acrylate copolymers, polytetrafluoroethylene (PTFE), polyurethanes, thermoplastic polyurethanes and polyurethane elastomers, polybutadiene, polyisoprene, poly (methacrylate), polymethyl methacrylate, styrene-butadiene-styrene block copolymers, poly(hydroxyethyl-methacrylate) (pHEMA), polyvinyl chloride, polyvinyl acetate, polyethers, polyacrylo-nitriles, polyethylene glycols, polymethylpentene, polybutadiene, polyhydroxy alkanoates, poly(lactic acid), poly(glycolic acid), polyanhydrides, polyorthoesters, hydrophilic polymers such as the hydrophilic hydrogels, cross-linked polyvinyl alcohol, neoprene rubber, butyl rubber, hydroxyl-terminated organopolysiloxanes, and copolymers of the aforementioned. Methods for incorporating active agents into a substrate for local pelvic release are known in the art.

In certain embodiments, the method further provides administering a sex hormone and/or an agent that modulates production and/or activity of a sex hormone directly or indirectly, such as a GnRH antagonist. The administering may be intrauterine and/or vaginally, or may utilise another route of administration such as oral administration or a non-oral administration.

Sex hormones and/or an agents that modulate production and/or activity of a sex hormone may be natural or synthetic agents, and includes for example steroids such as gonadocorticoids, agents that interact with estrogen, progesterone or androgen receptors such as selective estrogen receptor modulators (SERM), selective progesterone receptor modulators (SPRM), selective androgen receptor modulators (SARM), and/or other agents that have the ability to modulate activity associated with a sex hormone.

In certain embodiments, the method further comprises local pelvic administration to the subject of a sex hormone and/or an agent that modulates production and/or activity of a sex hormone, such as an estrogen, a progestogen, an androgen, a SERM, a SPRM and/or a SARM. A suitable dose and treatment regime may be selected. In certain embodiments, the method further comprises intrauterine and/or vaginal administration of a sex hormone and/or an agent that modulates production and/or activity of a sex hormone.

In certain embodiments, the sex hormone comprises an estrogen and/or a progestogen. In certain embodiments, the sex hormone comprises an androgen.

Examples of estrogen compounds include steroidal and non-steroidal estrogen compounds. Examples of progestogen compounds include one or more of the following compounds: progesterone and its derivatives, dienogest, cyproterone acetate, desogestrel, etonogestrel, levonorgestrel, lynestrenol, medroxyprogesterone acetate, norethisterone, norethisterone acetate, norgestimate, drospirenone, gestodene, 19-nor-17-hydroxy progesterone esters, 17α-ethinyltestosterone and derivatives thereof, 17α-ethinyl-19-nor-testosterone and derivatives thereof, ethynodiol diacetate, dydrogesterone, norethynodrel, allylestrenol, medrogestone, norgestrienone, ethisterone and dl-norgestrel.

In certain embodiments, the progestogen comprises one or more of levonorgestrel, dienogest, and a GnRH antagonist.

Examples of androgen compounds include steroidal and non-steroidal androgen compounds.

In certain embodiments, the sex hormone and/or the agent that modulates production and/or activity of a sex hormone is administered to the subject via the same administration route as the agent that reduces spinal glial activation.

In certain embodiments, the sex hormone and/or the agent that modulates production and/or activity of a sex hormone is administered by local pelvic administration. In certain embodiments, the sex hormone and/or the agent that modulates production and/or activity of a sex hormone is administered by way of a composition suitable for local pelvic administration. In certain embodiments, the sex hormone and/or the agent that modulates production and/or activity of a sex hormone is administered by way of an intrauterine composition and/or a vaginal composition. Compositions are as described herein.

In certain embodiments, the sex hormone and/or the agent that modulates production and/or activity of a sex hormone is administered to the subject by way of release from a pelvic device. In certain embodiments, the sex hormone and/or the agent that modulates production and/or activity of a sex hormone is administered to the subject by way of release from an intrauterine device and/or a vaginal device. Devices are as described herein.

In certain embodiments, the device provides long term release of a sex hormone and/or the agent that modulates production and/or activity of a sex hormone. In certain embodiments, the device provides long term continuous release of a sex hormone and/or the agent that modulates production and/or activity of a sex hormone.

Certain embodiments of the present disclosure provide a composition comprising an effective amount of an agent that reduces activation of the innate immune system for intrauterine and/or vaginal administration for a use as described herein.

In certain embodiments, the present disclosure provides a composition for intrauterine and/or vaginal administration for treating pain, and/or pain related symptoms, associated with dysmenorrhea in a subject, the composition comprising an agent that reduces activation of the innate immune system.

Compositions for intrauterine and/or vaginal administration are as described herein.

Agents that reduce activation of the innate immune system are as described herein.

In certain embodiments, the agent that reduces activation of the innate immune system comprises a pattern recognition receptor inhibitor, as described herein.

In certain embodiments, the agent that reduces activation of the innate immune system comprises an agent that reduces activation of spinal glial cells.

In certain embodiments, the agent that reduces activation of the innate immune system comprises an inhibitor of a Toll-like receptor (TLR), a C-type lectin receptor (CLR), a NOD-like receptor (NDR), a RIG-1-like receptor (RIG-1 receptor) and/or an MDA-5 receptor.

In certain embodiments, the agent that reduces activation of the innate immune system comprises an inhibitor of one or more of TLR2, TLR3, TLR4, TLR5, TLR8, TLR9, Dectin-1a, Dectin-1b, Mincle, NOD-1, NOD-2, RIG-1 and MDA-5.

In certain embodiments, the agent that reduces activation of the innate immune system comprises a TLR inhibitor or antagonist.

In certain embodiments, the agent that reduces activation of the innate system comprises a TLR4 inhibitor or antagonist. In certain embodiments, the TLR4 antagonist comprises one or more of the following: Eritoran, Amitriptyline, Nortriptyline, Cyclobenzaprine, Ketotifen, Imipramine, Mianserin, Ibudilast, Pinocembrin, (+) Naltrexone, (−) Naltrexone, (+) Naloxone, (−) Naloxone, minocycline, LPS-RS, Propentofylline and (+)-naloxone, 1J, TAK-242, Desipramine, Carbamazepine, Oxcarbazepine, Rimcazole, Mesoridazine, Tacrine, Orphenadrine, Diphenhydramine, Duloxetine, Venlafaxine, Chlorpromazine, Fluoxetine, curcumin, an effective cannabinoid, Lipid A mimetic, SPA4, STM28, xanthohumal, JTT-705, auranofin, sulforaphane, cinnamaldehyde, taxanes, 6-shogaol, soliquiritigenin, OSL07, glycyrrhizin, isoliquiritigenin, caffeic acid phenethyl ester, IAXO-101, T5342126, KRGISPGGGSDAQ-GEV, morphine, NCI126224, paclitaxel, heme, chitohexaose, compounds 12 to 18, 22, and 29 to 33 as described in Wang et al (2013) *Chem Soc Rev.* 42(12): 4859-4866, and/or a prodrug or metabolite of any one or more of the aforementioned.

In certain embodiments, the agent that reduces activation of the innate immune system comprises amitriptyline.

In certain embodiments, the agent that reduces activation of the innate immune system comprises nortriptyline.

In certain embodiments, the agent that reduces activation of the innate immune system comprises TAK242.

In certain embodiments, the agent that reduces activation of the innate immune system comprises a TLR2 inhibitor or antagonist. In certain embodiments, the TLR2 antagonist comprises one or more of the following: a tricyclic such as amitriptyline, CU-CPT22, Sparstolonin B, and sulphoglycolipids, compounds 12 to 18, 22, and 29 to 33 as described in Wang et al (2013) *Chem Soc Rev.* 42(12): 4859-4866, and/or a prodrug or metabolite of one or more of the aforementioned.

In certain embodiments, the present disclosure provides a composition for intrauterine and/or vaginal administration for treating pain, and/or pain related symptoms, associated with dysmenorrhea in a subject, the composition comprising amitriptyline.

In certain embodiments, the present disclosure provides a composition for intrauterine and/or vaginal administration for treating pain, and/or pain related symptoms, associated with dysmenorrhea in a subject, the composition comprising nortriptyline.

In certain embodiments, the present disclosure provides a composition for intrauterine and/or vaginal administration for treating pain, and/or pain related symptoms, associated with dysmenorrhea in a subject, the composition comprising TAK242.

In certain embodiments, the composition comprises a liquid composition, a semi-solid composition, a suppository, a gel, a solid, a tablet, a capsule, a cream, a solution, a paste, or an ointment. In certain embodiments, the composition comprises a substrate with a releasable agent that reduces spinal glial activation.

Compositions for intrauterine and/or vaginal administration are known in the art, for example as described in Sahoo et al (2013) *American Journal of Advanced Drug Delivery:* ISSN-2321-547X.

Additional numerous various excipients, dosage forms, dispersing agents and the like that are suitable for use in connection with administration and/or the formulation into medicaments or compositions are known and described in, for example, Remington's Pharmaceutical Sciences, 17th ed., Mack Publishing Company, Easton, Pa., 1985, which is incorporated herein by reference in its entirety. Methods for formulating compositions are known in the art.

A suitable dosage of the agent that reduces activation of the innate immune system in the composition may be selected. In certain embodiments, the composition comprises the agent that reduces spinal glial activation in an amount ranging from 10 µg to 500 mg, 10 µg to 100 mg, 10 µg to 10 mg, 10 µg to 1 mg, 10 µg to 100 µg, 100 µg to 500 mg, 100 µg to 100 mg; 100 µg to 10 mg; 100 µg to 1 mg, 1 mg to 500 mg 1 mg to 100 mg, or 1 mg to 10 mg. Other ranges are contemplated. Other amounts are contemplated.

In certain embodiments, the composition comprises the agent that reduces activation of the innate immune system in an amount to provide a dose ranging from one of the following selected ranges: 0.1 µg/kg to 10 mg/kg; 0.1 µg/kg to 1 mg/kg; 0.1 µg/kg to 100 µg/kg; 0.1 µg/kg to 10 µg/kg; 1 µg/kg to 10 mg/kg; 1 µg/kg to 1 mg/kg; 1 µg/kg to 100 µg/kg; 1 µg/kg to 10 µg/kg; 10 µg/kg to 10 mg/kg; 10 µg/kg to 1 mg/kg; 10 µg/kg to 100 µg/kg; 100 µg/kg to 10 mg/kg; 100 µg/kg to 1 mg/kg; or 1 mg/kg to 10 mg/kg. Other ranges are contemplated.

In certain embodiments, the composition comprises the agent that reduces activation of the innate immune system in an amount to provide a dose ranging from one of the following selected ranges: 0.01 µg/kg/day to 10 mg/kg/day, 0.01 µg/kg/day to 1 mg/kg/day, 0.01 µg/kg/day to 100 µg/kg/day, 0.01 µg/kg/day to 10 µg/kg/day 0.01 µg/kg/day to 1 µg/kg/day, 0.01 µg/kg/day to 0.1 µg/kg/day, 0.1 µg/kg/day to 10 mg/kg/day; 0.1 µg/kg/day to 1 mg/kg/day; 0.1 µg/kg/day to 100 µg/kg/day; 0.1 µg/kg/day to 10 µg/kg/day; 1 µg/kg/day to 10 mg/kg/day; 1 µg/kg/day to 1 mg/kg/day; 1 µg/kg/day to 100 µg/kg/day; 1 µg/kg/day to 10 µg/kg/day; 10 µg/kg/day to 10 mg/kg/day; 10 µg/kg/day to 1 mg/kg/day; 10 µg/kg/day to 100 µg/kg/day; 100 µg/kg/day to 10 mg/kg/day; 100 µg/kg/day to 1 mg/kg/day; or 1 mg/kg/day to 10 mg/kg/day. Other ranges are contemplated.

In certain embodiments, the composition comprises the agent that reduces activation of the innate immune system in an amount to provide a dose of the agent of less than 100 µg/kg. In certain embodiments, the composition comprises the agent that reduces activation of the innate immune system in an amount to provide a dose of less than 70 µg/kg. In certain embodiments, the composition comprises the agent that reduces activation of the innate immune system in an amount to provide a dose of the agent less than 50 µg/kg. In certain embodiments, the composition comprises the agent that reduces activation of the innate immune system in an amount to provide a dose of the agent less than 25 µg/kg.

In certain embodiments, the composition comprises the agent that reduces activation of the innate immune system in an amount to provide a dose of the agent less than 10 µg/kg.

In certain embodiments, the composition comprises the agent that reduces activation of the innate immune system in an amount to provide a dose of the agent of less than 100 µg/kg/day. In certain embodiments, the composition comprises the agent that reduces activation of the innate immune system in an amount to provide a dose of the agent of less than 70 µg/kg/day. In certain embodiments, the composition comprises the agent that reduces activation of the innate immune system in an amount to provide a dose of less than 50 µg/kg/day. In certain embodiments, the composition comprises the agent that reduces activation of the innate immune system in an amount to provide a dose of less than 25 µg/kg/day. In certain embodiments, the composition comprises the agent that reduces activation of the innate immune system in an amount to provide a dose of less than 10 µg/kg/day.

In certain embodiments, the composition comprises an acceptable carrier suitable for administering the composition to a subject. The carrier may be chosen based on various considerations including the agent(s) being delivered and the time course of delivery of the agents. The term "acceptable carrier" as used herein refers to a substantially inert solid, semi-solid or liquid filler, diluent, excipient, encapsulating material or suitable auxiliary formulation. Physiologically acceptable carriers and their formulations are known in the art.

In certain embodiments, the composition is suitable for administering the agent that reduces glial activation of the innate immune system to the subject on a regular basis, such as twice daily, daily, weekly, monthly, annually or multi-annually administration.

In certain embodiments, the composition is suitable for continuous administration of the agent that reduces activation of the innate immune system to the subject.

In certain embodiments, the composition is an immediate release formulation.

In certain embodiments, the composition is a slow/sustained release formulation.

In certain embodiments, the composition provides long-term administration of the agent that reduces activation of the innate immune system. In certain embodiments, the composition provides long-term continuous administration of the agent that reduces activation of the innate immune system.

In certain embodiments, the composition comprises a solid substrate with a releasable form of the agent that reduces activation of the innate immune system.

Solid substrates suitable for releasing agents are as described herein.

In certain embodiments, the composition further comprises a sex hormone and/or an agent that modulates production or activity of a sex hormone. Examples of such agents are as described herein. A suitable dose may be selected.

In certain embodiments, the sex hormone comprises one or more of the following: progesterone and its derivatives, dienogest, cyproterone acetate, desogestrel, etonogestrel, levonorgestrel, lynestrenol, medroxyprogesterone acetate, norethisterone, norethisterone acetate, norgestimate, drospirenone, gestodene, 19-nor-17-hydroxy progesterone esters, 17α-ethinyltestosterone and derivatives thereof, 17α-ethinyl-19-nor-testosterone and derivatives thereof, ethynodiol diacetate, dydrogesterone, norethynodrel, allylestrenol, medrogestone, norgestrienone, ethisterone and dl-norgestrel. Other sex hormones are contemplated.

In certain embodiments, the sex hormone levonorgestrel.

In certain embodiments, the composition provides long-term release of the sex hormone and/or the agent that modulates production and/or activity of a sex hormone. In certain embodiments, the composition provides long-term continuous release of the sex hormone and/or the agent that modulates production and/or activity of a sex hormone.

In certain embodiments, the composition comprises a solid substrate with a releasable form of the sex hormone and/or the agent that modulates production and/or activity of a sex hormone.

In certain embodiments, the present disclosure provides a method of treating pain, and/or pain related symptoms, associated with dysmenorrhea in a subject by intrauterine and/or vaginal administration of a composition as described herein.

In certain embodiments, the present disclosure provides a product for treating pain, and/or pain related symptoms, associated with dysmenorrhea.

In certain embodiments, the present disclosure provides a combination product comprising an agent that reduces activation of the innate immune system.

In certain embodiments, the present disclosure provides a combination product comprising the following components: (i) an agent that reduces activation of the innate immune system; and (ii) a sex hormone and/or an agent that modulates production and/or activity of a sex hormone.

In certain embodiments, the present disclosure provides a combination product comprising the following components: (i) amitriptyline; and (ii) a sex hormone and/or an agent that modulates production and/or activity of a sex hormone.

In certain embodiments, the present disclosure provides a combination product comprising the following components: (i) nortriptyline; and (ii) a sex hormone and/or an agent that modulates production and/or activity of a sex hormone.

In certain embodiments, the present disclosure provides a combination product comprising the following components: (i) TAK242; and (ii) a sex hormone and/or an agent that modulates production and/or activity of a sex hormone.

In certain embodiments, the present disclosure provides a combination product comprising the following components: (i) an agent that reduces activation of the innate immune system; and (ii) a sex hormone and/or an agent that modulates production and/or activity of a sex hormone; wherein the components are suitable for separate or combined intrauterine and/or vaginal administration to a subject.

In certain embodiments, the present disclosure provides a combination product comprising the following components: (i) amitriptyline; and (ii) a sex hormone and/or an agent that modulates production and/or activity of a sex hormone; wherein the components are suitable for separate or combined intrauterine and/or vaginal administration to a subject.

In certain embodiments, the present disclosure provides a combination product comprising the following components: (i) nortriptyline; and (ii) a sex hormone and/or an agent that modulates production and/or activity of a sex hormone; wherein the components are suitable for separate or combined intrauterine and/or vaginal administration to a subject.

In certain embodiments, the present disclosure provides a combination product comprising the following components: (i) TAK242; and (ii) a sex hormone and/or an agent that modulates production and/or activity of a sex hormone; wherein the components are suitable for separate or combined intrauterine and/or vaginal administration to a subject.

In certain embodiments, the present disclosure provides a combination product comprising the following components: (i) a composition suitable for intrauterine and/or vaginal administration as described herein; and (ii) a composition suitable for administration comprising a sex hormone and/or an agent that modulates production and/or activity of a sex hormone.

Certain embodiments of the present disclosure provide an intrauterine or vaginal device.

In certain embodiments, the present disclosure provides an intrauterine or vaginal device comprising a releasable agent that reduces activation of the innate immune system.

Agents that reduce activation of the innate immune system are as described herein. In certain embodiments, the device is an intrauterine device. In certain embodiments, the device is a vaginal device.

Devices for administering agents are known in the art. Examples of devices include, for example, devices sold under the brand name "Mirena", "Kyleena" and "Skyla", vaginal rings, coils, medicated tampons, vaginal suppositories, and vaginal or uterine films. Devices are described, for example, in Bandyopadhyay A. K. (2008), Novel drug delivery system, 1st edition, Everest publishing house, p. 215-220, Keshwani Bhawana & Arora Pankaj (2014), Novel concepts in vaginal drug delivery, *Journal of Pharma Research*, 3 (10) 184-187, Chatterjee Arkendu & Kumar Lalit (2009), An overview of Intra-vaginal Drug delivery system, *Journal of Pharmacy Research*, 2 (4) 698-700. 3 Mar. 15.

Substrates for use in devices for release of active agents are known in the art, and include for example, copolymers of di-methylsiloxanes and methylvinylsiloxanes, ethylene/vinyl acetate copolymers (EVA), polyethylene, polypropylene, ethylene/propylene copolymers, acrylic acid polymers, ethylene/ethyl acrylate copolymers, polytetrafluoroethylene (PTFE), polyurethanes, thermoplastic polyurethanes and polyurethane elastomers, polybutadiene, polyisoprene, poly (methacrylate), polymethyl methacrylate, styrene-butadiene-styrene block copolymers, poly(hydroxyethyl-methacrylate) (pHEMA), polyvinyl chloride, polyvinyl acetate, polyethers, polyacrylo-nitriles, polyethylene glycols, polymethylpentene, polybutadiene, polyhydroxy alkanoates, poly(lactic acid), poly(glycolic acid), polyanhydrides, polyorthoesters, hydrophilic polymers such as the hydrophilic hydrogels, cross-linked polyvinyl alcohol, neoprene rubber, butyl rubber, hydroxyl-terminated organopolysiloxanes, and copolymers of the aforementioned. Methods for incorporating active agents into a substrate for release are known in the art.

In certain embodiments, the agent that reduces activation of the innate immune system comprises a pattern recognition receptor inhibitor, as described herein.

In certain embodiments, the agent that reduces activation of the innate immune system comprises an agent that reduces activation of spinal glial cells.

In certain embodiments, the agent that reduces activation of the innate immune system comprises an inhibitor of a Toll-like receptor (TLR), a C-type lectin receptor (CLR), a NOD-like receptor (NDR), a RIG-1-like receptor (RIG-1 receptor) and/or an MDA-5 receptor.

In certain embodiments, the agent that reduces activation of the innate immune system comprises an inhibitor of one or more of TLR2, TLR3, TLR4, TLR5, TLR8, TLR9, Dectin-1a, Dectin-1b, Mincle, NOD-1, NOD-2, RIG-1 and MDA-5.

In certain embodiments, the agent that reduces activation of the innate immune system comprises a TLR inhibitor or antagonist.

In certain embodiments, the agent that reduces spinal glial activation comprises a TLR4 inhibitor or antagonist. In certain embodiments, the TLR4 antagonist comprises one or more of the following: Eritoran, Amitriptyline, Nortriptyline, Cyclobenzaprine, Ketotifen, Imipramine, Mianserin, Ibudilast, Pinocembrin, (+) Naltrexone, (−) Naltrexone, (+) Naloxone, (−) Naloxone, minocycline, LPS-RS, Propentofylline and (+)-naloxone, 1J, TAK-242, Desipramine, Carbamazepine, Oxcarbazepine, Rimcazole, Mesoridazine, Tacrine, Orphenadrine, Diphenhydramine, Duloxetine, Venlafaxine, Chlorpromazine, Fluoxetine, curcumin, an effective cannabinoid, and compounds Lipid A mimetic, SPA4, STM28, xanthohumal, JTT-705, auranofin, sulforaphane, cinnamaldehyde, taxanes, 6-shogaol, soliquiritigenin, OSL07, glycyrrhizin, isoliquiritigenin, caffeic acid phenethyl ester, IAXO-101, T5342126, KRGISPGGGSDAQ-GEV, morphine, NCI126224, paclitaxel, heme, chitohexaose, compounds 12 to 18, 22, and 29 to 33 as described in Wang et al (2013) *Chem Soc Rev.* 42(12): 4859-4866), and/or a prodrug or metabolite of one or more of the aforementioned.

In certain embodiments, the agent that reduces spinal glial activation comprises amitriptyline.

In certain embodiments, the agent that reduces spinal glial activation comprises nortriptyline.

In certain embodiments, the agent that reduces spinal glial activation comprises TAK242.

In certain embodiments, the agent that reduces spinal glial activation comprises a TLR2 inhibitor or antagonist. In certain embodiments, the TLR2 antagonist comprises one or more of a tricyclic such as amitriptyline, CU-CPT22, Sparstolonin B, and sulphoglycolipids, compounds 12 to 18, 22, and 29 to 33 as described in Wang et al (2013) *Chem Soc Rev.* 42(12): 4859-4866, and/or a prodrug or metabolite of one or more of the aforementioned.

In certain embodiments, the present disclosure provides an intrauterine or vaginal device comprising releasable amitriptyline.

In certain embodiments, the present disclosure provides an intrauterine or vaginal device comprising releasable nortriptyline.

In certain embodiments, the present disclosure provides an intrauterine or vaginal device comprising releasable TAK242.

In certain embodiments, the device provides long-term release of the agent that reduces activation of the innate immune system.

In certain embodiments, the device comprises a membrane controlling release of the agent that reduces activation of the innate immune system.

In certain embodiments the device further comprises a releasable sex hormone and/or an agent that modulates production and/or activity of a sex hormone. Sex hormones and/or an agent that modulates production and/or activity of a sex hormone are as described herein.

In certain embodiments, the sex hormone comprises levonorgestrel.

In certain embodiments, the device provides long-term release of the sex hormone and/or an agent that modulates production and/or activity of a sex hormone. In certain embodiments, the device provides long-term continuous release of the sex hormone and/or an agent that modulates production and/or activity of a sex hormone.

In certain embodiments, the present disclosure provides an analgesic intrauterine or vaginal device comprising a releasable agent that reduces activation of the innate immune system.

Agents that reduce activation of the innate immune system are as described herein.

In certain embodiments, the agent that reduces activation of the innate immune system comprises a pattern recognition receptor inhibitor, as described herein.

In certain embodiments, the agent that reduces activation of the innate immune system comprises an agent that reduces activation of spinal glial cells.

In certain embodiments, the agent that reduces activation of the innate immune system comprises an inhibitor of a Toll-like receptor (TLR), a C-type lectin receptor (CLR), a NOD-like receptor (NDR), a RIG-1-like receptor (RIG-1 receptor) and/or an MDA-5 receptor.

In certain embodiments, the agent that reduces activation of the innate immune system comprises an inhibitor of one or more of TLR2, TLR3, TLR4, TLR5, TLR8, TLR9, Dectin-1a, Dectin-1b, Mincle, NOD-1, NOD-2, RIG-1 and MDA-5.

In certain embodiments, the present disclosure provides an analgesic intrauterine or vaginal device comprising releasable amitriptyline.

In certain embodiments, the present disclosure provides an analgesic intrauterine or vaginal device comprising releasable nortriptyline.

In certain embodiments, the present disclosure provides an analgesic intrauterine or vaginal device comprising releasable TAK242.

In certain embodiments, the present disclosure provides a method of treating pain, and/or paid related symptoms, associated with dysmenorrhea in a subject, the method comprising use of an intrauterine or vaginal device as described herein.

Certain embodiments of the present disclosure provide a solid substrate.

In certain embodiments, the present disclosure provides a solid substrate comprising a releasable agent that reduces activation of the innate immune system.

Agents that reduce activation of the innate immune system are as described herein.

In certain embodiments, the agent that reduces activation of the innate immune system comprises a pattern recognition receptor inhibitor, as described herein.

In certain embodiments, the agent that reduces activation of the innate immune system comprises an agent that reduces activation of spinal glial cells.

In certain embodiments, the agent that reduces activation of the innate immune system comprises an inhibitor of a Toll-like receptor (TLR), a C-type lectin receptor (CLR), a NOD-like receptor (NDR), a RIG-1-like receptor (RIG-1 receptor) and/or an MDA-5 receptor.

In certain embodiments, the agent that reduces activation of the innate immune system comprises an inhibitor of one or more of TLR2, TLR3, TLR4, TLR5, TLR8, TLR9, Dectin-1a, Dectin-1b, Mincle, NOD-1, NOD-2, RIG-1 and MDA-5.

Substrates suitable for use for releasing active agents are as described herein. Amounts of the agents are as described herein.

In certain embodiments, the present disclosure provides a solid substrate comprising releasable amitriptyline.

In certain embodiments, the present disclosure provides a solid substrate comprising releasable nortriptyline.

In certain embodiments, the present disclosure provides a solid substrate comprising releasable TAK242.

In certain embodiments, the present disclosure provides an intrauterine or vaginal device comprising a substrate as described herein.

Certain embodiments of the present disclosure provide a contraceptive intrauterine device comprising a releasable agent that reduces activation of the innate immune system. Contraceptive intrauterine devices are known in the art.

Agents that reduce activation of the innate immune system are as described herein.

In certain embodiments, the agent that reduces activation of the innate immune system comprises a pattern recognition receptor inhibitor, as described herein.

In certain embodiments, the agent that reduces activation of the innate immune system comprises an agent that reduces activation of spinal glial cells.

In certain embodiments, the agent that reduces activation of the innate immune system comprises an inhibitor of a Toll-like receptor (TLR), a C-type lectin receptor (CLR), a NOD-like receptor (NDR), a RIG-1-like receptor (RIG-1 receptor) and/or an MDA-5 receptor.

In certain embodiments, the agent that reduces activation of the innate immune system comprises an inhibitor of one or more of TLR2, TLR3, TLR4, TLR5, TLR8, TLR9, Dectin-1a, Dectin-1b, Mincle, NOD-1, NOD-2, RIG-1 and MDA-5.

In certain embodiments, the present disclosure provides a contraceptive intrauterine device comprising releasable amitriptyline.

In certain embodiments, the present disclosure provides a contraceptive intrauterine device comprising releasable nortriptyline.

In certain embodiments, the present disclosure provides a contraceptive intrauterine device comprising releasable TAK242.

Certain embodiments of the present disclosure provide a method of identifying or screening for new agents for treating pain, and/or pain related symptoms, associated with dysmenorrhea.

Agents so identified are potential therapeutic agents for treating pain, and/or pain related symptoms, associated with dysmenorrhea.

In certain embodiments, the present disclosure provides a method of identifying an agent for treating pain, and/or pain related symptoms, associated with dysmenorrhea, the method comprising determining the ability of a candidate agent that reduces activation of the innate immune system to treat pain, and/or pain related symptoms, associated with dysmenorrhea and thereby identifying the candidate agent that reduces activation of the innate immune system as an agent for treating pain, and/or pain related symptoms, associated with dysmenorrhea.

In certain embodiments, the candidate agent comprises a pattern recognition receptor inhibitor. Inhibitors are as described herein.

In certain embodiments, the candidate agent reduces activation of the innate immune system comprises an agent that reduces activation of spinal glial cells.

In certain embodiments, the candidate agent comprises an inhibitor of a Toll-like receptor (TLR), a C-type lectin receptor (CLR), a NOD-like receptor (NDR), a RIG-1-like receptor (RIG-1 receptor) and/or an MDA-5 receptor.

In certain embodiments, the candidate agent comprises an inhibitor of one or more of TLR2, TLR3, TLR4, TLR5, TLR8, TLR9, Dectin-1a, Dectin-1b, Mincle, NOD-1, NOD-2, RIG-1 and MDA-5.

In certain embodiments, the candidate agent comprises a TLR4 inhibitor and/or a TLR2 inhibitor.

Examples of candidate agents include a drug, a small molecule, a protein, a polypeptide, a lipid, a carbohydrate, a nucleic acid, an oligonucleotide, a ribozyme, a biologic, an aptamer, a cofactor, a ligand, a ligand mimetic, a receptor, a peptidomimetic, an enzyme, a kinase, a phosphatase, a cytokine, a growth factor, a metal ion, a chelate, an antisense nucleic acid, an inhibitor RNA, a microRNA, a siRNA, an antibody or antigen binding part thereof, an antibody mimetic. Other types of agents are contemplated.

Methods for determining the ability of an agent to reduce activation of the innate immune system are known in the art.

In certain embodiments, the method of identifying comprises use of in vitro studies and/or use of an animal model(s).

In certain embodiments, the present disclosure provides a kit for performing a method as described herein.

In certain embodiments, the present disclosure provides a kit for treating pain, and/or pain related symptoms, associated with dysmenorrhea, the kit comprising an agent that reduces activation of the innate immune system.

Agents that reduce activation of the innate immune system, and their use for treating pain, and/or pain related symptoms, associated with dysmenorrhea, are as described herein.

Certain embodiments of the present disclosure provide a method of reducing pain associated with the insertion and/or residency of an intrauterine device.

In this regard, it has been recognised that the pain associated with the insertion and/or residency of an intrauterine device is also likely due to the activation of the innate immune system, and as such agents as described herein may be used to reduce the pain.

In certain embodiments, the present disclosure provides a method of reducing pain associated with the insertion and/or residency of an intrauterine device, the method comprising intrauterine or vaginal administration to the subject of an agent that reduces activation of the innate immune system.

Agents that reduce activation of the innate immune system are as described herein.

In certain embodiments, the agent that reduces activation of the innate immune system comprises a pattern recognition receptor inhibitor. Pattern recognition receptor inhibitors are as described herein.

In certain embodiments, the agent that reduces activation of the innate immune system comprises a pattern recognition receptor inhibitor, as described herein.

In certain embodiments, the agent that reduces activation of the innate immune system comprises an agent that reduces activation of spinal glial cells.

In certain embodiments, the agent that reduces activation of the innate immune system comprises an inhibitor of a Toll-like receptor (TLR), a C-type lectin receptor (CLR), a NOD-like receptor (NDR), a RIG-1-like receptor (RIG-1 receptor) and/or an MDA-5 receptor.

In certain embodiments, the agent that reduces activation of the innate immune system comprises an inhibitor of one or more of TLR2, TLR3, TLR4, TLR5, TLR8, TLR9, Dectin-1a, Dectin-1b, Mincle, NOD-1, NOD-2, RIG-1 and MDA-5.

In certain embodiments, the agent that reduces activation of the innate immune system comprises a TLR inhibitor or antagonist.

In certain embodiments, the agent that reduces activation of the innate immune system comprises a TLR4 inhibitor or antagonist. In certain embodiments, the TLR4 antagonist comprises one or more Eritoran, Amitriptyline, Nortriptyline, Cyclobenzaprine, Ketotifen, Imipramine, Mianserin, Ibudilast, Pinocembrin, (+) Naltrexone, (−) Naltrexone, (+) Naloxone, (−) Naloxone, minocycline, LPS-RS, Propentofylline and (+)-naloxone, 1J, TAK-242, Desipramine, Carbamazepine, Oxcarbazepine, Rimcazole, Mesoridazine, Tacrine, Orphenadrine, Diphenhydramine, Duloxetine, Venlafaxine, Chlorpromazine, Fluoxetine, curcumin, an effective cannabinoid, and compounds Lipid A mimetic, SPA4, STM28, xanthohumal, JTT-705, auranofin, sulforaphane, cinnamaldehyde, taxanes, 6-shogaol, soliquiritigenin, OSL07, glycyrrhizin, isoliquiritigenin, caffeic acid phenethyl ester, IAXO-101, T5342126, KRGISPGGGSDAQ-GEV, morphine, NCI126224, paclitaxel, heme, chitohexaose, compounds 12 to 18, 22, and 29 to 33 as described in Wang et al (2013) *Chem Soc Rev.* 42(12): 4859-4866, and/or a prodrug or metabolite of any one or more of the aforementioned.

In certain embodiments, the agent that reduces activation of the innate immune system comprises amitriptyline.

In certain embodiments, the agent that reduces activation of the innate immune system comprises nortriptyline.

In certain embodiments, the agent that reduces activation of the innate immune system comprises TAK242.

In certain embodiments, the agent that reduces activation of the innate immune system comprises a TLR2 inhibitor or antagonist. In certain embodiments, the TLR2 antagonist comprises one or more of a tricyclic such as amitriptyline, CU-CPT22, Sparstolonin B, and sulphoglycolipids, compounds 12 to 18, 22, and 29 to 33 as described in Wang et al (2013) *Chem Soc Rev.* 42(12): 4859-4866, and/or a prodrug or metabolite of any one or more of the aforementioned.

In certain embodiments, the present disclosure provides a method of reducing pain associated with the insertion and/or residency of an intrauterine device, the method comprising intrauterine or vaginal administration to the subject of amitriptyline.

In certain embodiments, the present disclosure provides a method of reducing pain associated with the insertion and/or residency of an intrauterine device, the method comprising intrauterine or vaginal administration to the subject of nortriptyline.

In certain embodiments, the present disclosure provides a method of reducing pain associated with the insertion and/or residency of an intrauterine device, the method comprising intrauterine or vaginal administration to the subject of TAK242.

In certain embodiments, the method is used to reduce the rate of premature removal of the device from a subject.

Certain embodiments of the present disclosure provide a method of reducing activation of spinal glial cells in a subject.

In certain embodiments, the present disclosure provides a method of reducing activation of spinal glial cells in a subject, the method comprising intrauterine and/or vaginal administration to the subject of an effective amount of a pattern recognition receptor inhibitor and thereby reducing activation of the spinal glial cells in the subject.

In certain embodiments, the method prevents activation of spinal glial cells.

In certain embodiments, the spinal glial cells comprise astrocytes. In certain embodiments, the spinal glial cells comprise microglial cells.

In certain embodiments, the pattern recognition receptor inhibitor comprises an inhibitor of a Toll-like receptor (TLR), a C-type lectin receptor (CLR), a NOD-like receptor (NDR), a RIG-1-like receptor (RIG-1 receptor) and/or an MDA-5 receptor.

In certain embodiments, the pattern recognition receptor inhibitor comprises an inhibitor of one or more of TLR2, TLR3, TLR4, TLR5, TLR8, TLR9, Dectin-1a, Dectin-b, Mincle, NOD-1, NOD-2, RIG-1 and MDA-5.

In certain embodiments, the pattern recognition receptor inhibitor comprises an agent that inhibits a Toll-like receptor.

In certain embodiment, the pattern recognition receptor inhibitor is a selective inhibitor. In certain embodiments, the inhibitor is a non-selective inhibitor.

In certain embodiment, the pattern recognition receptor inhibitor comprises an antagonist. In certain embodiments, the antagonist is a selective antagonist. In certain embodiments, the antagonist is a non-selective antagonist.

In certain embodiments, the pattern recognition receptor inhibitor comprises a TLR4 inhibitor. In certain embodiments, the TLR4 inhibitor is a selective inhibitor. In certain embodiments, the TLR4 inhibitor is a non-selective inhibitor.

In certain embodiments, the pattern recognition receptor inhibitor comprises a TLR4 antagonist. In certain embodiments, the TLR4 antagonist is a selective antagonist. In certain embodiments, the TLR4 antagonist is a non-selective antagonist.

Examples of TLR4 inhibitors or antagonists include one or more of Eritoran, Amitriptyline (for example available from Mylan Pharmaceuticals Inc, USA), Nortriptyline (for example available from Centaur Pharmaceuticals), Cyclobenzaprine (for example available from Jubilant Life Sciences), Ketotifen (for example available from Sifavitor), Imipramine (for example available from H. Lundbeck AS), Mianserin (for example available from Albany Molecular Research Inc.), Ibudilast (for example available from Sanyo Chemical Laboratory Ltd), Pinocembrin, (+) Naltrexone, (−) Naltrexone, (+) Naloxone, (−) Naloxone, minocycline (for example available from Albany Molecular Research Inc.), LPS-RS, Propentofylline (for example Labratorio Chimico Internazionale Spa) and (+)-naloxone, 1J, TAK-242, Desipramine (for example available from H. Lundbeck AS), Carbamazepine (for example available from SAFC, Sigma-Aldrich Corporation) Oxcarbazepine (for example available from Albany Molecular Research Inc.), Rimcazole, Mesoridazine (for example available from Sumika Fine Chemicals Co Ltd), Tacrine (for example available from Nordic Syhtnesis AB), Orphenadrine (for example available from Kores India Limited), Diphenhydramine (for example available from Cadila Pharmaceuticals Limited, Duloxetine (for example available from BOC Sciences), Venlafaxine (for example available from Macleods Pharmaceuticals Limited), Chlorpromazine (for example available from Egis Pharmaceuticals PLC), Fluoxetine (for example available from PRONOVA BIOPHARMA NORGE AS), curcumin, an effective cannabinoid, and compounds Lipid A mimetic, SPA4, STM28, xanthohumal, JTT-705, auranofin, sulforaphane, cinnamaldehyde, taxanes, 6-shogaol, soliquiritigenin, OSL07, glycyrrhizin, isoliquiritigenin, caffeic acid phenethyl ester, IAXO-101, T5342126, KRGISPGGGS-DAQGEV, morphine, NCI126224, paclitaxel, heme, chitohexaose, compounds 12 to 18, 22, and 29 to 33 as described in Wang et al (2013) Chem Soc Rev. 42(12): 4859-4866.

In certain embodiments, the pattern recognition receptor inhibitor comprises amitriptyline.

In certain embodiments, the pattern recognition receptor inhibitor comprises nortriptyline.

In certain embodiments, the pattern recognition inhibitor comprises TAK242.

In certain embodiments, the pattern recognition receptor inhibitor comprises a TLR2 inhibitor. In certain embodiments, the TLR2 inhibitor is a selective inhibitor. In certain embodiments, the TLR2 inhibitor is a non-selective inhibitor.

In certain embodiments, the pattern recognition receptor inhibitor comprises a TLR2 antagonist. In certain embodiments, the TLR2 antagonist is a selective antagonist. In certain embodiments, the TLR2 antagonist is a non-selective antagonist.

TLR2 inhibitors and antagonists are known, and are commercially available or may be produced by a method known in the art. Examples of TLR2 inhibitors or antagonists include one or more of tricyclics including amitriptyline (for example available from Mylan Pharmaceuticals Inc, USA), and agents such as CU-CPT22 (for example available from Calbiochem), Sparstolonin B (available from Sigma Aldrich), and sulphoglycolipids, and compounds 1 to 5 as described in Wang et al (2013) Chem Soc Rev. 42(12): 4859-4866. Methods for determining whether an agent is a TLR2 inhibitor or antagonist are known in the art, for example as described in Cheng, K., et al. 2012. *Angew. Chem. Int. Ed.* 51, 12246.

In certain embodiments, the TLR2 inhibitor or antagonist comprises a small molecule. In certain embodiments the TLR2 inhibitor or antagonist comprises an antibody and/or an antigen binding part thereof. In certain embodiments the TLR2 inhibitor or antagonist comprises a nucleic acid.

In certain embodiments, the inhibitor or antagonist is both a TLR2 inhibitor or antagonist and a TLR4 inhibitor or antagonist.

In certain embodiments, the pattern recognition receptor inhibitor comprises one or more of a TLR4 inhibitor, a TLR2 inhibitor, minocycline, fluorocitrate, and propentofylline.

In certain embodiments, the present disclosure provides a method of reducing activation of spinal glial cells in a subject, the method comprising intrauterine and/or vaginal administration to the subject of an effective amount of amitriptyline and thereby reducing activation of the spinal glial cells in the subject.

In certain embodiments, the present disclosure provides a method of reducing activation of spinal glial cells in a subject, the method comprising intrauterine and/or vaginal administration to the subject of an effective amount of nortriptyline and thereby reducing activation of the spinal glial cells in the subject.

In certain embodiments, the present disclosure provides a method of reducing activation of spinal glial cells in a subject, the method comprising intrauterine and/or vaginal administration to the subject of an effective amount of TAK242.

Methods for administration of agents are as described herein. In certain embodiments, the administration comprises use of a device as described herein.

In certain embodiments, the subject is suffering from pain, and/or pain related symptoms, associated with dysmenorrhea. In certain embodiments, the subject is susceptible to developing pain, and/or pain related symptoms, associated with dysmenorrhea.

In certain embodiments, the subject is suffering from pelvic pain associated with dysmenorrhea. In certain embodiments, the subject is susceptible to developing pelvic pain associated with dysmenorrhea.

In certain embodiments, the subject is susceptible to progression of pain, and/or pain related symptoms, from a less severe state to a more severe state. In certain embodiments, the subject is susceptible to progression of pelvic pain from a less severe state to a more severe state.

In certain embodiments, the subject is susceptible to developing pain, and/or pain related symptoms, associated with the insertion and/or residency of an intrauterine device. In certain embodiments, the subject is susceptible to developing pelvic pain associated with the insertion and/or residency of an intrauterine device.

Certain embodiments of the present disclosure provide use of a pattern recognition receptor inhibitor for reducing activation of spinal glial cells in a subject.

The present disclosure is further described by the following examples. It is to be understood that the following description is for the purpose of describing particular embodiments only and is not intended to be limiting with respect to the above description.

Example 1—Women with and without Endometriosis Present with Similar Pain Profiles A clinical audit of 168 women with pelvic pain, where dysmenorrhea was a symptom, was performed. Women completed a questionnaire, which enquired as to the presence or absence of 14 additional symptoms. These symptoms included bladder pain, stabbing pain, bowel symptoms, food intolerance, headache, vulval pain, dyspareunia (pain with intercourse), fatigue, poor sleep, nausea, dizziness, and sweating. These women were further divided into 3 groups: those where endometriosis had been confirmed at laparoscopy (Endo+), those where endometriosis had been excluded at laparoscopy (Endo−), and those where no laparoscopy had been performed and no diagnosis could be made (No Lap). The frequency of each symptom was compared across the three groups. The results are shown in Table 1.

Example 2—Glial Activation of Mice Spinal Cord by Intra-Uterine Administration of Lipopolysaccharide, and Effect Modification by Intra-Uterine Administration of Toll-Like Receptor Modulators Introduction Severe dysmenorrhea in young women is an under-researched area of human need. Current treatment includes the use of hormonal menstrual suppression or the use of non-steroidal anti-inflammatory medications. Both treatment options may be inadequate, unacceptable or associated with adverse effects in some women. For this reason, alternative and improved treatment options are required.

In a study of one thousand girls aged 16-18 years, ninety three percent of girls experienced some pain with menstruation (dysmenorrhea). However, 21% suffered pain resulting in absenteeism from work and school. Anecdotally, many women with severe dysmenorrhea will progress to a chronic pelvic pain condition with additional pain and non-pain symptoms such as an irritable bowel, painful bladder, muscle spasm, fatigue, poor sleep, and nausea. Dysmenorrhea-associated pelvic pain represents a large area of unmet human need, and many women find inadequate respite from pain using current treatments.

We recognised that dysmenorrhoea-associated pelvic pain may be due to activation of the innate immune system, mediated at least in part by Toll-Like Receptors on cells in the uterus, and activation of glial cells in the dorsal horn of the spinal cord. To model dysmenorrhoea in mice, a study was undertaken administering LPS (lipopolysaccharide), a potent innate immune activator, to the uterus of mice once per cycle.

Studies were also undertaken to investigate whether a small dose of a Toll-Like Receptor blocker (amitriptyline) in

TABLE 1

|  | All women with dysmenorrhoea (All Dys) (n = 168) | No Laparoscopy (No Lap) (n = 45) | Endometriosis confirmed (Endo+) (n = 101) | Endometriosis excluded (Endo−) (n = 22) | Significance Endo+ vs Endo− (P value)* |
|---|---|---|---|---|---|
| Dysmenorrhoea (%) | 100 | 100 | 100 | 100 |  |
| Stabbing Pain (%) | 63.9 | 47.7 | 69 | 72.7 | 0.731 |
| Bowel Problems (%) | 47.3 | 40.9 | 49.5 | 50.0 | 0.966 |
| Food Intolerances (%) | 66.1 | 62.8 | 65 | 77.3 | 0.267 |
| Bladder Problems (%) | 23.2 | 18.2 | 20 | 50 | 0.005 |
| Headaches (%) | 56 | 46.7 | 58.4 | 63.6 | 0.651 |
| Sexual Pain (%) | 37.8 | 36.1 | 38.2 | 38.9 | 0.956 |
| Vulval Pain (%) | 38.6 | 35.9 | 41.2 | 31.8 | 0.415 |
| Fatigue (%) | 74.4 | 68.9 | 77.2 | 72.7 | 0.652 |
| Poor Sleep (%) | 57.7 | 57.8 | 58.4 | 54.5 | 0.739 |
| Nausea (%) | 49.1 | 42.9 | 48 | 66.7 | 0.12 |
| Sweating (%) | 33.9 | 28.9 | 33.7 | 45.5 | 0.296 |
| Dizziness/Faint (%) | 58.9 | 48.9 | 62.4 | 63.6 | 0.912 |
| Anxiety (%) | 58.7 | 61.4 | 56.4 | 63.6 | 0.536 |
| Low Mood (%) | 57.7 | 60 | 58.4 | 50 | 0.47 |

The results show a similar symptom profile across the groups, regardless of the presence or absence of endometriosis lesions. Statistical comparison between those with, and those without endometriosis lesions found significance only with regard to bladder symptoms, which were more common in those without endometriosis lesions.

In conclusion, in this example the presence of additional pain symptoms in women presenting with dysmenorrhea is independent, or substantially independent, of the presence or absence of endometriosis lesions.

the mouse uterus can reduce glial cell activation in the spinal cord, and reduce pain in this mouse model. To assess whether exemplary embodiments may reduce this pain amitriptyline was inserted into the uterus at estrus and the day after estrus over three successive cycles. To ensure that the amitriptyline acts by blocking TLRs, an investigation was also conducted on mice given a pure TLR4 blocker—TAK-242.

The Nonsurgical Embryo Transfer Device ("NSET" device) developed by Paratech USA has been used to allow the insertion of fluid to the uterus with brief, mild discomfort to the mouse, and no need for anaesthesia.

To measure glial activation in the spinal cord, we have measured changes in glial cells using immunofluorescence.

In the model, we investigated whether intrauterine LPS administration would cause an activation of the innate immune system in the uterus, replicating the inflammation often seen in dysmenorrhea, with possible association with pain. As inflammation is intrinsically linked with pain, we investigated whether activation of the innate immune system in the uterus would induce activation of spinal glial cells (central nervous system immune cells) in the dorsal horn of the spinal cord. Spinal glial cells include astrocytes and microglia. Activation of spinal glial cells was assessed using immunoflourescent staining with GFAP (astrocytes) or Iba1 (microglia). We then investigated if spinal glial activation is attenuated by the innate immune system blocking drugs amitriptyline and TAK-242.

(ii) Project Outline

To determine whether intra-uterine instillation of lipopolysaccharide (LPS) can induce glial change in the dorsal horn of the spinal cord. Multiple cohorts of mice were tested for intrauterine-LPS induced spinal changes, in accordance with the Phases listed below.

Process:
animal acclimatization: 1 week
animal habituation: 1 week
daily cervical smears: until 3 regular estrous cycles had been confirmed Animal Groups:

Group 1 included twelve mice with 20 μl endotoxin-free saline introduced to the uterus on the first day of estrus and the subsequent day over 3 consecutive estrous cycles. Group 2 included twelve mice with LPS (100 μg/kg) instilled in the uterus on the first day of estrus and saline injected on the subsequent day over 3 consecutive estrous cycles. Group 3 included twelve mice with LPS (100 μg/kg) mixed with amitriptyline (20 μl of a 100 μM solution, equivalent to 28 μg/kg) instilled in the uterus on the first day of estrus, and amitriptyline alone instilled on the subsequent day over 3 consecutive estrous cycles. Group 4 included 14 mice with LPS (100 μg/kg) mixed with TAK-242 (20 μl of a 100 μM solution, equivalent to 36 μg/kg) instilled on the first day of estrus and TAK-242 alone instilled on the subsequent day over 3 consecutive estrous cycles.

For this study, a mouse model (Balb/C) was selected for the following reasons:
(a) While mice do not menstruate, they do undergo hormonally based cyclical changes in the uterus according to the phase of their oestrous cycle, and offer a useful mammalian alternative, with similar uterine physiology to humans;
(b) Mice have a uterus that is accessible to drug administration during the estrus phase of their estrous cycle; and
(c) Mice have a short estrous cycle (4-7 days) that allowed us to complete the study over 3 estrous cycles within our planned research time frame.

Determination of spinal glial response was then assessed using immunofluorescence to confirm the validity of the experimental model. We confirmed that instillation of intra-uterine LPS induced activation of spinal astrocytes and microglia.

Determination of the ability of TLR4 antagonists to block the activation of spinal astrocytes and microglia induced by intra-uterine instillation of LPS was assessed.

Agents:
(i) LPS
Dose Rate: once every 5-7 days each oestrous cycle in estrous. Instillations were done on the first day of estrus and then the subsequent day, over 3 consecutive oestrus cycles.
Frequency: 3 doses total for each animal in group 2, 3 and 4, instilled on the first day of estrus in 3 consecutive estrous cycles
Route Administered: intrauterine
Concentration and total dose: 100 ug/kg
(ii) Amitriptyline.
Amitriptyline is a generic medication with established use in humans, and high affinity as an antagonist at a TLR 2/4 receptor. Amitriptyline is a non-specific antagonist of TLR2/4.
Dose Rate: Instilled in the uterus on the first day of estrus, and the subsequent day over 3 consecutive estrous cycles.
Frequency: 6 doses total for each animal in Group 3 instilled on the first day of estrus and the subsequent day over 3 consecutive estrous cycles
Route Administered: Intrauterine
Concentration and total dose: 100 uM in 20 uL (20 μl of a 100 μM solution, equivalent to 28 μg/kg) per dose.
(iii) TAK-242
TAK-242 is a specific TLR4 antagonist.
Dose Rate: Instilled in the uterus on the first day of estrus, and the subsequent day over 3 consecutive estrous cycles.
Frequency: 6 doses total for each animal in Group 3 instilled on the first day of estrus and the subsequent day over 3 consecutive estrous cycles
Route Administered: Intrauterine
Concentration and total dose: 100 uM in 20 uL (20 μl of a 100 μM solution, equivalent to 36 μg/kg)
(iii) Procedure These experiments mimicked the cyclical pain of human dysmenorrhea over 3 successive mouse estrous cycles. The studies provoke a response over three hormonal cycles, as it is becoming increasingly recognised that many inflammatory or immune-based diseases require repeated immune stimuli to develop. While an initial event may heighten the sensitivity of the immune system to future immune challenges, it is repeated stimuli that are required for full development of the disease condition.

Agents were e administered to the uterus during the estrous phase of the mouse reproductive cycle. This is the time of high estrogen, a known contributor to TLR sensitivity, and a time when the mouse cervix is maximally open and most easily cannulated with least discomfort to the animal.

Experimental Stages

The investigation involved the instillation of 20 ul of an endotoxin-free 0.9% saline solution into the uterus of all animals on the first day of estrus and the subsequent day during 3 consecutive estrous cycles. Additional agents added to the saline were included according to the groups outlined below. Where LPS is administered, this was done on only 1 day per estrous cycle.

Where amitriptyline or TAK-242 was administered, this is on both the first day of estrus and the subsequent day.

The research comprises 4 groups of mice. These were:
Group 1 (12 mice)—saline 0.9% only (control) animals
Group 2 (12 mice)—saline 0.9% plus LPS 100 ug administered animals.

Groups 1 and 2 confirm the ability of intra-uterine LPS (100 ug) to induce glial change in the dorsal horn of the spinal cord Group 3 (12 mice)—saline 0.9% plus LPS plus amitriptyline Group 4 (14 mice)—saline 0.9% plus LPS plus TAK-242.

Groups 3 and 4 determine whether co-administration of 2 drugs known to modify innate immune cell activation via TLRs, are able to modify the spinal response.

Experimental Plan/Flow Chart

The procedure for all animals is outlined below.

One Week Prior to Experimentation:

Upon arrival to facility at 8-10 weeks of age, all animals remained in their home cages without intervention to acclimatise to their holding room. Following this, all animals were handled daily by the experimenter to familiarise the animals to regular handling for 5 days. Following acclimatisation and familiarisation all animals underwent cervical smears every morning. Mice were smeared using the common pipette cervical smear technique to confirm that they are cycling regularly and to record and predict what phase of the estrous cycle they were in, to allow correct timing of experimental procedures. The four phases of the mouse estrous cycle are estrus, estrus, metestrus and diestrus, each typically last for one-two days. The cervical smear testing involves the mouse being held by the operator with the ventral surface facing uppermost. A 4 mm (outer diameter) plastic speculum was inserted in the vagina for this purpose to aid collection, and to accustom the animal to the vaginal speculum required for later intra-uterine instillations. 0.1 ml 0.9% saline was flushed into the vagina and back up into the pipette, twice. One or two drops of the resulting cell suspension was placed onto a glass side and a cover slip sealed on top of the sample, which was then examined using light microscopy.

Subsequent Investigation Over Three Consecutive Estrous Cycles

Once 3 regular estrous cycles in each mouse had been confirmed, intrauterine administration of agents was performed beginning at estrus.

The daily intrauterine installation of agents was performed using the NSET device (Paratechs, USA). In this regard, unlike humans, mice have a bicornuate uterus, and that instillation of fluid instilled through the cervix may flow into either one horn or both horns of the uterus with potential for unilateral effects. This was confirmed in pre-research testing with intra-uterine instillation of blue dye into mice.

LPS Stimulation Days

LPS, a Toll-Like Receptor agonist, was instilled in the uterus once per cycle (every 5-7 days), timed with the first day of estrus. We used 100 ug LPS in 10 µl of endotoxin-free 0.9% saline to stimulate uterine inflammation and induce a dorsal horn glial cell response. The induction of an inflammatory condition in the mouse was required to mimic dysmenorrhea in women. However, we anticipated that this response would resolve over 24 hours.

For the groups, animals were monitored throughout the experimental period utilising clinical records sheets to ensure severe adverse effects were recorded and dealt with accordingly.

This cycle of intrauterine administration of LPS on the first day of estrus with twice daily monitoring for 72 hours, then daily monitoring from then on, was repeated two more times, to a total of 3 cycles. This aimed to replicate the cyclical nature of dysmenorrhea in human females.

Behavioural Testing:

24 hours following the final LPS stimulation mice were subjected to assessment for the presence or absence of pain. This was assessed using the following tests:

Facial Grimace Scale: Photos of mice in their home cage will be taken, to score their facial Grimace and this was quantified and compared between groups. For further information see: http://www.nature.com/nmeth/journal/v7/n6/full/nmeth.1455.html.

Hargreaves test: The Hargreaves test uses a high-intensity beam of light directed at the hindpaw. An investigator then measures the time it takes for the animal to withdraw its hindpaw. A Hargreaves test was used to detect thermal pain sensitivity.

To enhance the quality of fixation of spinal cord tissues, a rapid transcardial perfusion fixation of tissues was undertaken, while the animal was anaesthetised.

Following humane euthanasia, the following tissues were harvested from the animals:

The spinal cord was assessed using immunohistochemistry techniques across levels T10, T11, T12, T13, L1, L2, L3, L4, L5, L6, S1 and S2 for Groups 1 and 2, where T represents the thoracic segment of the spinal cord, L represents the lumbar segment of the spinal cord and S represents the sacral segment of the spinal cord.

The spinal cord was assessed using immunohistochemistry techniques across levels T12, T13, L1, L2, L3, L4, L5, L6, S and S2 for Groups 3 and 4, where T represents the thoracic segment of the spinal cord, L represents the lumbar segment of the spinal cord and S represents the sacral segment of the spinal cord.

An assessment of glial activation was made using immunochemistry techniques including Ionized calcium binding adaptor molecule 1 (Iba1) expression and glial fibrillary-associated protein (GFAP) variability in the dorsal horn. Iba1 expression is a marker for microglial activation, and GFAP is a marker for astrocyte activation. The spinal cord levels chosen are consistent with the level of spinal afferent neurons associated with the pelvis, including the uterus in the mouse.

2. The uterus (iv) Results

Fluorescent immunochemistry was undertaken across spinal levels T10, T11, T12, T13, L1, L2, L3, L4, L5, L6, S1, and S2 for Groups 1 and 2. Fluorescent immunochemistry was undertaken across spinal levels T12, T13, L1, L2, L3, L4, L5, L6, S1 and S2 for Groups 3 and 4. In both groups, T represents the thoracic segment of the spinal cord, L represents the lumbar segment of the spinal cord and S represents the sacral segment of the spinal cord.

Figure 2:
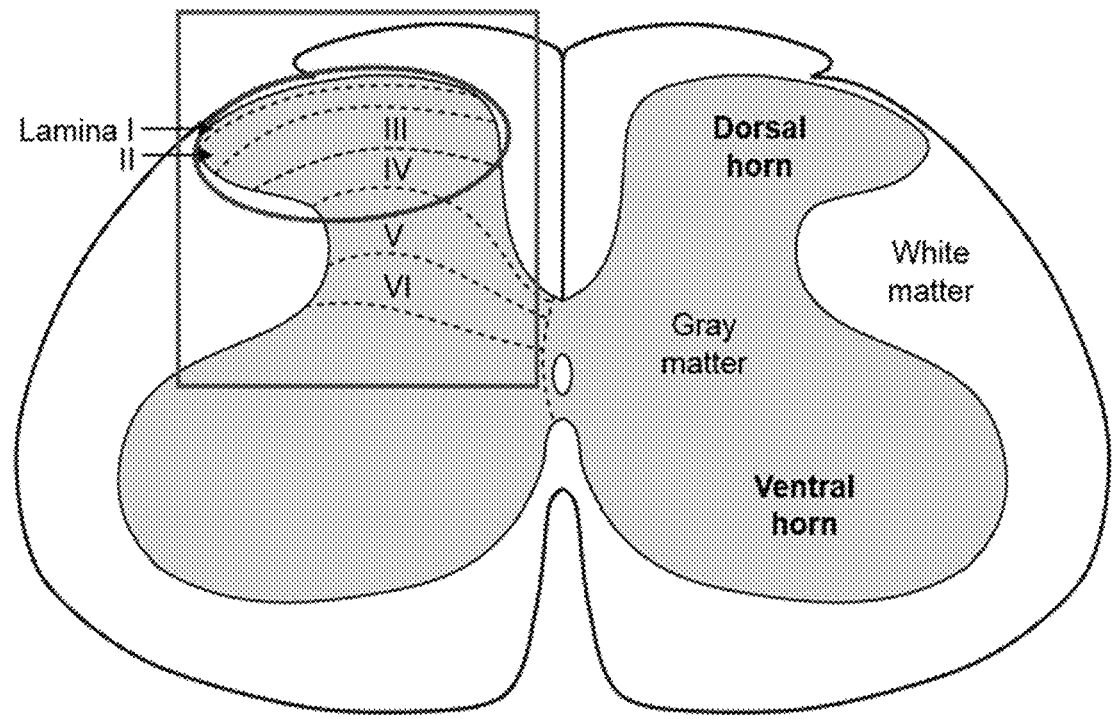
FIG. 2 shows a schematic diagram of a transverse section of the mouse lumbar spinal cord. Major regions of white and gray matter, the dorsal and ventral horns, and locations of Rexed laminae I to VI within the dorsal horn are shown. The ellipsoid denotes the approximate position of ROIs used for measurements of glial immunoreactivity, and the box represents fields of view of images captured for analysis.
Figure 3A:
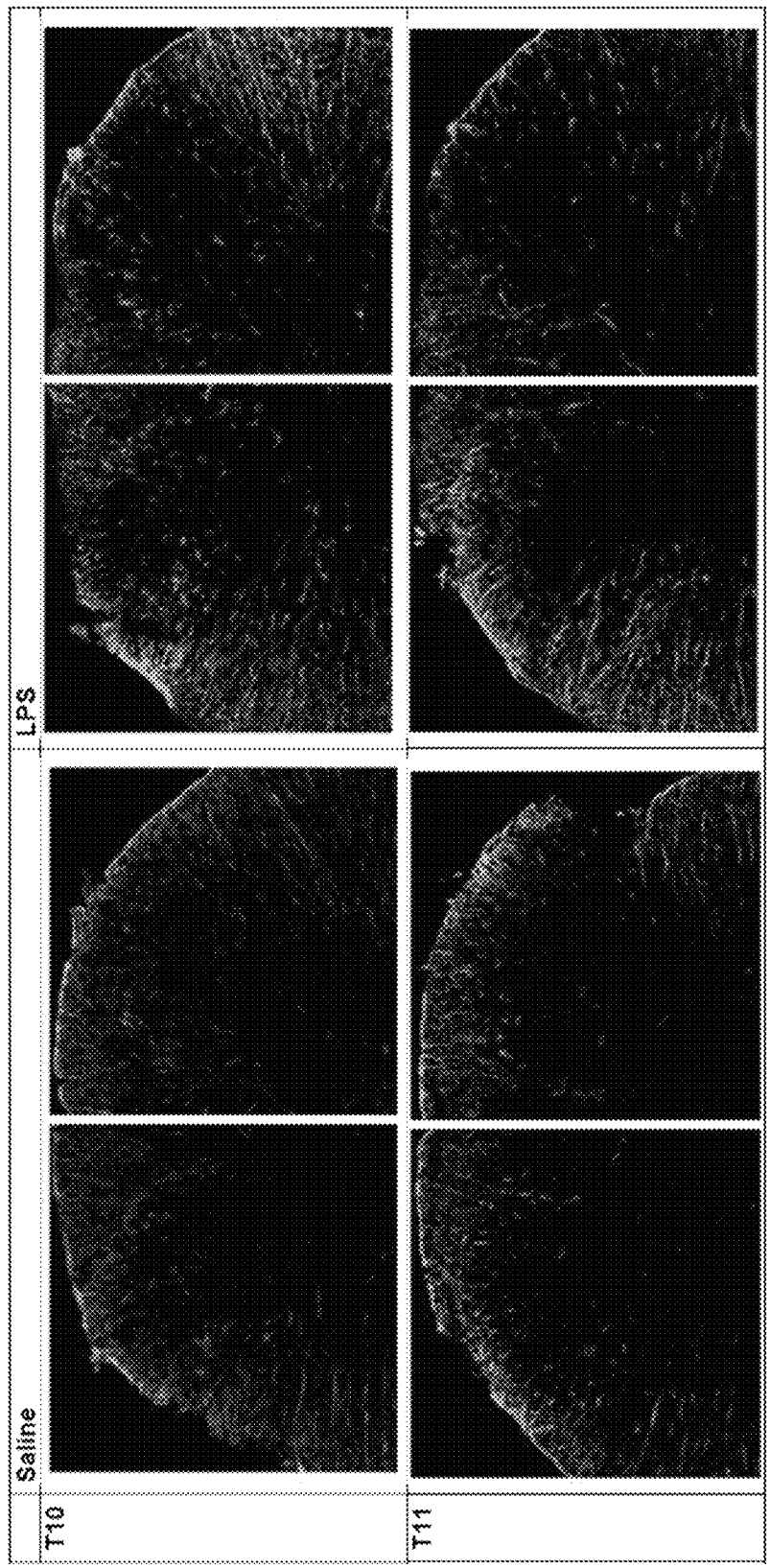
FIGS. 3A-3F show astrocyte (glial) staining of the dorsal horn with GFAP stain in saline or (lipopolysaccharide) LPS treated mice. Intrauterine LPS induced an increase in GFAP astrocyte staining through widespread levels of the spinal cord.
Figure 3B:
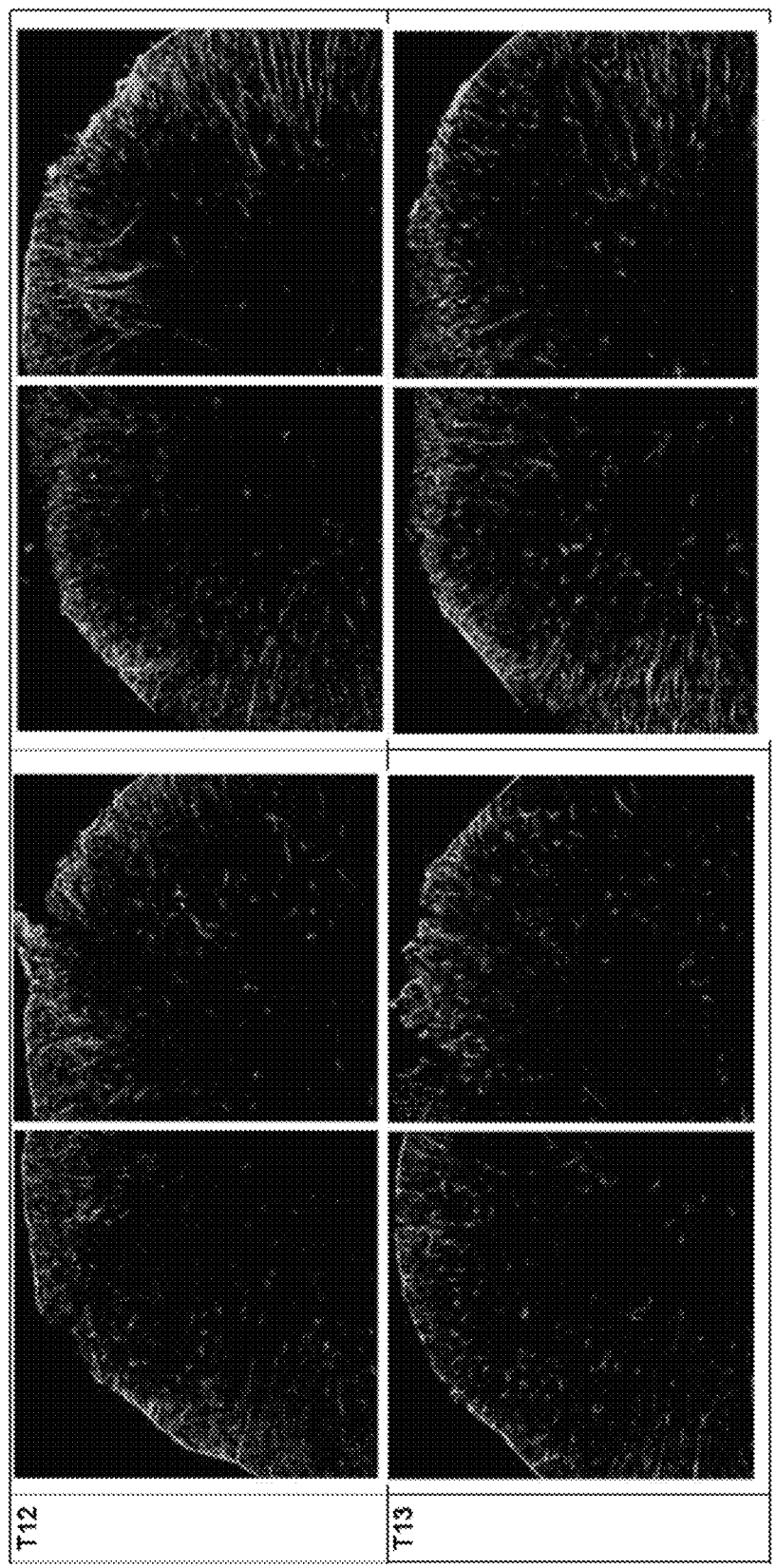
Figure 3C:
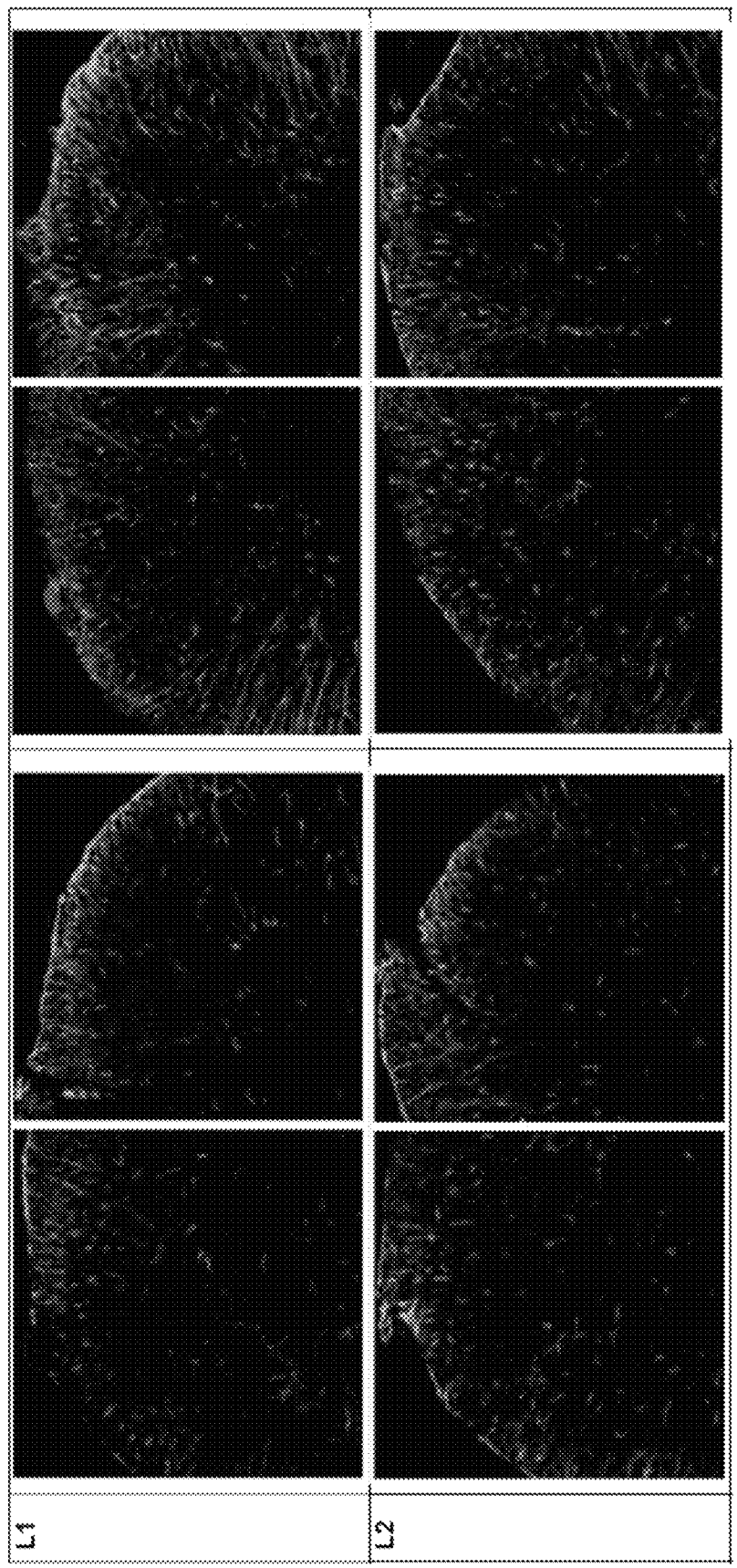
Figure 3D:
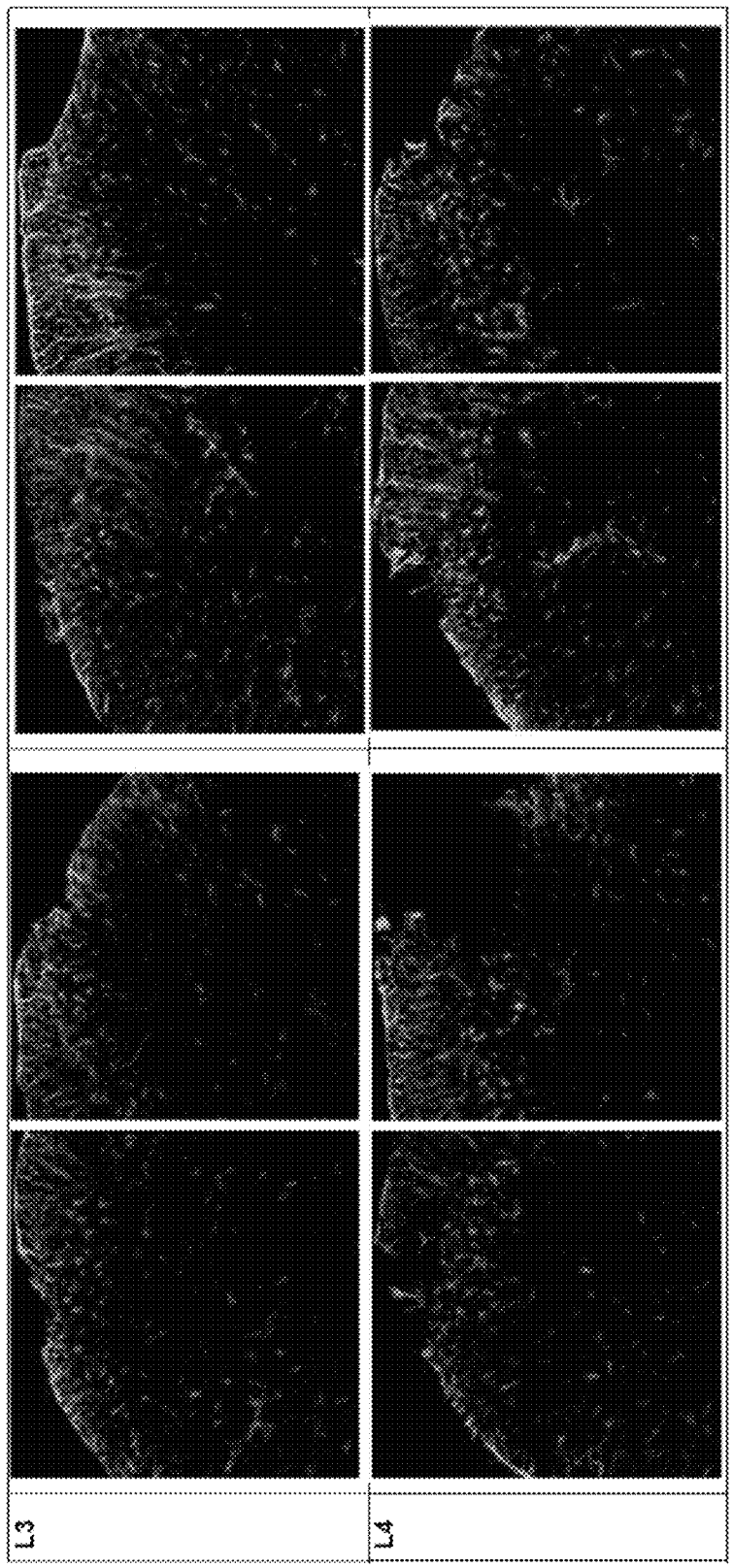
Figure 3E:
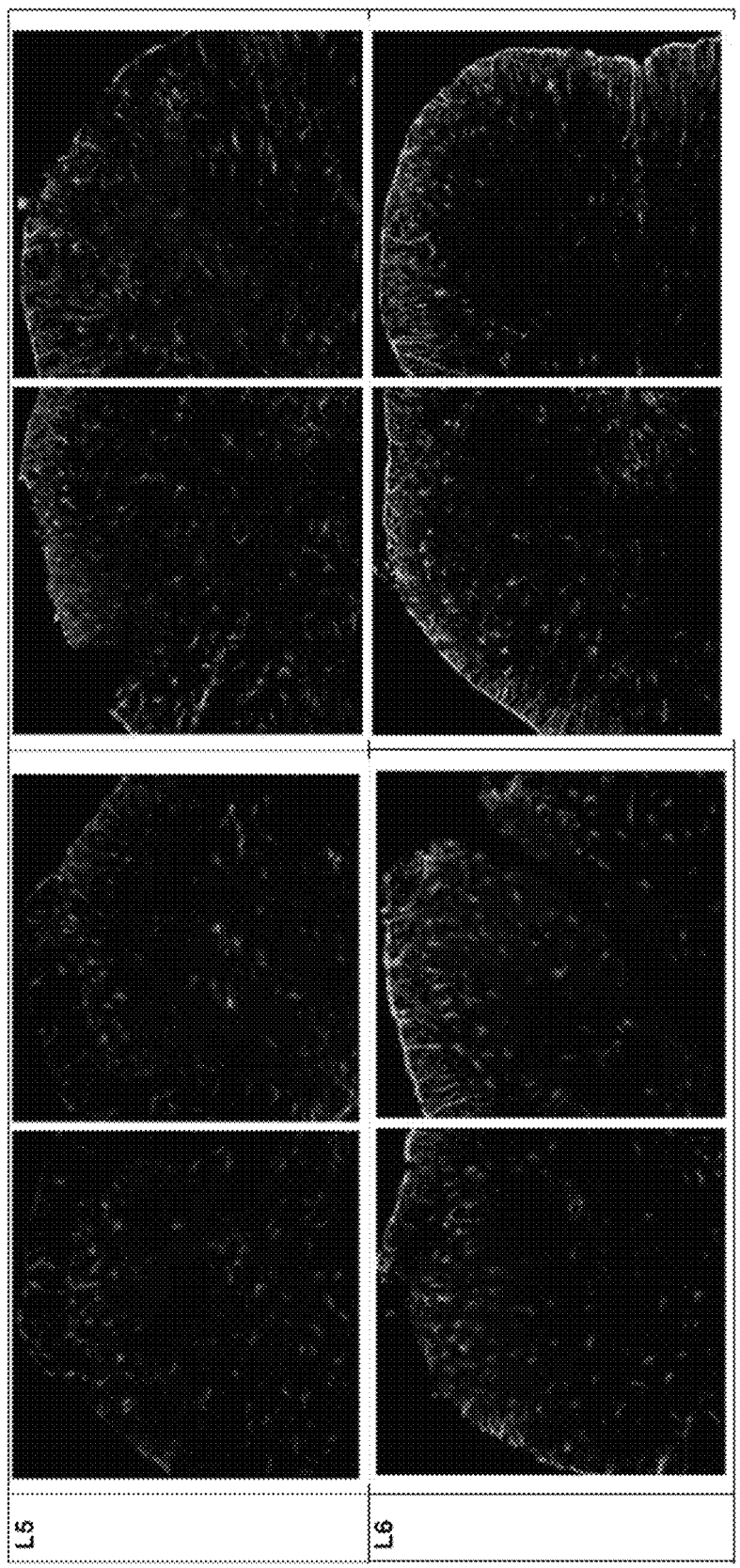
Figure 3F:
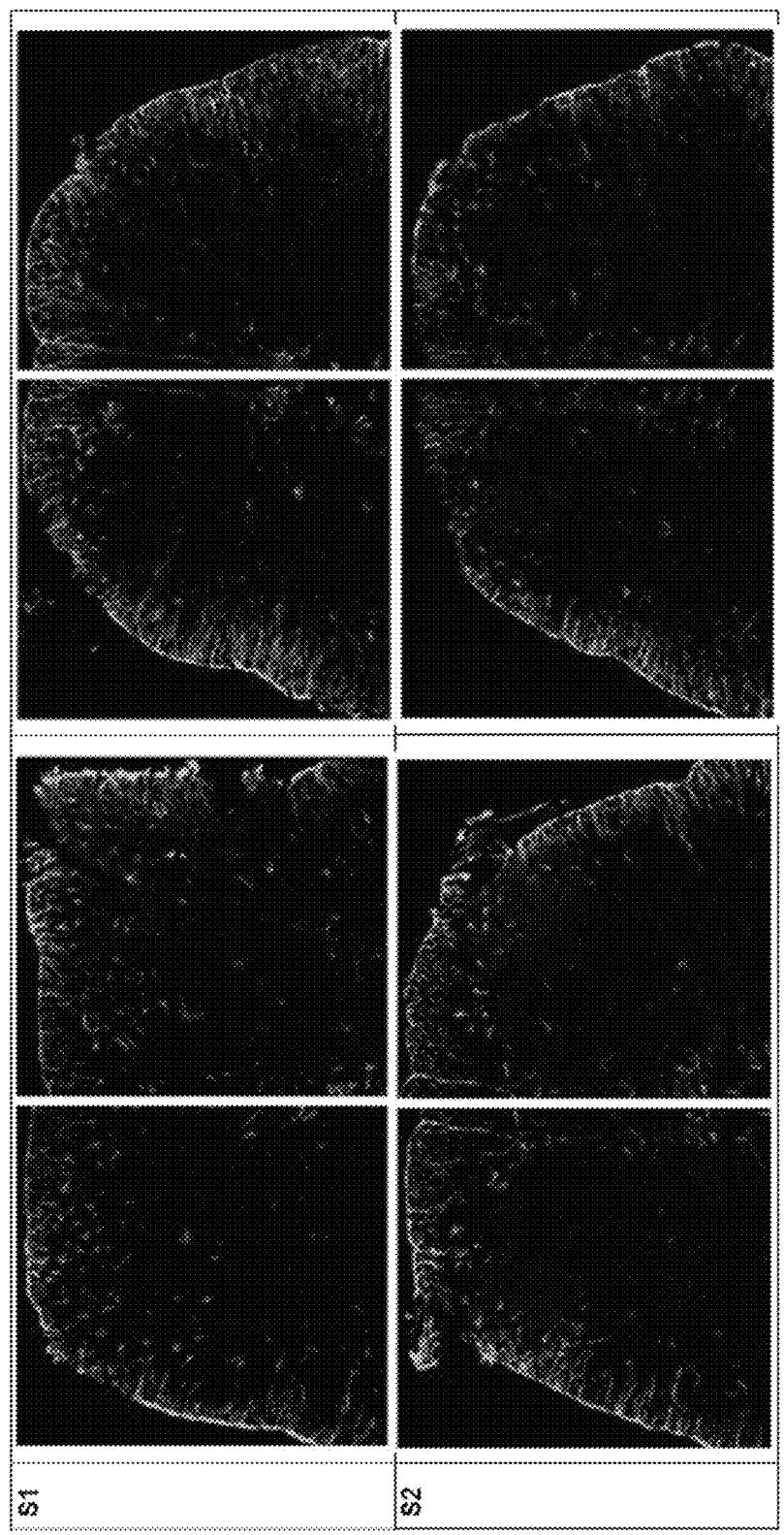
Figure 4A:
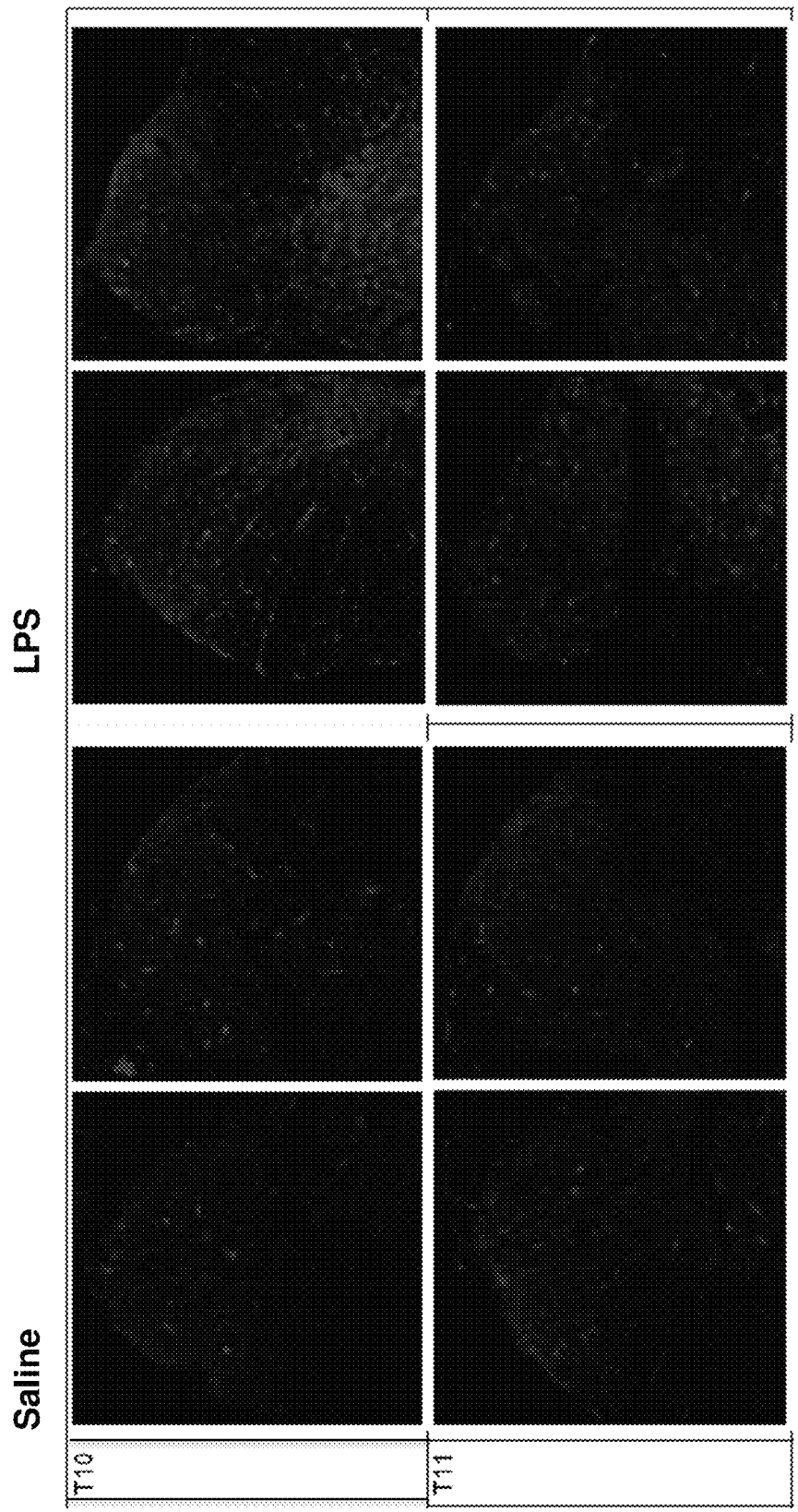
FIGS. 4A-4E show microglial (glial) staining of the dorsal horn with Iba1 stain in saline or LPS treated mice. Intrauterine LPS induced a localised increase in Iba1 microglial staining through select levels of the spinal cord.
Figure 4B:
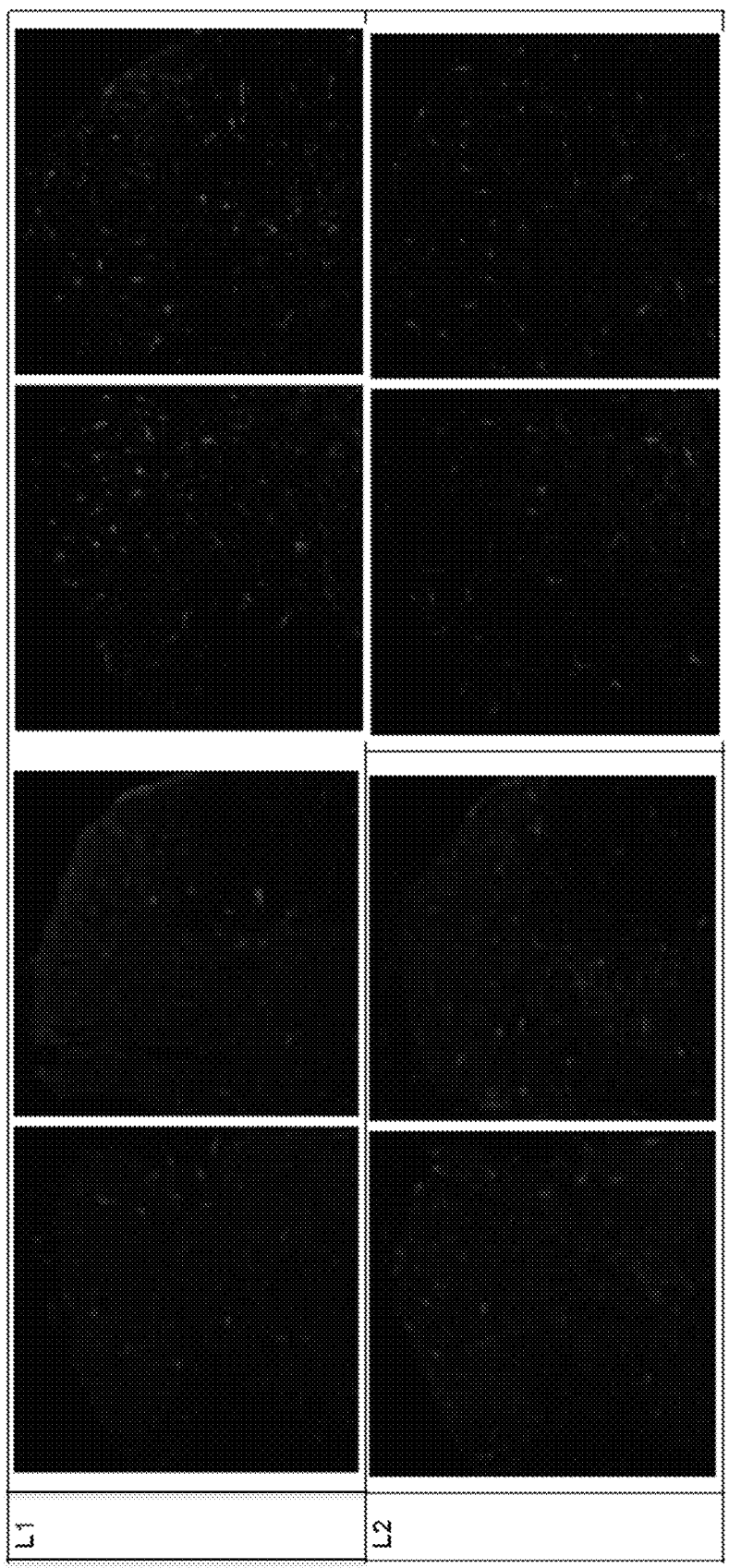
Figure 4C:
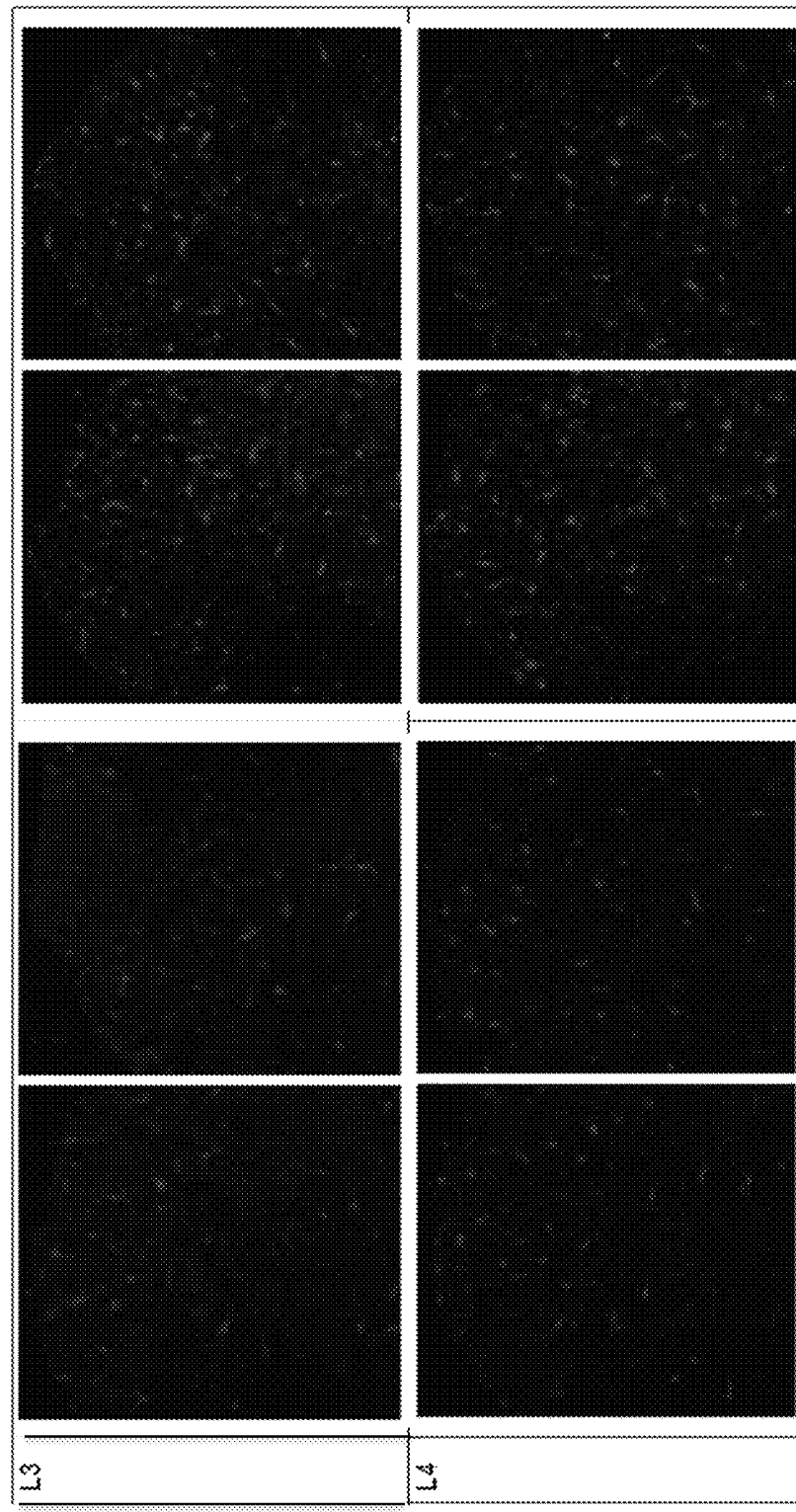
Figure 4D:
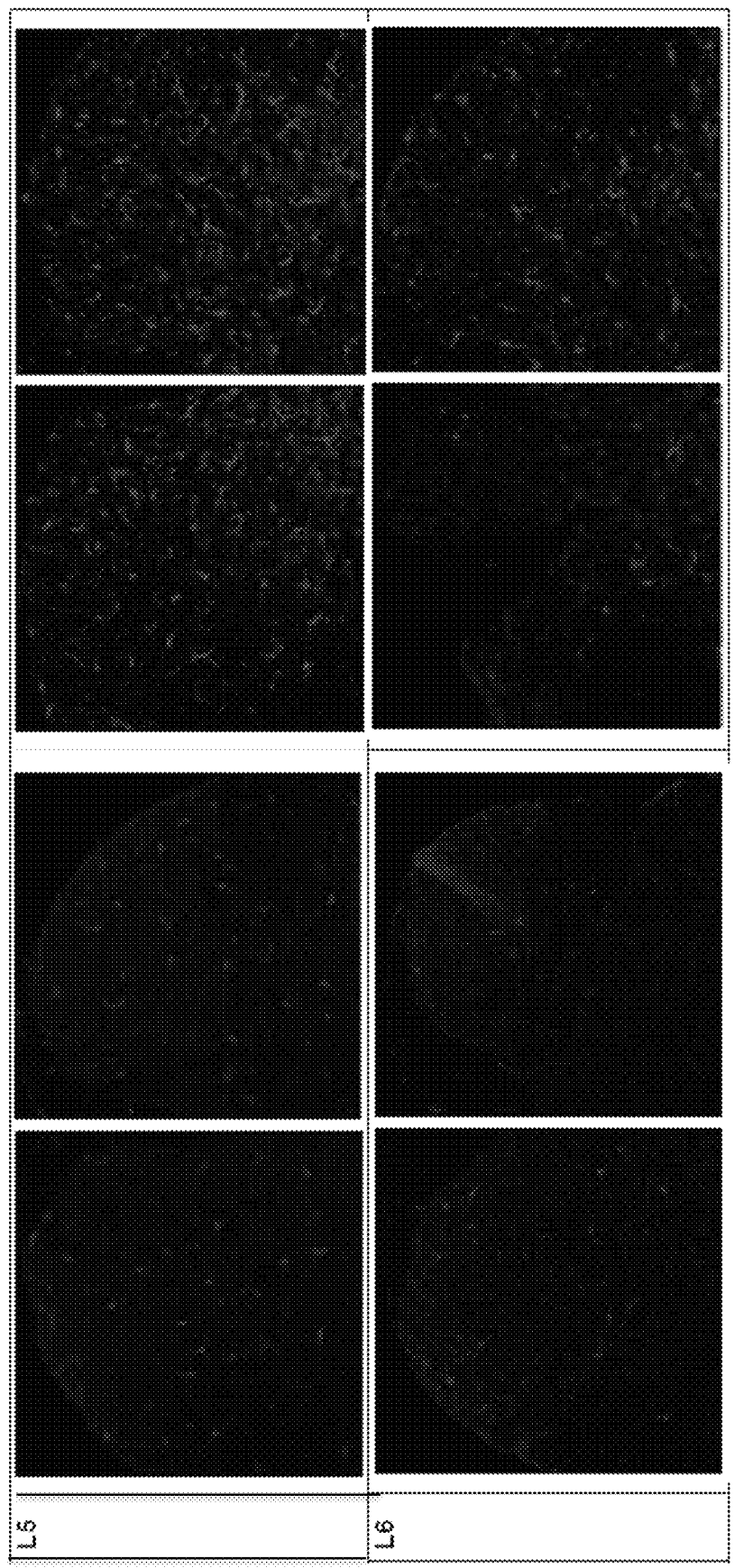
Figure 4E:
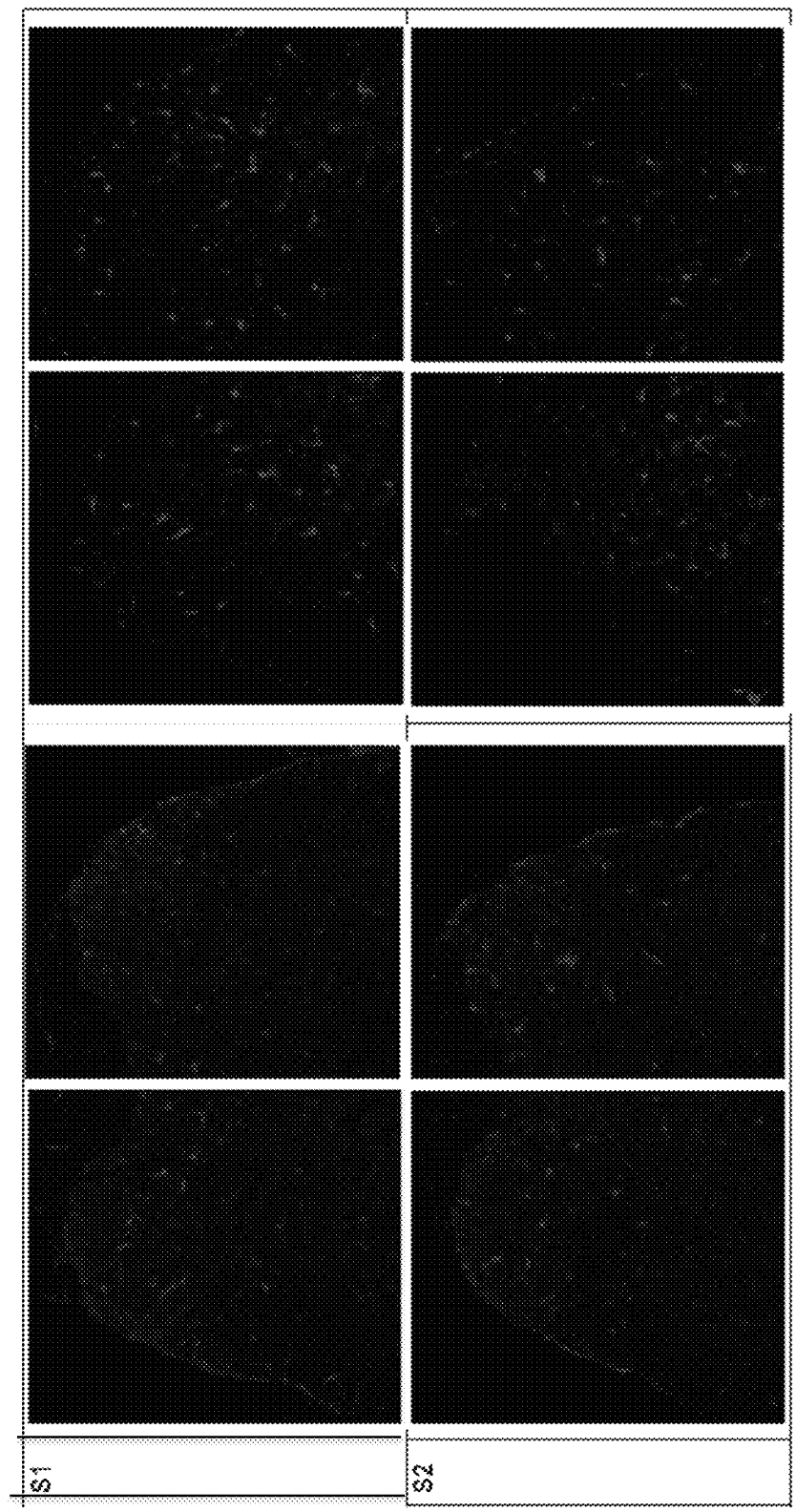
Figure 5A:
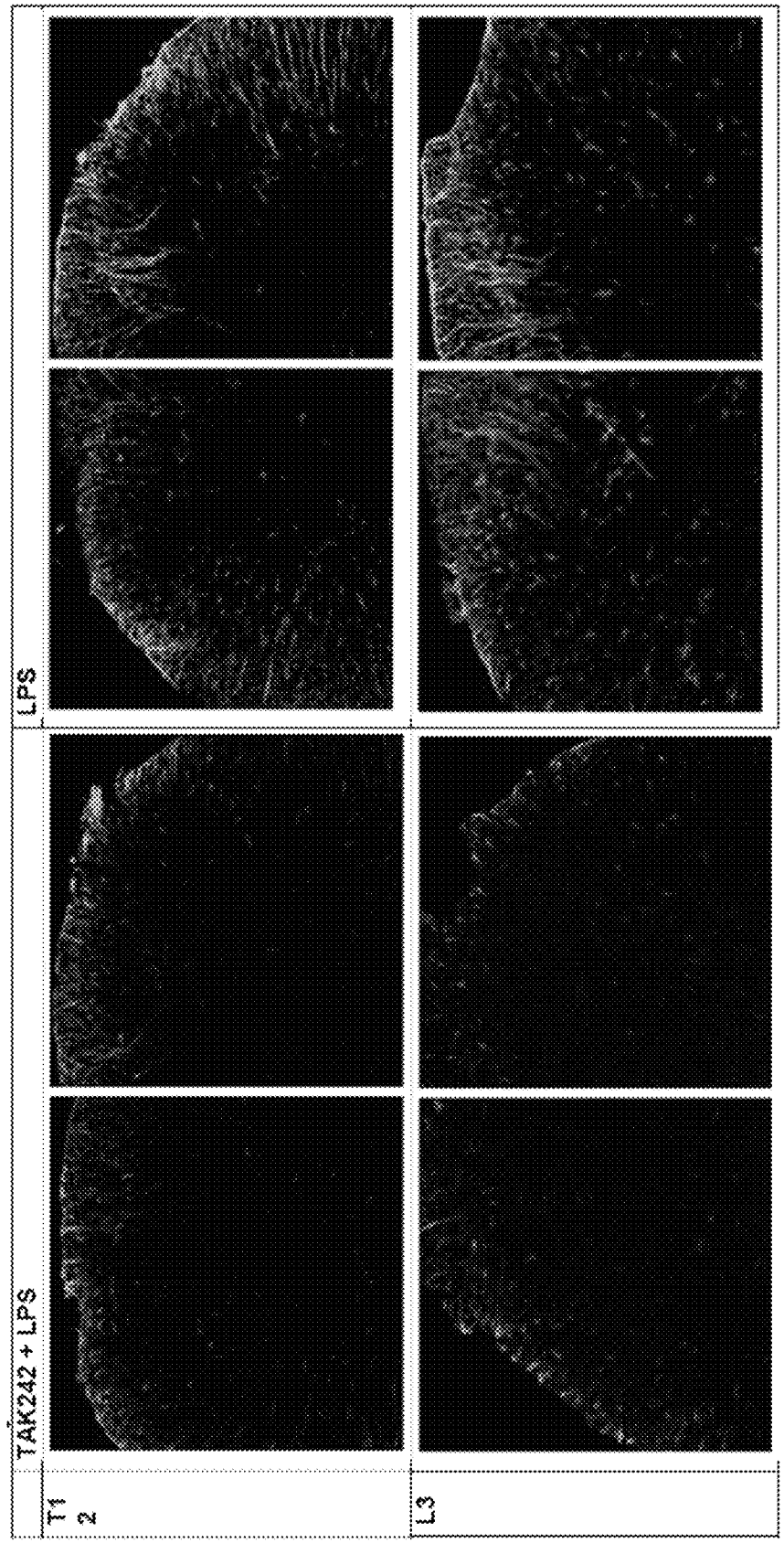
FIGS. 5A-5D show treatment with TAK242 blocks the impact of intrauterine LPS at multiple levels of the spinal cord and reduced astrocytic reactivity to below basal levels, using staining for Iba1. TAK242 is a selective inhibitor of TLR4 only.
Figure 5B:
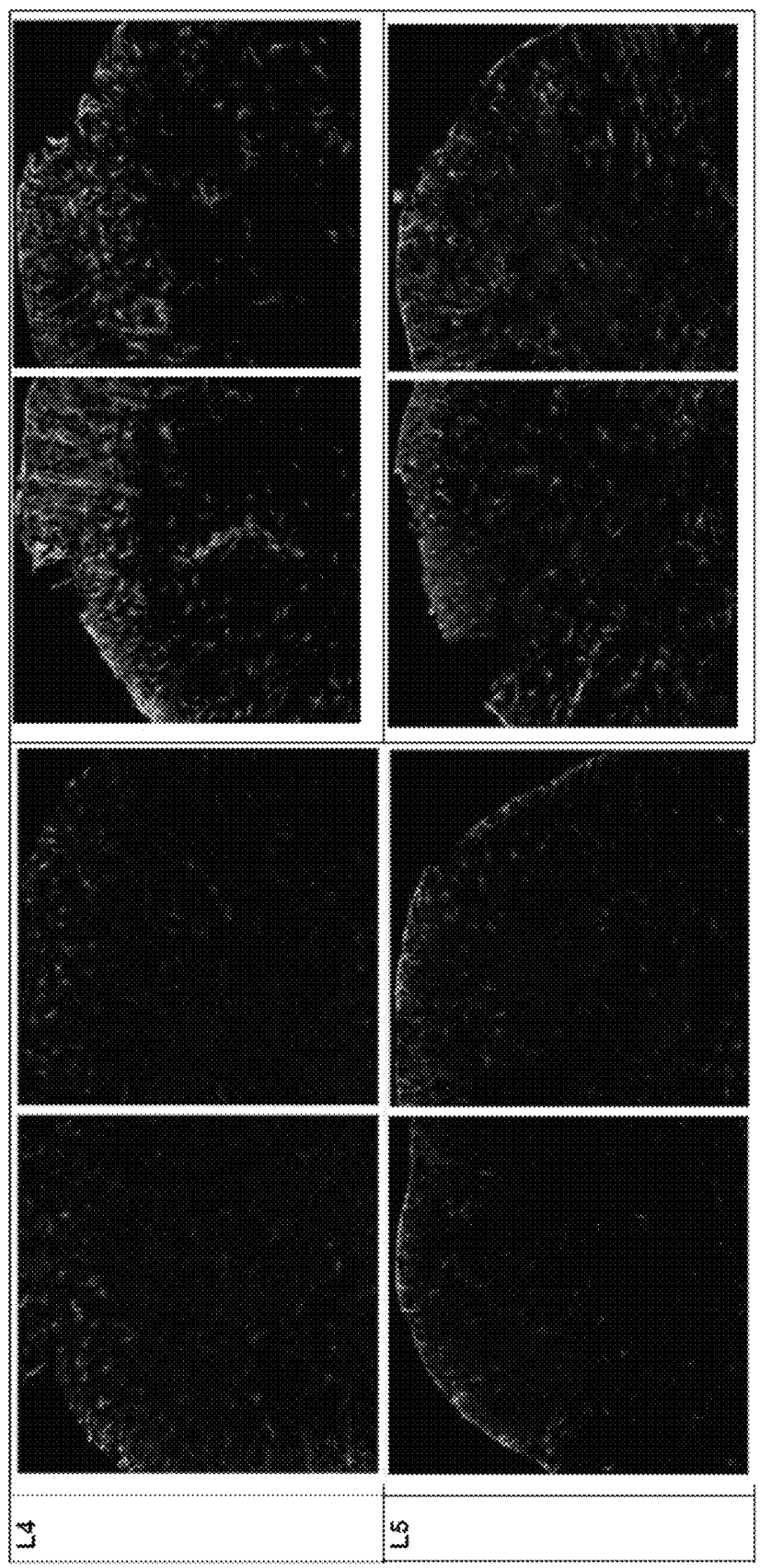
Figure 5C:
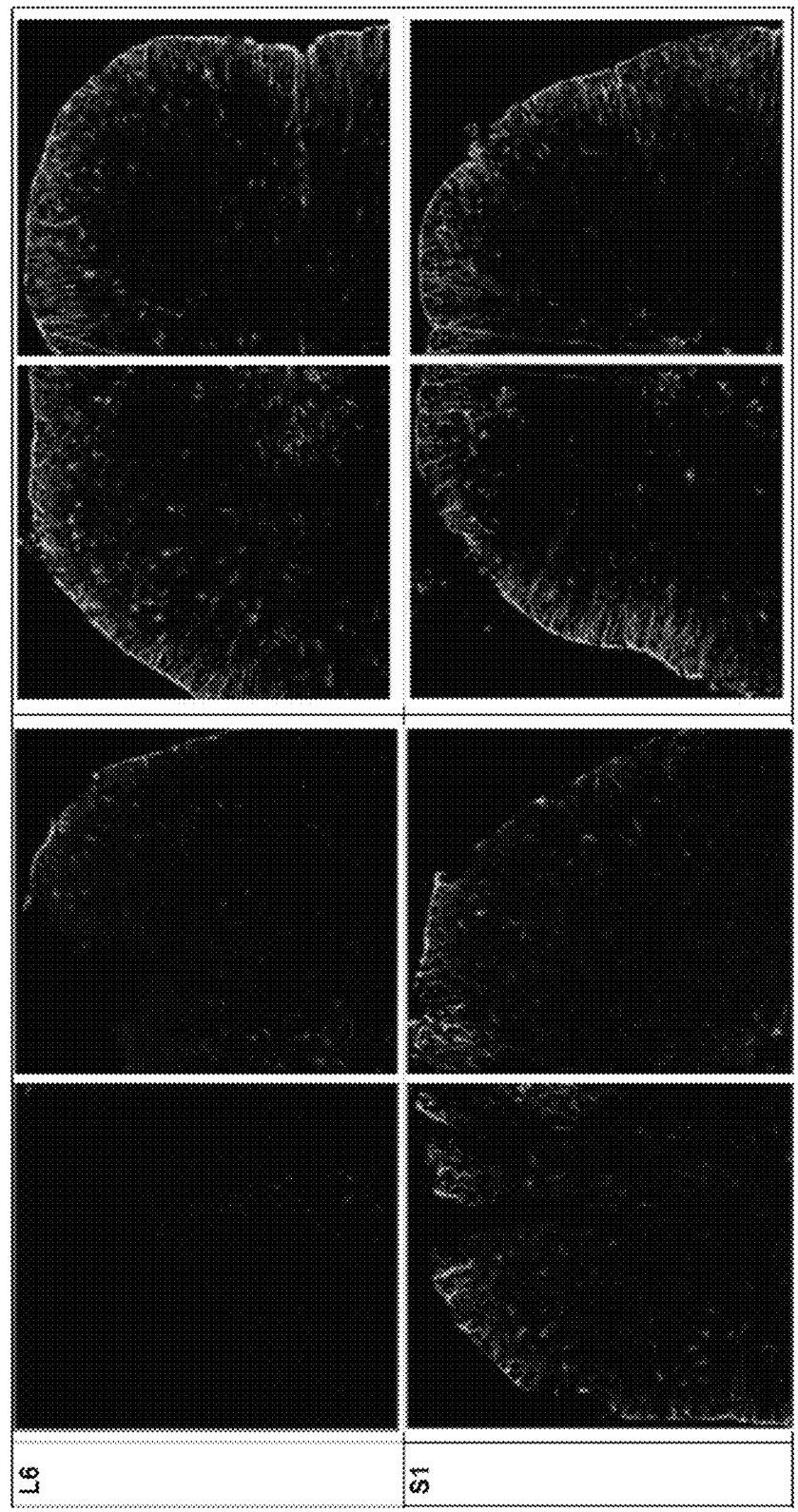
Figure 5D:
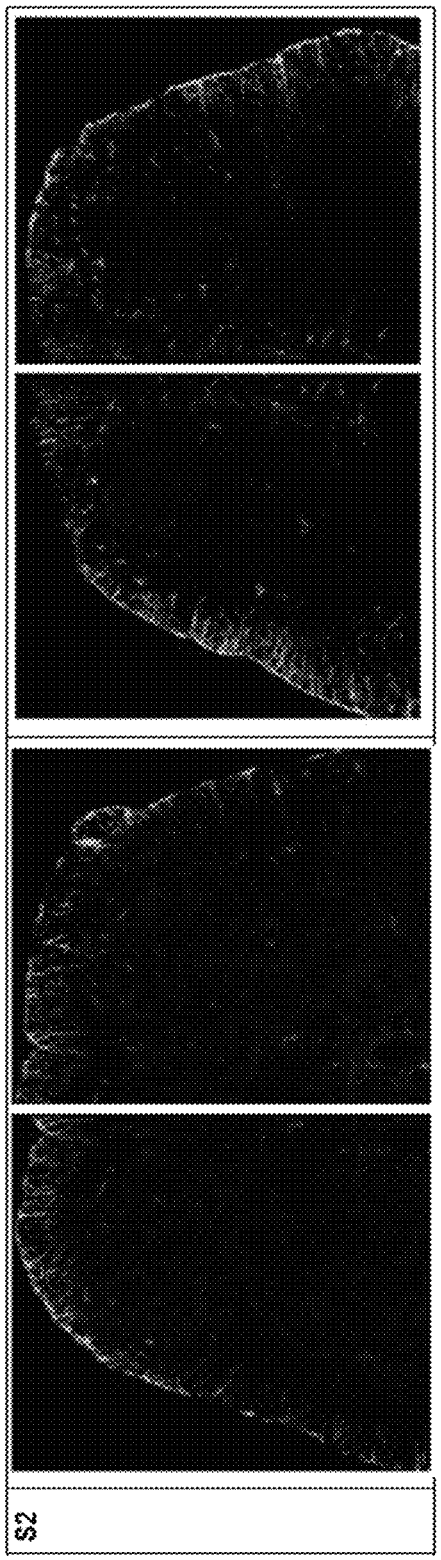
Figure 6A:
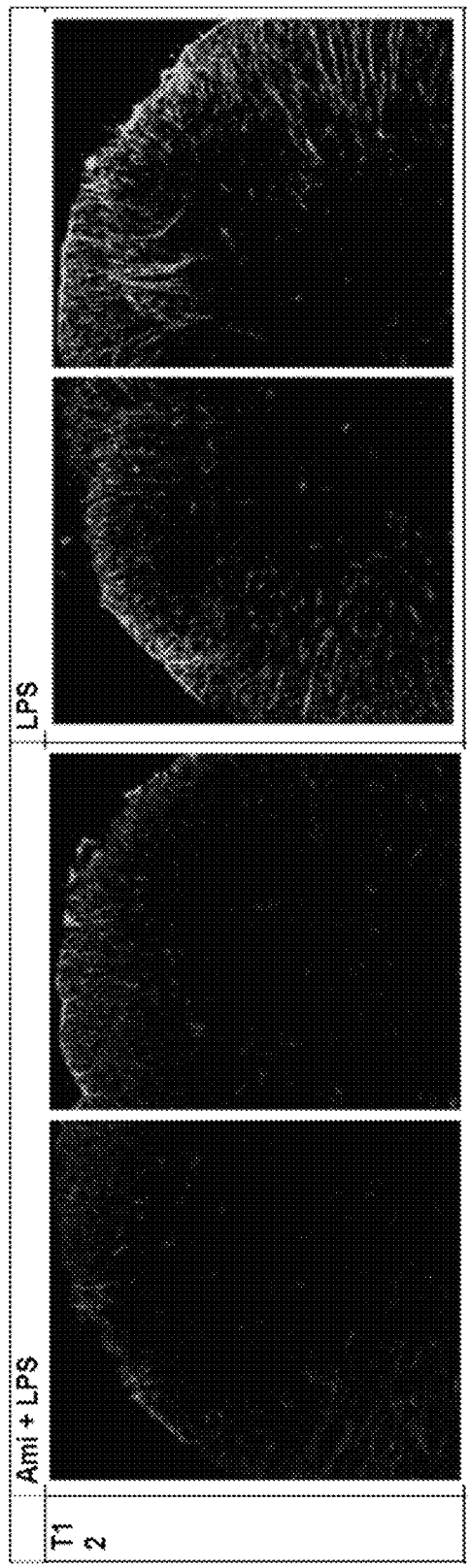
FIGS. 6A-6D show amitriptyline treatment blocks the impact of intrauterine LPS at multiple levels of the spinal cord and reduced astrocytic reactivity to below basal levels using staining with GFAP. Amitriptyline is an inhibitor of TLR4 and TLR2, and also an inhibitor of TLR3, TLR5, TLR8, TLR9, Dectin-1a, Dectin-1b, Mincle, NOD-1, NOD-2, RIG-1 and MDA-5.
Figure 6B:
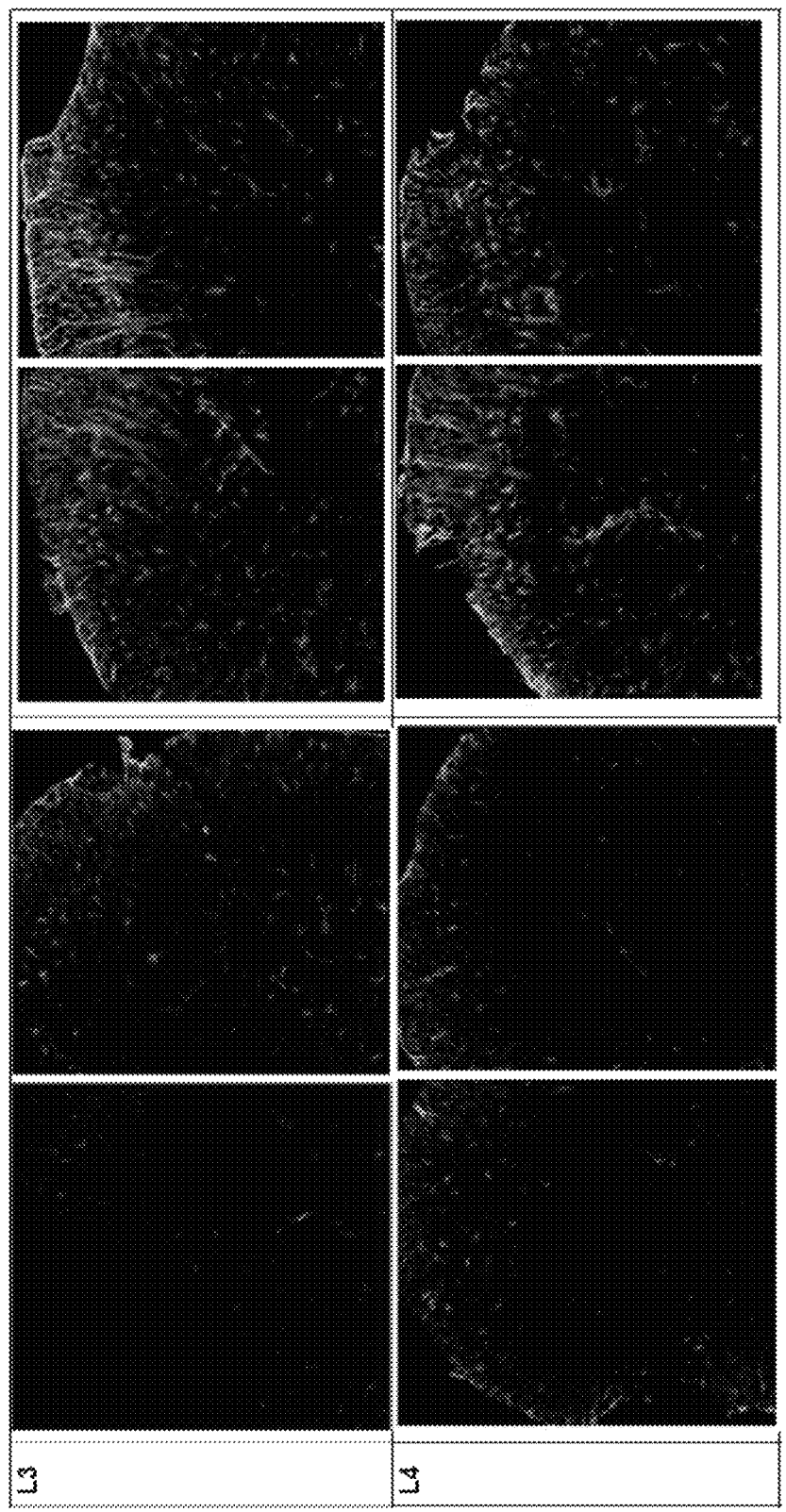
Figure 6C:
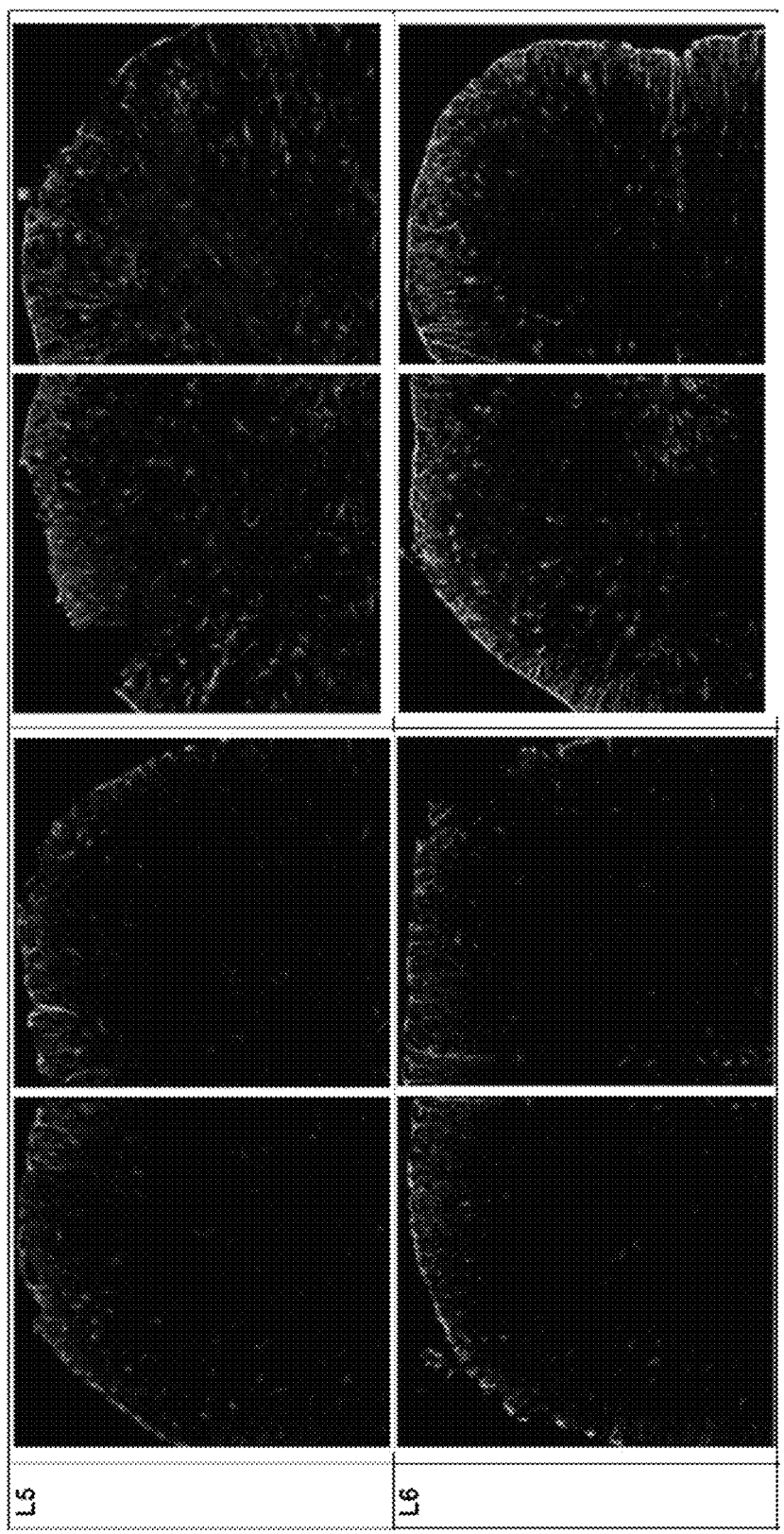
Figure 6D:
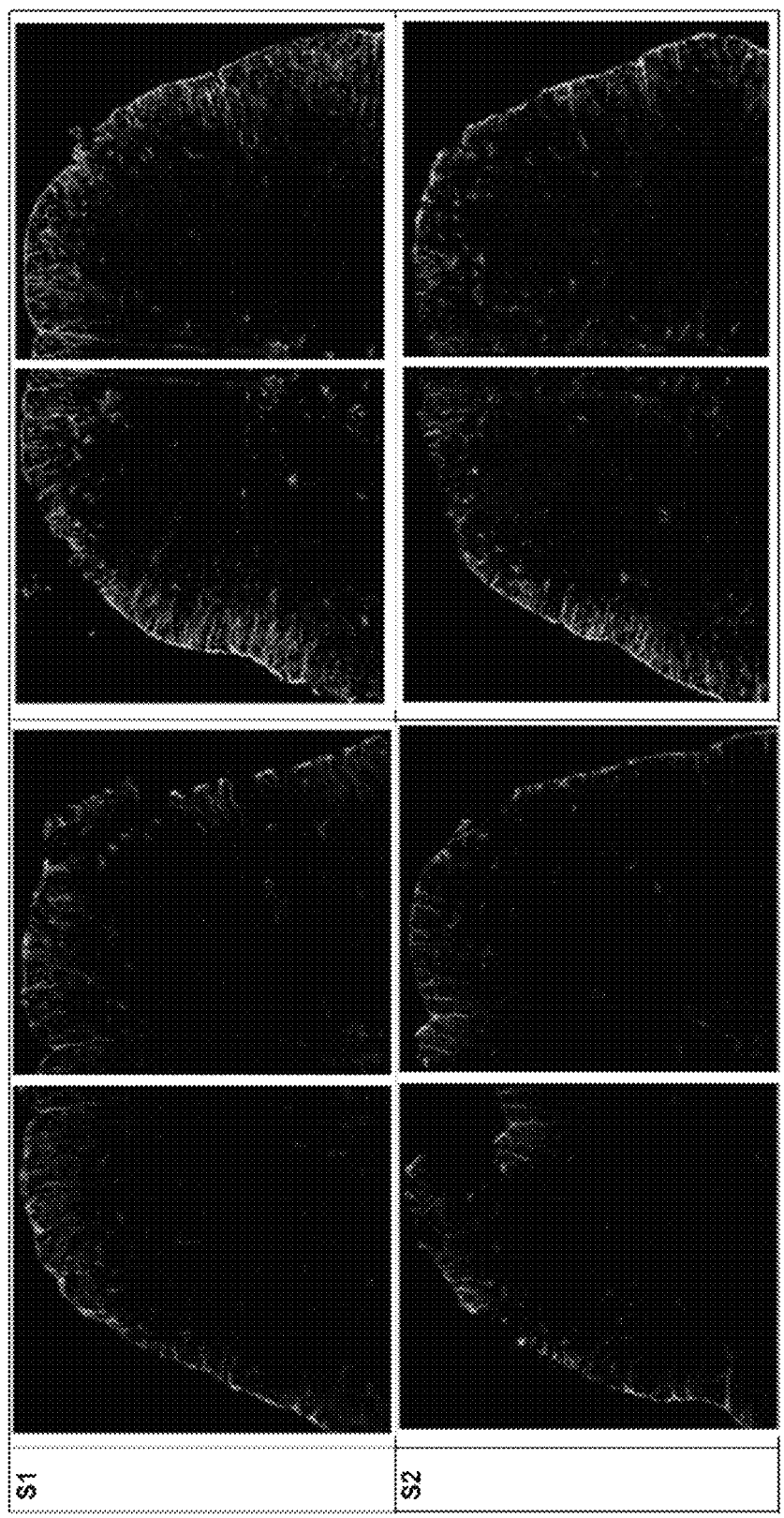
Figure 7A:
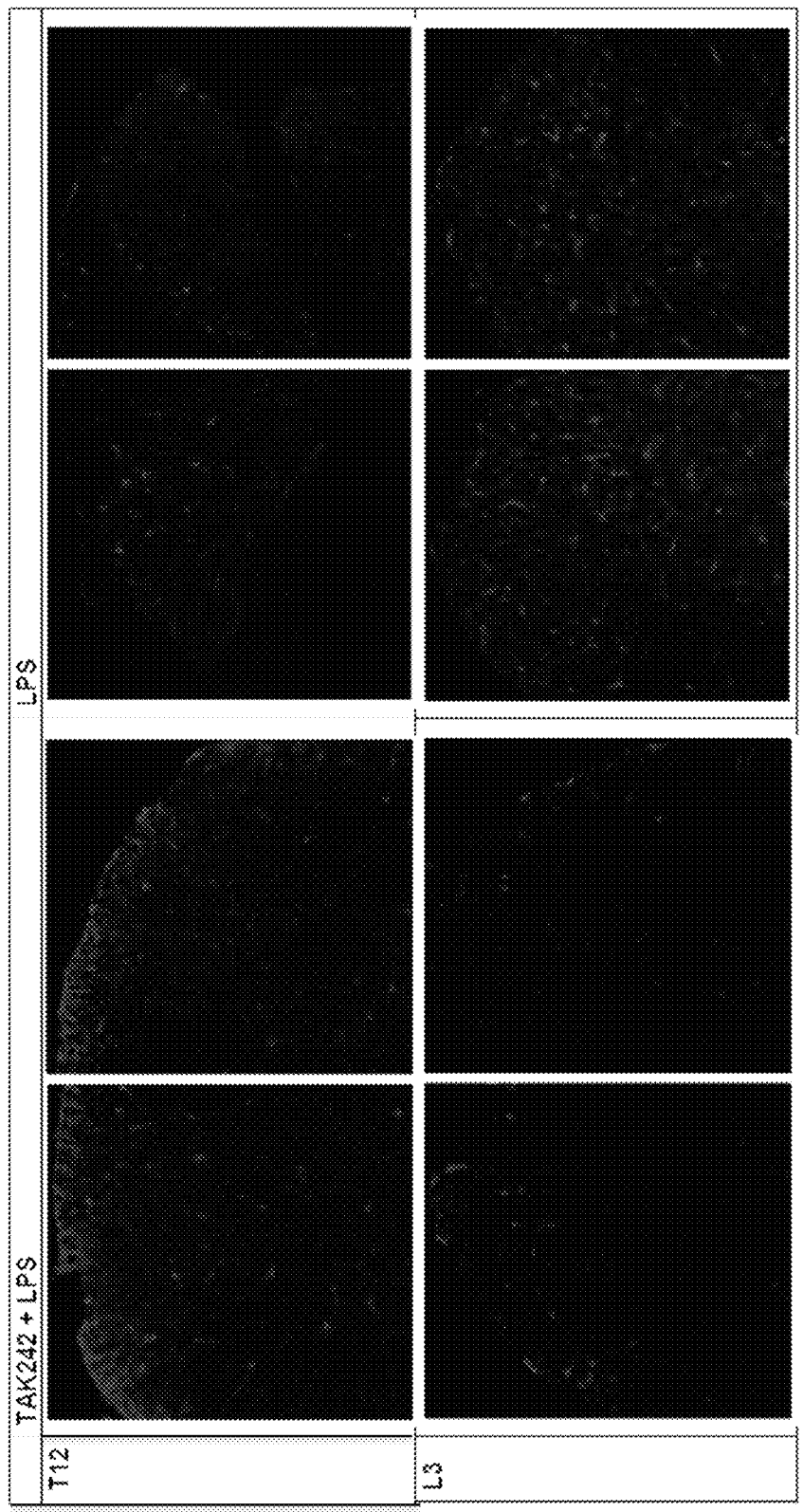
FIGS. 7A-7D show TAK242 treatment blocks the impact of intrauterine LPS at multiple levels of the spinal cord and reduced microglia reactivity to basal levels using staining for Iab1.
Figure 7B:
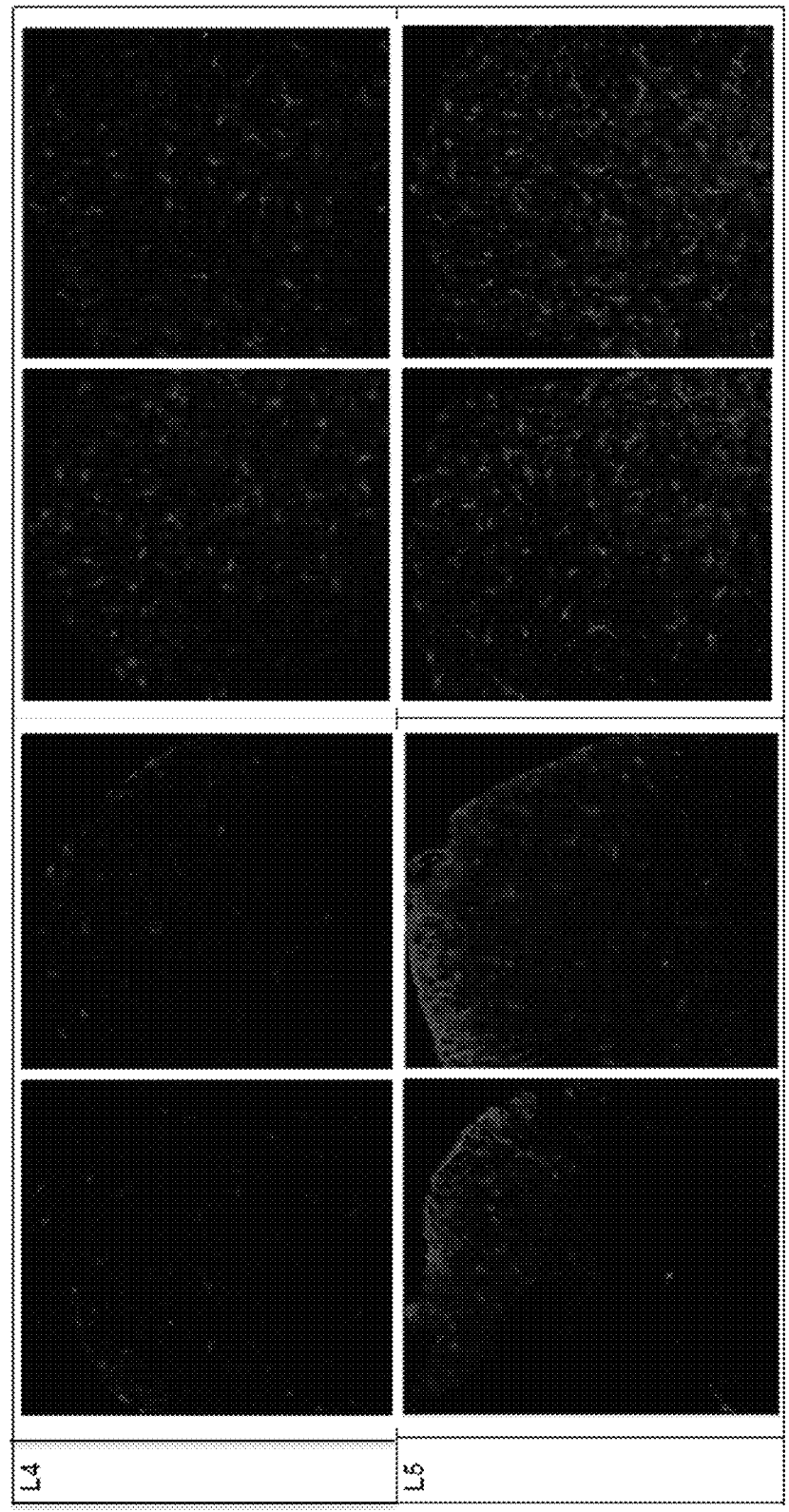
Figure 7C:
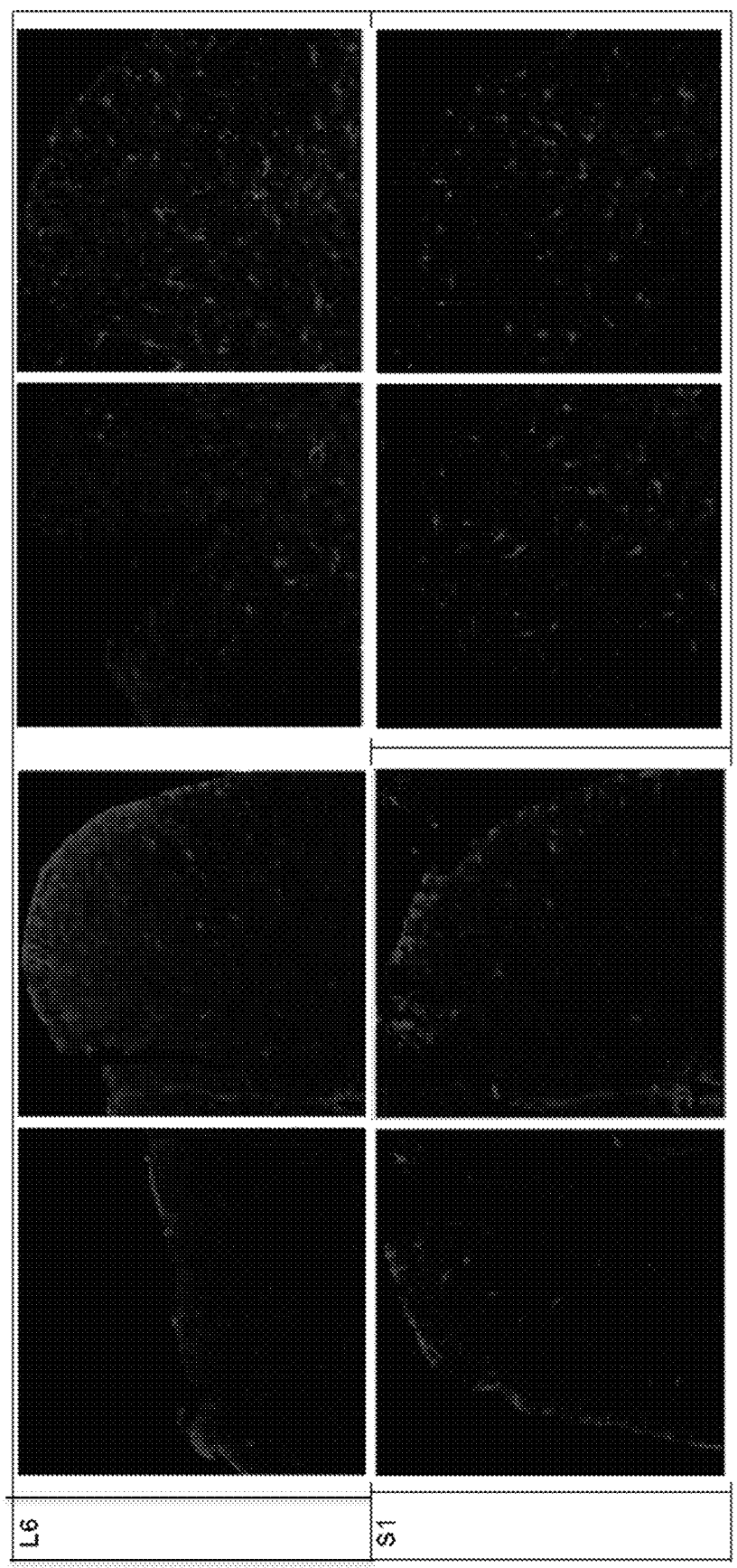
Figure 7D:
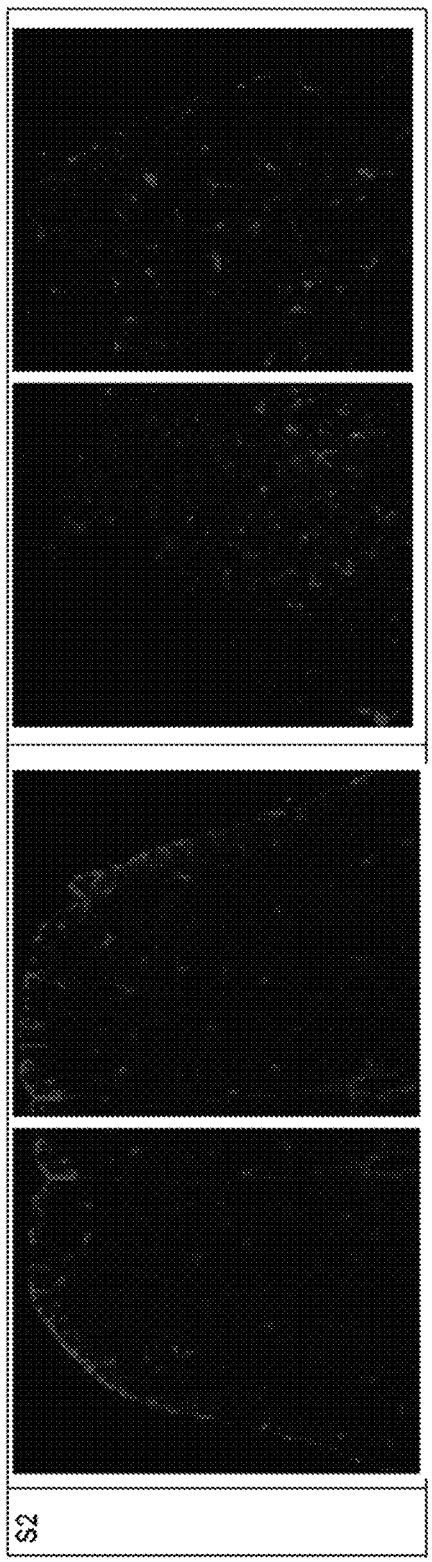
Figure 8B:
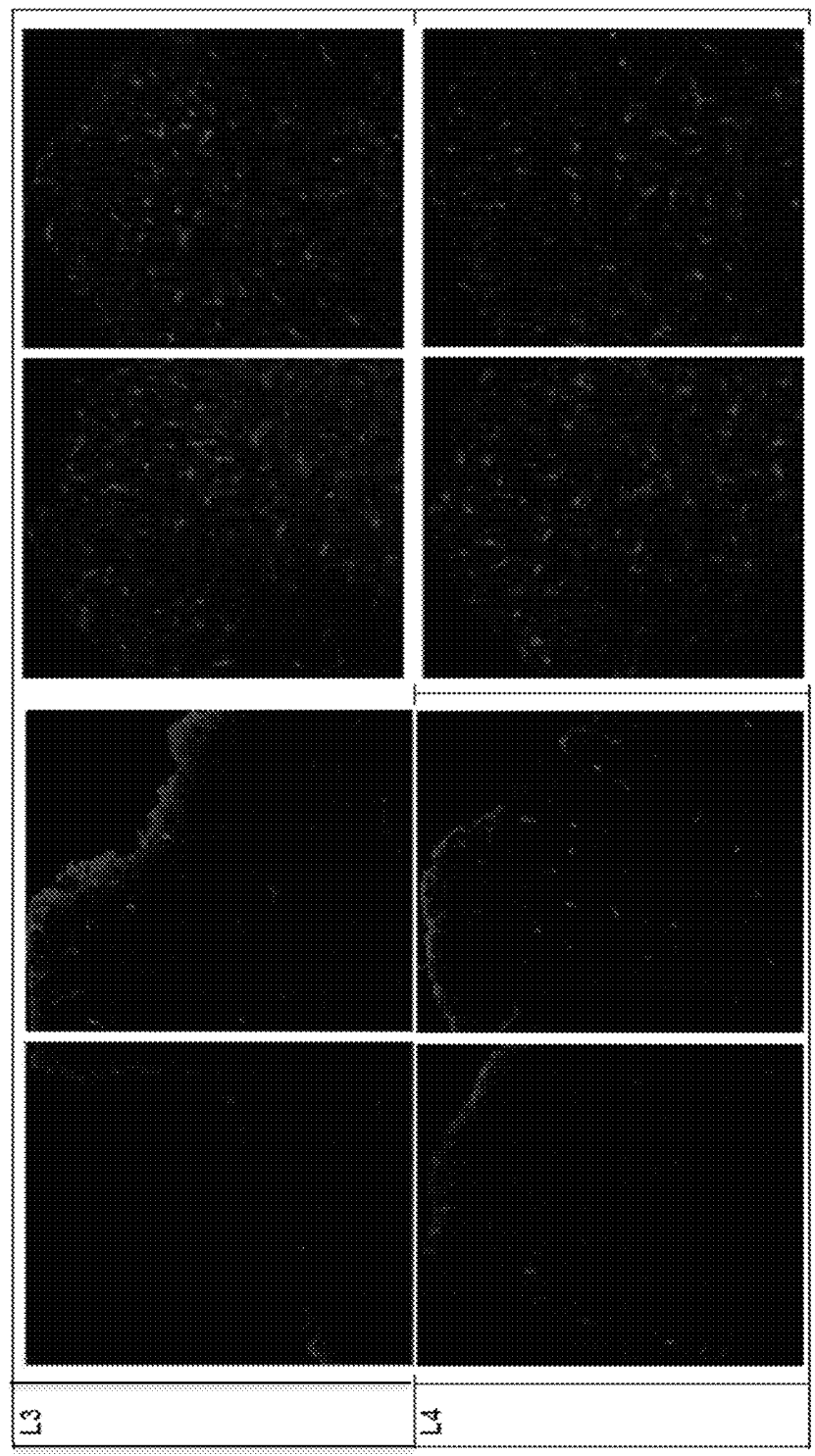
Figure 8C:
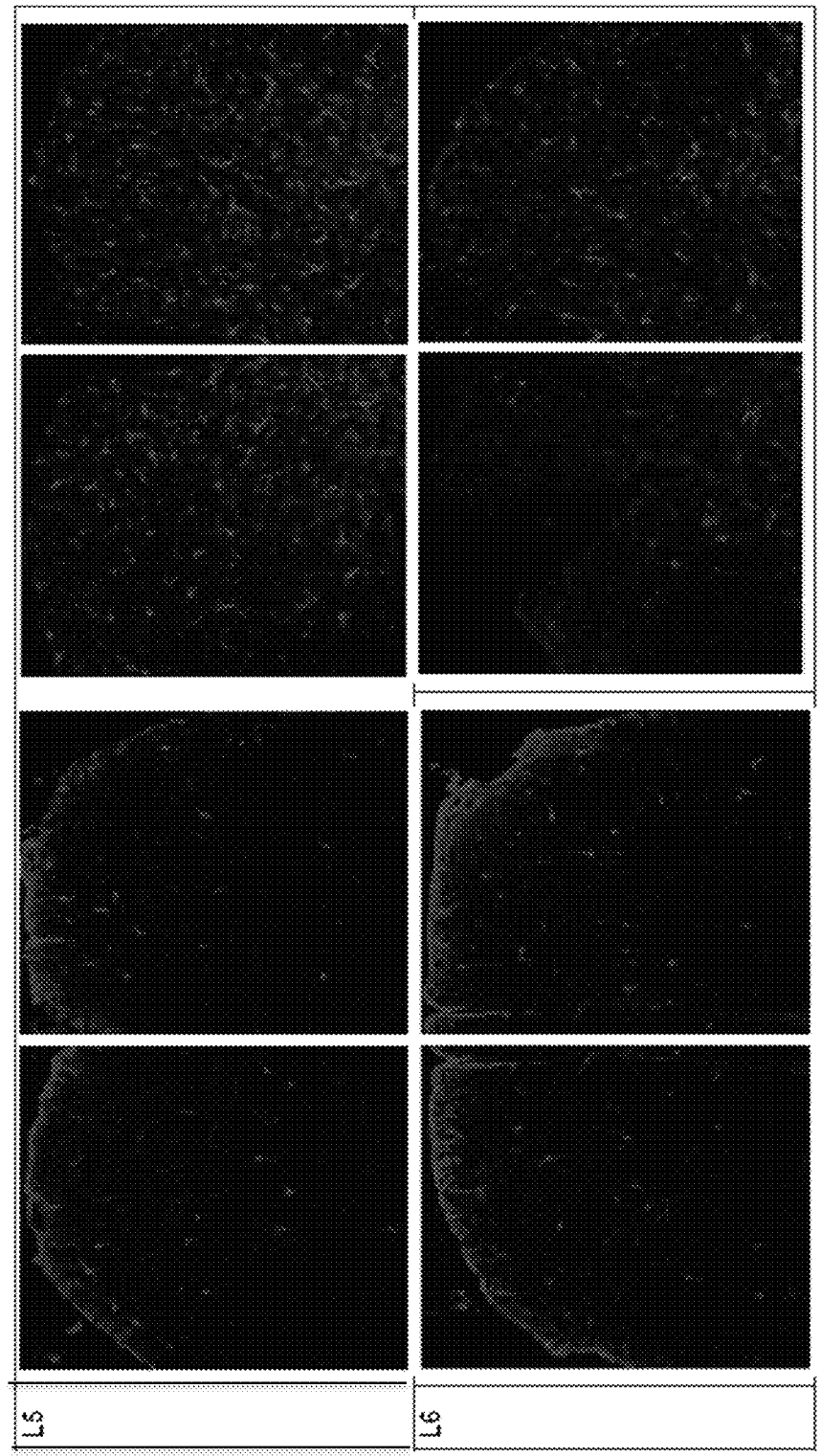
Figure 8D:
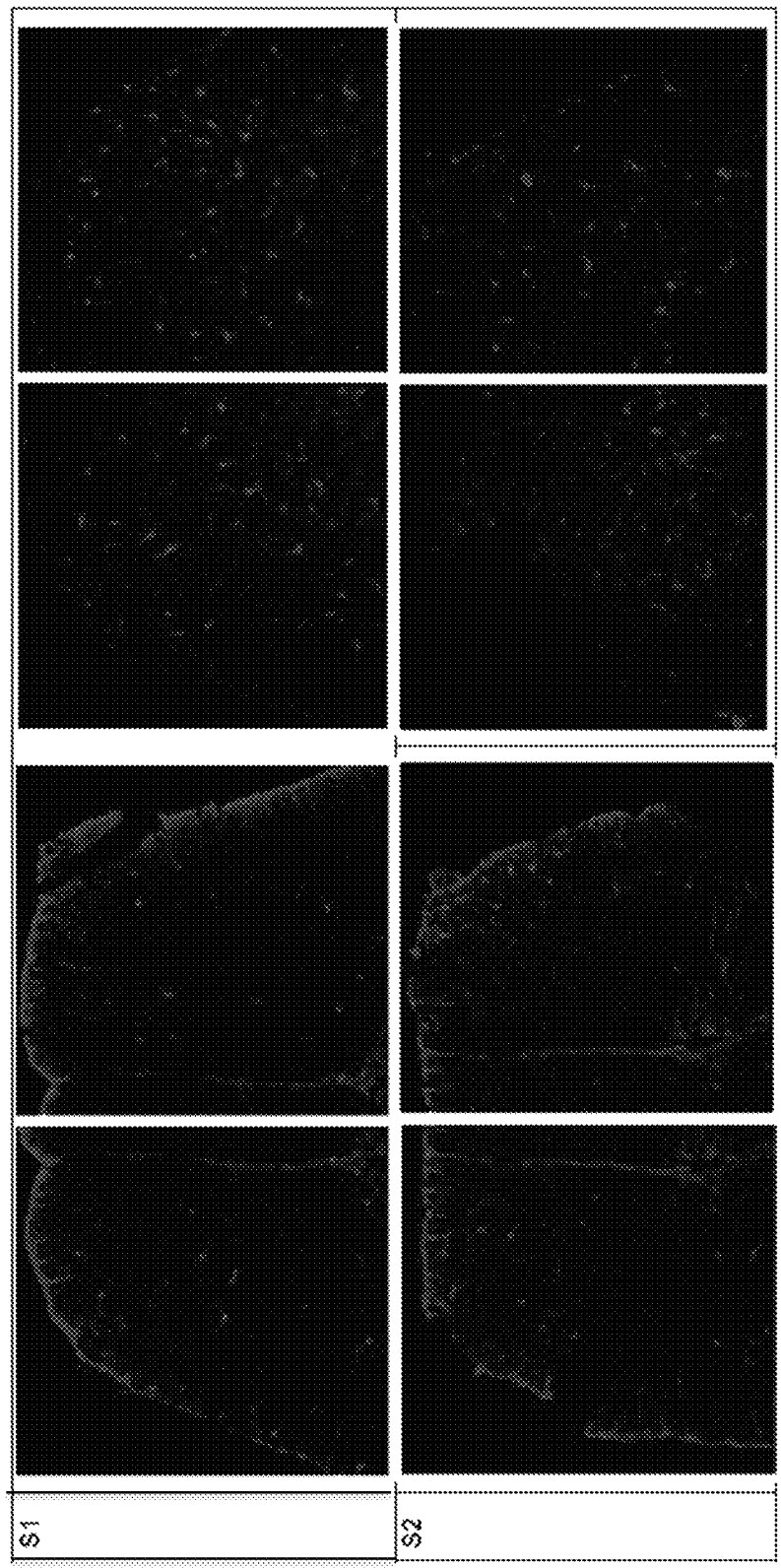

The regions of interest in the dorsal horn include Laminae I, II, III and IV, which are FIG. 2. Fluorescent staining was displayed by glial cells when activated. Changes in spinal glial reactivity are causally linked to all known models of exaggerated pain.

The data is shown in FIGS. 3A to 8D.

FIGS. 3A-3F show staining with GFAP in saline or LPS treated mice in multiple levels of the spinal cord. In these figures, the left hand side panel show treatment with saline, while the right hand panels show treatment with LPS. The staining shown in the figures was indicative of the staining in fluorescent green found using this maker.

FIGS. 4A-4E show intrauterine LPS induced a localised increase in Iba1 microglial staining throughout select levels of the spinal cord. In these figures, the left hand side panel show treatment with saline, while the right hand panels show treatment with LPS. The staining shown in the figures was indicative of the staining in fluorescent red found using this maker.

FIGS. 5A-5D show TAK242 treatment blocks the impact of intrauterine LPS at multiple levels of the spinal cord and reduced astrocytic reactivity to below basal levels, using staining for GFAP. In these figures, the left hand side panels show treatment with TAK242 and LPS, while the right hand panels show treatment with LPS. The staining shown in the figures was indicative of the staining in fluorescent green found using this maker.

FIGS. 6A-6D show amitriptyline treatment blocks the impact of intrauterine LPS at multiple levels of the spinal cord and reduced astrocytic reactivity to below basal levels using staining with GFAP. In these figures, the left hand side panels shows treatment with amitriptyline and LPS, while the right hand panels show treatment with LPS. The staining shown in the figures was indicative of the staining in fluorescent green found using this maker.

FIGS. 7A-7D show TAK242 treatment blocks the impact of intrauterine LPS at multiple levels of the spinal cord and reduced microglia reactivity to basal levels using staining for Iab1. In these figures, the left hand side panels show treatment with TAK242 and LPS, while the right hand panels show treatment with LPS. The staining shown in the figures is indicative of the staining in fluorescent red found using this maker.

FIGS. 8A-8D show amitriptyline treatment blocks the impact of intrauterine LPS at multiple levels of the spinal cord and reduced microglial reactivity to basal levels. In these figures, the left hand side panels show treatment with amitriptyline and LPS, while the right hand panels show treatment with LPS. The staining shown in the figures is indicative of the staining in fluorescent red found using this maker.

The results show that intrauterine LPS induced a substantial increase in GFAP astrocyte staining throughout multiple levels of the spinal cord, when compared with saline controls, and that amitriptyline treatment blocked the impact of intrauterine LPS at multiple levels of the spinal cord and reduced astrocytic reactivity to below basal levels. TAK242 treatment blocked the impact of intrauterine LPS at multiple levels of the spinal cord and reduced astrocytic reactivity to below basal levels.

Intrauterine LPS induced a localised increase in Iba1 microglial staining throughout select levels of the spinal cord. Amitriptyline treatment blocked the impact of intrauterine LPS at multiple levels of the spinal cord and reduced microglial reactivity to basal levels. TAK242 treatment blocked the impact of intrauterine LPS at multiple levels of the spinal cord and reduced microglia reactivity to basal levels.

These results demonstrate the ability of intra-uterine LPS to activate spinal glial cells, including astrocytes and microglia. This effect was prevented by the co-administration of amitriptyline. This effect was also prevented by the co-administration of TAK-242 demonstrating that spinal glial activation is mediated by activation of TLR4 receptors.

Figure 9:
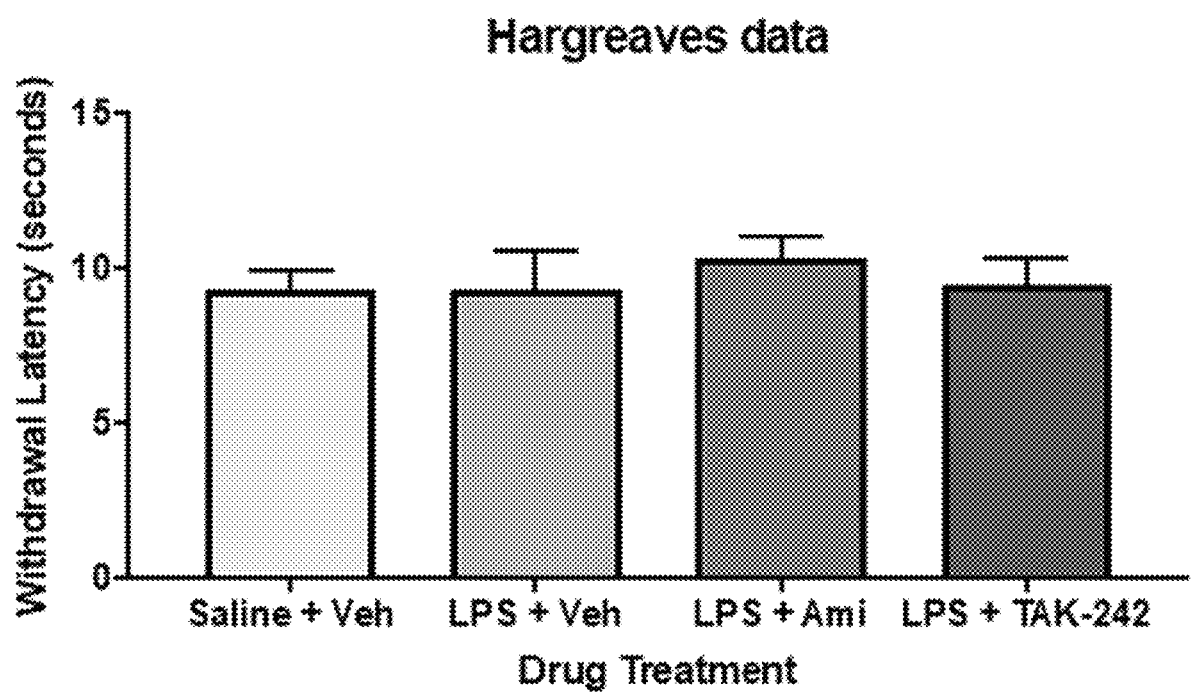
FIG. 9 shows behavioural assessment of animals with treatment with saline, LPS, LPS and amitriptyline, and LPS and TAK242 using thermal sensitivity of the animals' hind paws on the Hargreaves test.
Figure 10:
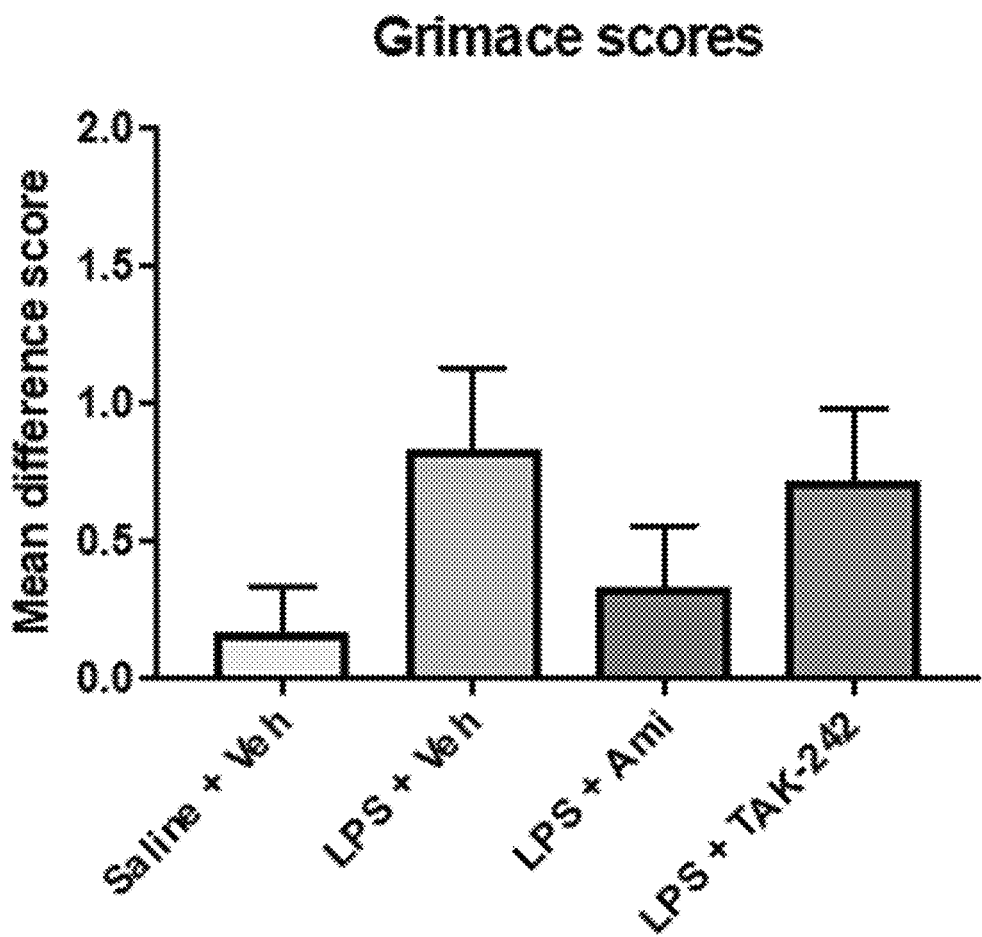
FIG. 10 shows grimace scores of animals treated with saline, LPS, LPS in conjunction with amitriptyline or LPS in conjunction with TAK242.

FIGS. 9 and 10 show behavioural assessment of animals with treatment with saline, LPS, LPS and amitryptiline, LPS and TAK-242. There was no main effect of treatment on the thermal sensitivity of the animals hind paws on the Hargreaves test (FIG. 9). However, LPS caused a significant increase in the presentation of Grimace behaviours in animals (FIG. 10). Amitriptyline reduced these scores, but TAK242 did not.

Example 3—Determination of the Innate Immune Receptors that can Reduce Spinal Glial Activation when Used within the Uterus The ability of intrauterine TAK-242 to block spinal glial activation following intrauterine administration of LPS confirms the role of TLR4 in this process. Amitriptyline showed additional activity reducing spinal glial activation above TAK-242 alone.

To investigate the range of pattern recognition receptors antagonized by amitriptyline, research was undertaken with 3 aims:

1. To determine the human Toll-Like Receptors which are agonized by lipopolysaccharide (LPS), and thus able to increase activation of glia within the dorsal horn of the spinal cord
2. To determine the human pattern recognition receptors antagonized by amitriptyline (Ami), and thus able to reduce activation of glia within the dorsal horn of the spinal cord. Tested pattern recognition receptors included Toll-Like Receptors 2, 3, 4, 5, 7, 8, and 9, NOD-Like Receptors (NLR) NOD1 and NOD2, C-Type Lectin Receptor (CLR) (Dectin-1a, Dectin-1b), RIG-I and MDA-5.
3. To confirm the ability of LPS to agonize, and amitriptyline to antagonize TLR4 receptors in human cells.

The range of Toll-Like Receptors antagonized by nortriptyline, a metabolite of amitriptyline, was also investigated.

Description:

Toll-Like Receptor (TLR), NOD-Like Receptor (NLR) and C-Type Lectin Receptor (CLR) stimulation were tested by assessing NF-κB activation in HEK293 cells expressing a given TLR, NLR or CLR. The activity of the test articles was tested at one concentration and compared to control ligands. These steps were performed in triplicate.

RIG-I and MDA-5 stimulation were tested by assessing IRF3 activation in HEK293 cells expressing human RIG-I or MDA-5 genes. The activity of the test articles was tested on human RIG-I and MDA-5 expressing cells as a potential agonist or antagonist. The test articles were evaluated at one concentration and compared to control ligands. This step was performed in triplicate. The results are provided as Relative Luminescence Units (RLUs).

Control Ligands:

TLR2: HKLM (heat-killed *Listeria monocytogenes*) at $1 \times 10^8$ cells/mL. Antagonist: $1 \times 10^6$ cells/mL:

hTLR3: Poly(I:C) HMW at 1 µg/mL Antagonist: 50 ng/mL.

hTLR4: *E. coli* K12 LPS at 100 ng/mL Antagonist: 10 ng/mL.

hTLR5: *S. typhimurium* flagellin at 100 ng/mL Antagonist: 50 ng/mL.

hTLR7: CL307 at 1 µg/mL Antagonist: 10 ng/mL.

hTLR8: CL075 at 1 µg/mL Antagonist: 200 ng/mL.

hTLR9: CpG ODN 2006 at 1 µg/mL Antagonist: 500 ng/mL.

hNOD1: C12-iE-DAP at 1 µg/mL Antagonist: 100 ng/mL.

hNOD2: L18-MDP at 100 ng/mL Antagonist: 50 ng/mL.

hDectin-1a and hDectin-1b: WGP Soluble (0-glucan from *S. cerevisiae*) at 10 ng/mL Antagonist: 5 ng/mL. Curdlan at 100 µg/mL. Antagonist: 100 µg/mL. Zymosan Depleted (hot alkali treated *S. cerevisiae*) at 5 µg/mL Antagonist: 3 µg/mL.

hMincle: Trehalose-6,6-dibehenate (TDB) at 10 µg/mL Antagonist: 5 µg/mL.

RIG-I/MDA-5: Poly(I:C)/LyoVec at 1 µg/mL Antagonist: 500 ng/mL. 5'ppp-dsRNA/LyoVec at 1 µg/mL Antagonist: 500 ng/mL. hIFNα at 1000 IU/mL. Antagonist: 100 IU/mL.

RIG-I$^-$/MDA-5$^-$ Cell Lines: HEK293/Null: Control for human RIG-I and MDA-5 Poly(I:C)HMW/LyoVec at 1 µg/mL. Antagonist: 500 ng/mL 5'ppp-dsRNA/LyoVec at 1 µg/mL. Antagonist: 500 ng/mL hIFNα at 1000 IU/mL. Antagonist: 100 IU/mL.

General Procedure:

TLR/NLR/CLR

In a 96-well plate (200 µL total volume) containing the appropriate cells (50,000-75,000 cells/well), 20 µL of the test article or the positive control ligand was added to the wells. For the antagonist assay, the test article was incubated with the cells, at 37° C. with 5% $CO_2$, for 30 minutes prior to the addition of the positive control ligand to the wells. The media added to the wells was designed for the detection of NF-κB induced SEAP expression. After a 16-24 hr incubation the optical density (OD) was read at 650 nm on a Molecular Devices SpectraMax 340PC absorbance detector.

RIG-I/MDA-5

In a 96-well plate (200 µL total volume) containing the appropriate cells (25,000-50,000 cells/well), 20 µL of the test article or of the positive control ligand was added to the wells. For the antagonist assay, the test article was incubated with the cells, at 37° C. with 5% $CO_2$, for 30 minutes prior to the addition of the positive control ligand to the wells. After 20 hour incubation, activation of the IRF pathway was monitored using a luciferase detection assay. Luciferase activity was assayed in triplicate from the supernatant of the induced cells, and the relative luminescence units (RLUs) are detected by a Promega GloMax Luminometer.

Results:

Human TLR and NLR Agonist Screening:

The fold induction (ratio of average induced value to average non-induced value) results were as follows:

| TLR/NLR Cell Line | Control− | LPS-EB 20 ng/mL | Control+ |
|---|---|---|---|
| hTLR2 | 1 | 10 | 17 |
| hTLR3 | 1 | 1 | 17 |
| hTLR4(MD2-CD14) | 1 | 14 | 16 |
| hTLR5 | 1 | 1 | 18 |
| hTLR7 | 1 | 1 | 34 |
| hTLR8 | 1 | 1 | 19 |
| hTLR9 | 1 | 1 | 18 |
| hNOD1 | 1 | 1 | 20 |
| hNOD2 | 1 | 1 | 10 |

Human TLR/NLR Cell lines: hTLR2: HKLM (heat-killed *Listeria monocytogenes* $1×10^8$ cells/mL. hTLR3: Poly(I:C) HMW at 1 µg/mL. hTLR4 (MD2-CD14): *E. coli* K12 LPS at 100 ng/mL. hTLR5: *S. typhimurium* flagellin at 100 ng/mL. hTLR7: CL307 at 1 µg/mL. hTLR8: CL075 at 1 µg/mL. hTLR9: CpG ODN 2006 at 1 µg/mL hNOD1: C12-iE-DAP at 1 µg/mL hNOD2: L18-MDP at 100 ng/mL Human CLR, RLR, Agonist Screening:

Fold Induction (Ratio of Average Induced Value to Average Non-Induced Value):

| CLR Cell Line | Control− | LPS-EB 20 ng/mL | WGP Soluble 10 ng/mL | Curdlan 100 µg/mL | Zymosan Depleted 5 µg/mL |
|---|---|---|---|---|---|
| hDectin-1a | 1 | 1 | 14 | 6 | 15 |
| hDectin-1b | 1 | 1 | 1 | 8 | 26 |

RIG-1

| Control− | LPS-EB 20 ng/mL | Poly(I:C)/ LyoVec 1 µg/mL | 5'ppp-dsRNA/ LyoVec 1 µg/mL | hIFNα 1000 IU/mL |
|---|---|---|---|---|
| 1 | 1 | 11 | 31 | 169 |

MDA-5

| Control− | LPS-EB 20 ng/mL | Poly(I:C)/ LyoVec 1 µg/mL | 5'ppp-dsRNA/ LyoVec 1 µg/mL | hIFNα 1000 IU/mL |
|---|---|---|---|---|
| 1 | 1 | 5 | 1 | 2 5 2 |

Human TLR Antagonist Screening:

Fold induction (ratio of average induced value to average non-induced value) was determined for each TLR, NOD1, NOD2, Dectin-1a, Dectin-1b.

| | | +HKLM 1 × 10^6 cells/mL | | |
|---|---|---|---|---|
| | Human TLR2 | Ami 1 | Nor 1 | No |
| | Control− | µM | µM | Sample |
| Fold Induction* | 1 | 5 | 5 | 6 |

| | | +Poly(I:C) 50 ng/ml | | |
|---|---|---|---|---|
| | Human TLR3 | Ami 1 | Nor 1 | No |
| | Control− | µM | µM | Sample |
| Fold Induction* | 1 | 12 | 12 | 14 |

-continued

| Human TLR4 | | +LPS-EK 10 ng/mL | | |
|---|---|---|---|---|
| | Control⁻ | Ami 1 μM | Nor 1 μM | No Sample |
| Fold Induction* | 1 | 12 | 14 | 14 |

| Human TLR5 | | +FLA-ST 50 ng/ml | | |
|---|---|---|---|---|
| | Control⁻ | Ami 1 μM | Nor 1 μM | No Sample |
| Fold Induction* | 1 | 33 | 34 | 34 |

| Human TLR7 | | +CL307 10 ng/ml | | |
|---|---|---|---|---|
| | Control⁻ | Ami 1 μM | Nor 1 μM | No Sample |
| Fold Induction* | 1 | 16 | 16 | 13 |

| Human TLR8 | | +CL075 200 ng/ml | | |
|---|---|---|---|---|
| | Control⁻ | Ami 1 μM | Nor 1 μM | No Sample |
| Fold Induction* | 1 | 11 | 11 | 13 |

| Human TLR9 | | +ODN 2006 500 ng/ml | | |
|---|---|---|---|---|
| | Control⁻ | Ami 1 μM | Nor 1 μM | No Sample |
| Fold Induction* | 1 | 6 | 6 | 7 |

| Human NOD1 | | +C12-iE-DAP 100 ng/mL | |
|---|---|---|---|
| | Control⁻ | Ami 1 μM | No Sample |
| Fold Induction* | 1 | 9 | 10 |

| Human NOD2 | | +L18-MDP 50 ng/mL | |
|---|---|---|---|
| | Control⁻ | Ami 1 μM | No Sample |
| Fold Induction* | 1 | 17 | 18 |

| Human Dectin-1a | | +WGP Soluble 5 ng/mL | | +Curdlan 100 μg/mL | | +Zymosan Depleted 3 μg/mL | |
|---|---|---|---|---|---|---|---|
| | Control⁻ | Ami 1 μM | No Sample | Ami 1 μM | No Sample | Ami 1 μM | No Sample |
| Fold Induction* | 1 | 8 | 8 | 4 | 5 | 4 | 6 |

-continued

| Human Dectin-1b | +WGP Soluble 5 ng/mL | | +Curdlan 100 µg/mL | | +Zymosan Depleted 3 µg/mL | |
|---|---|---|---|---|---|---|
| | Ami 1 | No | Ami 1 | No | Ami 1 | No |
| Control⁻ | µM | Sample | µM | Sample | µM | Sample |
| Fold Induction* | 1 | 1 | 1 | 4 | 4 | 6 | 7 |

| Human Mincle | +TDB 5 µg/mL | |
|---|---|---|
| | Ami 1 | No |
| Control⁻ | µM | Sample |
| Fold Induction* | 1 | 5 | 6 |

Human RLR Antagonist Screening:
Fold induction (ratio of average induced value to average non-induced value).
RIG-I

| | Poly(I:C)/ LyoVec 500 ng/mL | | 5'ppp-dsRNA/ LyoVec 500 ng/mL | | hIFNa 100 IU/mL | |
|---|---|---|---|---|---|---|
| Control⁻ | Ami 1 µM | No Sample | Ami 1 µM | No Sample | Ami1 µM | No Sample |
| 1 | 16 | 16 | 6 | 6 | 82 | 108 |

MDA-5

| | Poly(I:C)/ LyoVec 500 ng/mL | | 5'ppp-dsRNA/ LyoVec 500 ng/mL | | hIFNα 100 IU/mL | |
|---|---|---|---|---|---|---|
| Control⁻ | Ami 1 µM | No Sample | Ami 1 µM | No Sample | Ami 1 µM | No Sample |
| 1 | 10 | 9 | 1 | 1 | 192 | 255 |

Summary of Results:
Human TLR/NLR
Test Article LPS-EB exhibits a significant stimulatory effect on human TLR2 and TLR4.
Test Article Amitriptyline exhibits a slight inhibitory effect on human TLR2, 3, 4, 5, 8, 9, NOD1 and NOD2 stimulated with their respective positive control ligands. In addition, Amitriptyline exhibits a slight inhibitory effect on TLR⁻/NLR⁻ control cell lines HEK293/Null1 and HEK293/Null2 when stimulated with TNFa at 10 ng/mL. The inhibitory effect observed on the negative control cell lines indicates that the inhibitory effect observed on human TLR2, 3, 4, 5, 8, 9, NOD1 and NOD2 may not be due to TLR/NLR specific inhibition. Test article Amitriptyline exhibits a slight potentiating effect on human TLR7.
Test Article Nortriptyline exhibits a slight inhibitory effect on human TLR2, 3, 8 and 9 stimulated with their respective positive control ligands. In addition, Nortriptyline exhibits a slight inhibitory effect on TLR⁻/NLR⁻ control cell lines HEK293/Null1 and HEK293/Null2 when stimulated with TNFa at 10 ng/mL. The inhibitory effect observed on the negative control cell lines indicates that the inhibitory effect observed on human TLR2, 3, 8 and 9 may not be due to TLR specific inhibition. Test article Nortriptyline exhibits a slight potentiating effecton human TLR7.
Human CLR
Test Article LPS-EB does not exhibit a stimulatory effect on human Dectin-1a, or Dectin-1b or Mincle.
Test Article Amitriptyline exhibits a slight inhibitory effect on human Dectin-1a when stimulated with Curdlan at 100 µg/mL and Zymosan Depleted at 3 µg/mL. In addition, Amitriptyline exhibits a slight inhibitory effect on human Dectin-1b when stimulated with Zymosan Depleted at 3 µg/mL. Amitriptyline also exhibits a slight inhibitory effect on human Mincle when stimulated by TDB at 5 µg/mL.
Human RLR
Test Article LPS-EB does not exhibit a stimulatory effect on human RIG-I or MDA-5.
Test Article Amitriptyline exhibits an inhibitory effect on human RIG-I, MDA-5 and RIG-I⁻/MDA-5⁻ control cell line HEK293/Null when stimulated with recombinant hIFNα at 100 IU/mL. The inhibitory effect observed on the negative control cell line (and only on recombinant hIFNα) indicates that the antagonistic effect observed is not due to specific RIG-I or MDA5 inhibition.
Conclusion:
In summary, the testing has shown that amitriptyline and nortriptyline provide broad inhibition of TLR, CLR and RLR receptors, and are likely to provide a beneficial effect to reduce immune activation within the uterus.

Example 4—Intra-Vaginal Administration of a TLR4 Antagonist (Amitriptyline) can Reduce Post IUCD Insertion Pain in Women A study may be undertaken to assess the ability of an agent that reduces activation of the innate immune system to reduce pain following insertion of a levonorgestrel-releasing intra-uterine device into women.
For example, a double-blinded study may be undertaken to assess the ability of an agent that inhibits Toll-like receptor 4 (TLR4), such as a TLR4 antagonist, to reduce pain following insertion of a levonorgestrel-releasing intra-uterine device to women.
Following insertion of the device, each woman will be subject to a daily vaginal suppository comprising either a low dose of TLR4 antagonist (amitriptyline) or placebo. Pain outcomes will be measured by self-reported pain scales, and by assessing the analgesic requirement for both groups.

Methods for producing vaginal suppositories are known in the art. Vaginal suppositories containing either 1.7 mg of amitriptyline or vehicle only will be sourced from a compounding pharmacy. Suppositories will be prepared, randomised and numbered by the pharmacist with master code kept in a locked facility by the pharmacist at the compounding laboratory.

Outcome measures will be assessed by VAS pain score, quality of life questionnaire, and patient satisfaction with the device following insertion. It is anticipated that intra-vaginal administration of a TLR4 antagonist (Amitriptyline) will reduce post IUCD insertion pain in women.

Example 5—Intra-Vaginal Administration of a TLR4 Antagonist (Amitriptyline) can Reduce Pain Associated with Dysmenorrhea in Women A study may be undertaken to assess the ability of an agent that reduces activation of the innate immune system to reduce pain in women associated with dysmenorrhea.

For example, a double-blinded study may be undertaken to assess the ability of an agent that inhibits Toll-like receptor 4 (TLR4), such as a TLR4 antagonist, administered as a vaginal suppository, to reduce pain associated with dysmenorrhea.

Women with pelvic pain associated with dysmenorrhea will be subject to a daily vaginal suppository comprising either a low dose (1.7 mg) of TLR4 antagonist (amitriptyline) or placebo.

Pain outcomes will be measured by self-reported pain scales, and by assessing the analgesic requirement for both groups. Outcome measures will be assessed by VAS pain score and quality of life questionnaire.

It is anticipated that intra-vaginal administration of a TLR4 antagonist (Amitriptyline) will reduce pain, and pain related symptoms associated with dysmenorrhea in women.

Example 6—Enhanced Treatment of a Woman with Heavy Menstrual Bleeding and Dysmenorrhea, Who would Like to Use a Progestogen-Releasing Intra-Uterine Device but is Concerned Regarding a Potential Increase in Pain Following Insertion of the Device In this example, a young woman (e.g. 20 years old) suffering from dysmenorrhea for 3 days per month, who does not wish to use the oral contraceptive pill, and requests insertion of a levonorgestrel-releasing intra-uterine device for symptom management, may be selected.

While the device has a high clinical probability of relieving dysmenorrhea, insertion of an intrauterine device may increase pain in the months after insertion with between 4-14% of devices removed over this time due to pain.

Insertion of a levonorgestrel-releasing intrauterine device also loaded with an added agent that inhibits a Toll-like receptor 4 (TLR4, such as a TLR4 antagonist, is expected to reduce post IUCD insertion pain, with reduced request for post insertion removal of the device due to pain. The production of an intrauterine device able to release a TLR4 antagonist is described herein.

Example 7—Treatment of a Patient with Pelvic Pain Associated with Dysmenorrhea

A young woman (e.g. 20 years old) with dysmenorrhea occurring since soon after first menarche may be selected. Dysmenorrhea will typically have been present for 3 days per month, with good health in between periods. The woman may have developed pain for a week leading up to her period, with a different sharp pain, stabbing pain at other times of her menstrual cycle.

An intrauterine device comprising a progestogen medication, such as levonorgestrel, and an agent that reduces activation of the innate immune system may be inserted in the uterus.

Figure 11:
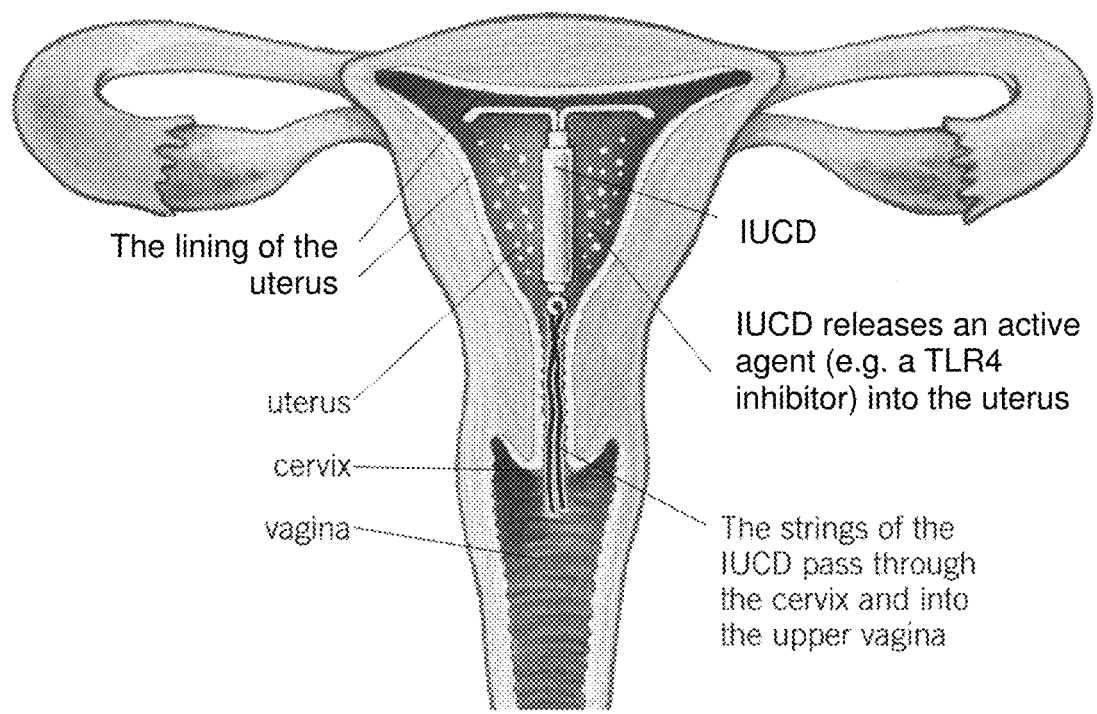
FIG. 11 shows a representation of the pelvic organs with an intrauterine device according to certain exemplary embodiments for releasing a TLR4 antagonist within the uterine cavity. The intra-uterine device includes a drug reservoir attached to the shaft of the device, providing slow release of TLR4 antagonist to the endometrial cavity of the uterus.

For example, an intrauterine device comprising a progestogen medication, such as levonorgestrel, and an agent that inhibits Toll-like receptor 4 (TLR4) such as a TLR4 antagonist (eg amitriptyline), will be inserted in the uterus. An example of such a device is shown in FIG. 11. Methods for producing a device are as described herein.

It is anticipated that the levonorgestrel will reduce menstrual blood loss and assist with reducing pain present at menstruation, and that amitriptyline will reduce the pain prior to menstruation and pain present at other times of her menstrual cycle.

Example 8—Treatment of a Patient with Pelvic Pain Associated with Dysmenorrhea

A suitable patient for treatment by way of intrauterine delivery of an agent that reduces spinal glial activation may be selected.

For example, a patient suitable for prevent or management with an intrauterine device for long-term release of an agent that inhibits Toll-like receptor 4 (TLR4) may be selected as described in Example 6.

In a patient presenting with pelvic pain, clinical evaluation may be undertaken to arrive at an assessment of pelvic pain associated with dysmenorrhea. As demonstrated in Example 1, it is common for women with dysmenorrhea to also suffer irritable bowel symptoms, painful bladder symptoms, pelvic muscle pain, and pain associated with intercourse.

For a patient selected for treatment, local pelvic administration of an agent that inhibits Toll-like receptor 4 (TLR4) may be selected by a medical practitioner.

For example, daily local pelvic administration of a TLR4 antagonist (such as amitriptyline, naltrexone or TAK-242) may be undertaken.

For example, a chitosan and sodium alginate based bioadhesive gel containing the active agent may be prepared as described in Richardson J. L, and. Illum L (1992) *Adv. Drug Deliv. Rev.* 8: 341-366 and administered to the uterine cavity of the patient by way of an applicator. The gel may contain a dose of 1 to 5 mg of amitriptyline and/or 50 mg to 100 mg of naltrexone.

The treatment regime may be continued for a suitable length of time, for example 4 to 8 weeks or otherwise as determined by a medical practitioner.

Alternatively, a vaginal suppository containing the same amounts of a TLR4 antagonist may be used to administer the agents, or an intrauterine device for administering a TLR4 antagonist as described in Example 8 may be used Efficacy of the treatment may be evaluated by assessing a variety of suitable clinical parameters, such as the use of established and validated pain scales.

Example 9—an Intrauterine Device for Preventing the Transition to Persistent Pelvic Pain in a Patient Suffering from Dysmenorrhea A patient suitable for prevention of pelvic pain with an intrauterine device providing long-term release of an agent that reduces activation of the innate immune system may be selected.

For example, a patient with dysmenorrhea suitable for prevention of pelvic pain with an intrauterine device providing long-term release of an agent that inhibits Toll-like receptor 4 (TLR4) (such as a TLR4 antagonist) may be selected as described in Example 6.

The intrauterine device provides a delivery system for long-term release of an agent that inhibits a Toll-like receptor 4 (TLR4), thereby administering the active agent to the patient.

Intrauterine devices for administering active agents are known in the art, for example as described in US Patent Application No. 20140127280.

For example, the intrauterine device may utilise a body construction with a core reservoir comprising a TLR4 antagonist, and optionally a membrane encasing the core, made from a suitable polymer. The polymer may be selected on the desired release rates of the active agents.

The polymer composition of the core and/or the membrane can be chosen so that the intrauterine system releases a sufficient predetermined amount of a TLR4 antagonist.

A membrane may cover the whole or part of the reservoir to further control the release rate of the active agent(s). The polymer composition used in the membrane is such that it allows the pre-determined, constant release rates of the active agent(s). The composition and/or thickness of the membrane may be selected upon the desired release profile of the active agent(s), and may have one or more layers.

The polymer in the core and/or the membrane is generally selected to have high biocompatibility.

The release kinetics of an active agent from a polymer based delivery system depends on a variety of characteristics such as the molecular weight, solubility, diffusivity and charge of the therapeutically active agent, as well as on the characteristics of the polymer, the loading of the therapeutically active agent, the distance the therapeutically active agent must diffuse through the device to reach its surface and on the characteristics of any matrix or membrane.

Polysiloxanes, such as poly(dimethyl siloxane) (PDMS), may be to regulate the release rate of active agents. Polysiloxanes are physiologically inert, and a wide group of active agents are capable of penetrating polysiloxane membranes, which also suitable strength properties. The release rate of active agent(s) can be adjusted as a desired by modifying the polymeric material in a suitable way, e.g. by adjusting hydrophilic or hydrophobic properties of the material. For example, addition of poly (ethylene oxide) groups or trifluoropropyl groups to a PDMS polymer may change the release rate of active agents.

Further examples of suitable materials include, copolymers of di-methylsiloxanes and methylvinylsiloxanes, ethylene/vinyl acetate copolymers (EVA), polyethylene, polypropylene, ethylene/propylene copolymers, acrylic acid polymers, ethylene/ethyl acrylate copolymers, polytetrafluoroethylene (PTFE), polyurethanes, thermoplastic polyurethanes and polyurethane elastomers, polybutadiene, polyisoprene, poly(methacrylate), polymethyl methacrylate, styrene-butadiene-styrene block copolymers, poly(hydroxyethyl-methacrylate) (pHEMA), polyvinyl chloride, polyvinyl acetate, polyethers, polyacrylo-nitriles, polyethylene glycols, polymethylpentene, polybutadiene, polyhydroxy alkanoates, poly(lactic acid), poly(glycolic acid), polyanhydrides, polyorthoesters, hydrophilic polymers such as the hydrophilic hydrogels, cross-linked polyvinyl alcohol, neoprene rubber, butyl rubber, hydroxyl-terminated organopolysiloxanes, and copolymers of the aforementioned.

The core or the membrane may also comprise additional materials to further adjust the release rate of the active agent(s), for example complex forming agents such as cyclodextrin derivatives to adjust an initial release of the active agent to the accepted or desired level.

In one embodiment, the core and the membrane are made of a siloxane based elastomer composition comprising at least one elastomer and optionally a non-crosslinked polymer. Siloxane-based elastomers include elastomers made of poly (disubstituted siloxanes) where the substituents mainly are lower alkyl, preferably alkyl groups of 1 to 6 carbon atoms, or phenyl groups, wherein the alkyl or phenyl can be substituted or unsubstituted. For example, poly(dimethylsiloxane) (PDMS) may be used.

Examples of elastomeric compositions include an elastomer composition comprising poly(dimethylsiloxane) (PDMS), an elastomer composition comprising a siloxane-based elastomer comprising 3,3,3-trifluoropropyl groups attached to the silicon atoms of the siloxane units, an elastomer composition comprising poly(alkylene oxide) groups, the poly(alkylene oxide) groups being present as alkoxy-terminated grafts or blocks linked to the polysiloxane units by silicon-carbon bonds or as a mixture of these forms, and one or more combinations of the above.

In one example, the siloxane-based elastomer comprises from 1 to approximately 50% of the substituents attached to the silicon atoms of the siloxane units as 3,3,3-trifluoropropyl groups. The percentage of the substituents that are 3,3,3-trifluoropropyl groups can be for example 5-40%, 10-35%, 1-29% or 15-49.5%.

In another example, the siloxane-based elastomer comprises poly(alkylene oxide) groups so that the poly(alkylene oxide) groups are present in the elastomer either as alkoxy-terminated grafts of polysiloxane units or as blocks, said grafts or blocks being linked to the polysiloxane units by silicon-carbon bonds. For example, poly(alkylene oxide) groups such as poly(ethylene oxide) (PEO) groups may be used.

Methods for the preparation of suitable polymers are provided, for example, in international patent applications WO 00/00550, WO 00/29464, WO 99/10412 and US Patent Application No. 20140127280.

Agents that inhibit Toll-like receptor 4 (TLR4) are as described herein.

The intrauterine device may also release other therapeutic agents, such as a sex hormone. For example, the sex hormone may be a progestogenic compound. Examples of progestogenic compounds include compounds such as progesterone and its derivatives, cyproterone acetate, dienogest, desogestrel, etonogestrel, levonorgestrel, lynestrenol, medroxyprogesterone acetate, norethisterone, norethisterone acetate, norgestimate, drospirenone, gestodene, 19-nor-17-hydroxy progesterone esters, 17α-ethinyltestosterone and derivatives thereof, 17α-ethinyl-19-nor-testosterone and derivatives thereof, ethynodiol diacetate, dydrogesterone, norethynodrel, allylestrenol, medrogestone, norgestrienone, ethisterone and dl-norgestrel.

The release of the active agent(s) may be selected to occur over a suitable period of time, for example from weeks to years.

The amount of the agent that inhibits Toll-like receptor 4 (TLR4) incorporated in the delivery system varies depending on the particular active agent and the time for which the intrauterine delivery system is expected to provide therapy.

The shape and size of the intrauterine device may be chosen by a person skilled in the art compatible with the dimensions of the uterine cavity. For example, an intrauterine delivery system may comprise a body forming the frame of the system and a reservoir containing the active agent(s)

attached on the body. One example is a T-shaped object fabricated of a biocompatible material and having an elongate member having at one end a transverse member comprising two arms, the elongate member and the transverse member forming a T-shaped piece when the system is positioned in the uterus. Reservoirs containing an active agent(s) can be attached to the elongate member, to the transverse member or members, or both to the elongate member and the transverse member(s). The manufacturing of such devices is known in the art.

For example, the body and the reservoir may be manufactured simultaneously or separately followed by their assembly. The body may be manufactured by injection moulding or compression moulding. The active agent containing cores may be manufactured by mixing the therapeutically active substance or substances within the core matrix material for example such as polydimethylsiloxane (PDMS, processed to the desired shape by moulding, casting, extrusion, or by other appropriate methods known in the art.

A membrane layer, if any, can be applied onto the core according to known methods such as by using extrusion or injection moulding methods, spraying or dipping. As an alternative, a prefabricated membrane tube may be expanded mechanically for example with a suitable device or by using for example pressurized gas, such as air, or by swelling it in a suitable solvent, such as cyclohexane, diglyme, isopropanol, or in a mixture of solvents, where after the swollen membrane tube is mounted onto the core. When the solvent evaporates, the membrane tightens on the core.

A reservoir containing the active agent(s) may be fixed on the frame by using a variety of different methods. The frame may for example comprise an elongated extension in the form of a polymer shaft, core, rod or pin or the like at a suitable point on which the hollow tube-like reservoir is assembled, for example by first enlarging the diameter of the reservoir tube to some degree, for example by using pressure or solvent swelling, and thereafter by simply sliding the reservoir onto the extension or inserting the extension into the hollow reservoir. It is also possible to assemble first the hollow tube-like core onto the body and then assemble the membrane onto the core. Other methods to attach the reservoir to the frame include for example known techniques of welding, use of an adhesive, or use of special metal or polymer inserts, clips, connectors, adapters, clothespin-type means or clamps.

If needed, one or each end of the reservoirs so obtained may be sealed by using known techniques, for example by applying a drop of an adhesive or silicon glue.

The intrauterine delivery system can also be manufactured by coating the body with the drug containing core material by using known technology, for example such as dipping, spraying, injection moulding and like.

The core can also be prepared for example by using a coextrusion method described in the Finnish patent FI 97947. The active agent(s) may be mixed within the core matrix polymer composition, and processed to the desired shape and size by using known extrusion methods.

The body of the system may further comprise locking means to keep the cores or reservoir in place during the insertion step, during the use of the device or during the removal of the device.

The delivery system can be manufactured in any size as required, the exact size being dependent on the patients and particular application. In practice, the dimensions of the delivery system should be close to the size of the uterine cavity. For a human female, the length of the IUS body is normally in the order of from 20 to 40 mm. in length, preferably from 25 to 38 mm and the width of the body is in the order of from 20 to 32 mm corresponding generally to the width of the fundal portion of the uterine cavity. The cross-sectional diameter of the body member is in the order of from 1 to 4 mm, preferably from 1.5 to 3 mm.

The length of the core of the delivery system will be chosen to give the required performance. The length of the reservoir as well as of a core segment can be for example from 1 to 35 mm and depends on the nature of the material.

The outer diameter of the core can be, for example, from 0.1 to 5.0 mm, and preferably from 0.2 to 3.5 mm. The thickness of the membrane encasing the core or core segment may be, for example, from 0.1 to 1.0 mm, preferably from 0.2 to 0.6 mm.

For example, 45 parts by weight of a TLR4 antagonist, levonorgestrel, 50 parts by weight of poly(dimethylsiloxane-co-vinylmethylsiloxane) and 1.2 parts by weight of dichlorobenzoylperoxide-polydimethylsiloxane paste (50% of dichlorobenzoylperoxide) may be mixed with a 2-roll mill. The mixture may be extruded to a tube-like form with a wall thickness of 0.8 mm and outer diameter of 2.8 mm and cured by heat for 15 minutes, during which crosslinking will take place. The crosslinked core may then be cut into 24 mm length.

In an alternative example, 54 parts of commercial poly(dimethylsiloxane-co-vinylmethylsiloxane), 45.5 parts by weight of a TLR4 antagonist, 0.4 parts of poly(hydrogenmethylsiloxane-co-dimethylsiloxane) crosslinker, 0.02 parts of ethynyl cyclohexanol inhibitor and 10 ppm of Pt-catalyst (of the reaction species) in vinyl-methyl-siloxane may be mixed in a kneading mill. The mixture may be extruded to a tube-like form with a wall thickness of 0.7 mm and cured by heat for 30 minutes and cooled.

The core may then be swollen in cyclohexane and pulled over the IUS body and cyclohexane allowed to evaporate.

The release rate of the agent that inhibits Toll-like receptor 4 (TLR4) from the implant may be determined in vitro. The intrauterine delivery system may be placed in a dissolution medium shaken at a suitable speed at 37° C. The dissolution medium may be withdrawn and replaced by a fresh dissolution medium at predetermined time intervals, and the amount of the released active agent analysed by using standard analytical methods.

Examples of a suitable amount of a TLR4 antagonist for incorporation into the device for release may be in the range from 270 mg to 540 mg, which represents an amount of the agent suitable for 6 months to 1 year of treatment for a patent of approximately 60 kg body weight.

The insertion of the intrauterine device may occur using standard procedures. Efficacy of the treatment may be evaluated by assessing a variety of suitable clinical parameters, such as described in Example 4.

It will also be appreciated that the device described above may have other uses, for example in one or more of the embodiments described herein.

Example 10—Case Studies

Case Study 1: Dysmenorrhea alone—prevention of future pain (e.g. a teenager with severe dysmenorrhea).

A woman with severe dysmenorrhea who may be at risk of developing additional pain-related symptoms including one or more of the following symptoms: bowel symptoms, bladder symptoms, vulval pain, back pain, symptoms due to pelvic muscle pain or spasm, pain associated with intercourse or persistent pelvic pain.

Treatment comprising intra-uterine administration of amitriptyline as described herein may be used to prevent, manage or treat pain-related symptoms.

Case Study 2: Dysmenorrhea plus additional pain or pain related symptoms, requesting non-hormonal treatment of her additional symptoms, without treatment for dysmenorrhea.

A woman with severe dysmenorrhea who has one or more of the following pain-related symptoms: bowel symptoms, bladder symptoms, vulval pain, back pain, symptoms due to pelvic muscle pain or spasm, pain associated with intercourse or persistent pelvic pain.

Treatment comprising intra-uterine administration of amitriptyline as described herein may be used to manage, treat or prevent progression of pain related symptoms.

Case Study 3: Dysmenorrhea alone already managed with a systemic sex hormone, who wishes to use i.u. amitriptyline to prevent development of future pain-related symptoms.

A woman with severe dysmenorrhea managed with the systemic administration of a sex hormone, or treatment affecting sex hormones, who may be at risk of developing additional pain-related symptoms including one or more of the following symptoms: bowel symptoms, bladder symptoms, vulval pain, back pain, symptoms due to pelvic muscle pain or spasm, pain associated with intercourse or persistent pelvic pain.

Treatment comprising systemic administration of a sex hormone (and/or an agent that modulates production and/or activity of a sex hormone), in combination with intra-uterine amitriptyline may be used to manage, treat or prevent progression of pain related symptoms.

Case Study 4: Dysmenorrhea already managed with an i.u. sex hormone in a woman who wants to prevent the development of pain-related future symptoms (for example, a woman already using a levonorgestrel-releasing intra-uterine device who wishes to change to a device that releases levonorgestrel and amitriptyline combined).

A woman with severe dysmenorrhea managed with the intra-uterine administration of a sex hormone and who may be at risk of developing one or more of the following pain-related symptoms: bowel symptoms, bladder symptoms, vulval pain, back pain, symptoms due to pelvic muscle pain or spasm, pain associated with intercourse or persistent pelvic pain.

Treatment comprising intra-uterine administration of a sex hormone in combination with amitriptyline may be used to prevent or reduce the risk of developing symptoms.

Case Study 5: Dysmenorrhea already managed with a systemic sex hormone who already has pain-related symptoms, unable to tolerate systemic amitriptyline.

A woman with severe dysmenorrhea managed with the systemic administration of a sex hormone and who has additional pain-related symptoms including any or all of the following symptoms: bowel symptoms, bladder symptoms, vulval pain, back pain, symptoms due to pelvic muscle pain or spasm, pain associated with intercourse or persistent pelvic pain, but is unable to use systemic amitriptyline due to unacceptable side effects.

Treatment comprising systemic administration of a sex hormone in combination with intra-uterine amitriptyline may be used to manage, treat or prevent progression, of pain related symptoms.

Case Study 6: Dysmenorrhea already managed with an i.u. sex hormone e.g. a woman currently using a levonorgestrel-releasing intra-uterine device who already has pain-related symptoms, unable to tolerate systemic amitriptyline at the dose required.

A woman with severe dysmenorrhea managed with the intra-uterine administration of a sex hormone and who has additional pain-related symptoms including one or more of the following symptoms: bowel symptoms, bladder symptoms, vulval pain, back pain, symptoms due to pelvic muscle pain or spasm, pain associated with intercourse or persistent pelvic pain, but is unable to use systemic amitriptyline due to unacceptable side effects of the drug.

Treatment comprising intra-uterine administration of a sex hormone in combination with intra-uterine amitriptyline may be used to manage, treat or prevent progression, of pain related symptoms, at a dose associated with reduced side effects when compared with systemic administration.

Case Study 7: A woman, regardless of pain, having an intra-uterine device inserted who wished to reduce post insertion pain symptoms.

A woman choosing to use an intra-uterine device for any purpose who may be at risk of developing post insertion pelvic pain, or at risk of worsening existing pelvic pain post insertion.

Treatment comprising intra-uterine administration of amitriptyline may be used to prevent, reduce, manage or treat post insertion pelvic pain.

REFERENCES

Part III: Pain Terms, A Current List with Definitions and Notes on Usage (pp 209-214) Classification of Chronic Pain, Second Edition, IASP Task Force on Taxonomy, edited by H. Merskey and N. Bogduk, IASP Press, Seattle, 1994.

Barton G M, Kagan J C (2009) *Nat. Rev. Immunol.* 9(8), 535-42;

Blasius A L, Beutler B (2010) *Immunity* 32(3), 305-15;

Kawai T, Akira S (2010) *Nat. Immunol.* 11(5), 373-84;

Lester S N, Li K (2014) *J. Mol. Biol.* 426(6), 1246-64;

Li X, Jiang S, Tapping R I (2010) *Cytokine* 49(1), 1-9;

McGettrick A F, O'Neill L A (2010) *Curr. Opin. Immunol.* 22(1), 20-7;

Miggin S M, O'Neill L A (2006) *J. Leukoc. Biol.* 80(2), 220-6; Pasare C, Medzhitov R (2005) *Adv. Exp. Med. Biol.* 560, 11-8;

Reuven E M, Fink A, Shai Y (2014) *Biochim. Biophys. Acta* 1838(6), 1586-93

Coats S R. et al. (2005). *J Immunol.* 175(7):4490-8;

Wang et al (2013) *Chem Soc Rev.* 42(12): 4859-4866;

Cheng, K., et al. 2012. *Angew. Chem. Int. Ed.* 51, 12246;

Sahoo et al (2013) *American Journal of Advanced Drug Delivery*: ISSN-2321-547X; Bhowmik et al (2010) *Annals of Biological Research* 1(1): 70-75;

Widermeesch D. (2010) *Hand. Exp Pharmacol.* 197: 268-298

Sahoo et al (2013) *American Journal of Advanced Drug Delivery* ISSN-2321-547X;

Bhowmik et al (2010) *Annals of Biological Research* 1(1): 70-75;

Widermeesch D. (2010) *Hand. Exp Pharmacol.* 197: 268-298;

Bandyopadhyay A. K. (2008), Novel drug delivery systems, 1st edition;

Everest publishing house, p. 215-220;

Keshwani Bhawana & Arora Pankaj (2014) *Journal of Pharma Research,* 3 (10) 184-187;

Chatterjee Arkendu & Kumar Lalit (2009) *Journal of Pharmacy Research,* 2 (4) 698-700. 3 Mar. 15;

Remington's Pharmaceutical Sciences, 17th ed., Mack Publishing Company, Easton, Pa., 1985;

http://www.nature.com/nmeth/journal/v7/n6/full/nmeth.1455.html

Richardson J. L, and. Illum L (1992) Adv. *Drug Deliv. Rev.* 8: 341-366;

US Patent Application No. 20140127280;

WO 00/00550;

WO 00/29464;

WO 99/10412; and

Finnish patent FI 97947.

The above references are each in their entirety incorporated herein by reference.

Although the present disclosure has been described with reference to particular embodiments, it will be appreciated that the disclosure may be embodied in many other forms. It will also be appreciated that the disclosure described herein is susceptible to variations and modifications other than those specifically described. It is to be understood that the disclosure includes all such variations and modifications. The disclosure also includes all of the steps, features, compositions and compounds referred to, or indicated in this specification, individually or collectively, and any and all combinations of any two or more of the steps or features.

Also, it is to be noted that, as used herein, the singular forms "a", "an" and "the" include plural aspects unless the context already dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Reference to any prior art in this specification is not, and should not be taken as, an acknowledgment or any form of suggestion that this prior art forms part of the common general knowledge in any country.

The subject headings used herein are included only for the ease of reference of the reader and should not be used to limit the subject matter found throughout the disclosure or the claims. The subject headings should not be used in construing the scope of the claims or the claim limitations.

The description provided herein is in relation to several embodiments which may share common characteristics and features. It is to be understood that one or more features of one embodiment may be combinable with one or more features of the other embodiments. In addition, a single feature or combination of features of the embodiments may constitute additional embodiments.

The methods described herein can be performed in one or more suitable orders unless indicated otherwise herein or clearly contradicted by context. The use of examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

Future patent applications may be filed on the basis of the present application, for example by claiming priority from the present application, by claiming a divisional status and/or by claiming a continuation status. It is to be understood that the following claims are provided by way of example only, and are not intended to limit the scope of what may be claimed in any such future application. Nor should the claims be considered to limit the understanding of (or exclude other understandings of) the present disclosure. Features may be added to or omitted from the example claims at a later date.

The invention claimed is:

1. A method of treating pain, and/or pain related symptoms, associated with dysmenorrhea in a subject, the method comprising intrauterine administration to the subject of an effective amount of an agent that inhibits Toll-like Receptor 4 (TLR4) and that reduces activation of the innate immune system, thereby treating the pain and/or the pain related symptoms in the subject.

2. The method according to claim 1, wherein the pain comprises pelvic pain.

3. The method according to claim 1, wherein the pain related symptoms comprises one or more of nausea, fatigue, bowel symptoms, bladder symptoms, vulval pain, back pain, symptoms due to pelvic muscle pain or spasm, chronic pelvic pain, and pain associated with intercourse.

4. The method according to claim 1, wherein the agent comprises TAK242 or amitriptyline.

5. The method according to claim 1, wherein the administration of the agent comprises long term continuous administration to the subject.

6. The method according to claim 1, wherein the method further comprises administration of a sex hormone and/or an agent that modulates production and/or activity of a sex hormone.

7. The method according to claim 1, wherein the method comprises administration to the subject of a dose of the agent of less than 100 µg/kg/day.

8. The method according claim 1, wherein the administration of the agent comprises release of the agent from a device.

9. The method according to claim 1, wherein the agent is administered with an intrauterine device.

10. The method according to claim 9, wherein the agent comprises TAK242 or amitriptyline.

11. The method according to claim 9, wherein the device provides long term continuous release of the agent.

12. The method according to claim 9, wherein the device provides a dose of the agent of less than 100 µg/kg/day.

13. The method according to claim 9, wherein the device further comprises a releasable sex hormone and/or an agent that modulates production and/or activity of a sex hormone.

14. A method of treating pain, and/or pain related symptoms, associated with dysmenorrhea in a subject, the method comprising inserting into the uterus of a subject in need thereof an intrauterine device, said device comprising a releasable agent that inhibits Toll-like Receptor 4 (TLR4) and that reduces activation of the innate immune system.

* * * * *